(12) United States Patent
Sieber et al.

(10) Patent No.: US 8,841,096 B2
(45) Date of Patent: Sep. 23, 2014

(54) METHOD FOR PRODUCING MULTICYCLICAL RING SYSTEMS CARRYING AMINO GROUPS

(75) Inventors: Volker Sieber, Nandlstadt (DE); Katrin Grammann, Oer-Erkenschwick (DE); Broder Ruehmann, Straubing (DE); Thomas Haas, Muenster (DE); Jan Christoph Pfeffer, Essen (DE); Kai Doderer, Rodgau (DE); Claudia Rollmann, Alzenau (DE); Arne Skerra, Freising (DE); Christian Rausch, Windsbach (DE); Alexandra Lerchner, Freising (DE)

(73) Assignee: Evonik Degussa GmbH, Essen (DE)

( * ) Notice: Subject to any disclaimer, the term of this patent is extended or adjusted under 35 U.S.C. 154(b) by 155 days.

(21) Appl. No.: 13/143,354

(22) PCT Filed: Jan. 13, 2010

(86) PCT No.: PCT/EP2010/050331
§ 371 (c)(1),
(2), (4) Date: Jul. 6, 2011

(87) PCT Pub. No.: WO2010/089171
PCT Pub. Date: Aug. 12, 2010

(65) Prior Publication Data
US 2012/0041216 A1 Feb. 16, 2012

(30) Foreign Application Priority Data
Feb. 4, 2009 (DE) .......................... 10 2009 000 592

(51) Int. Cl.
*C12P 17/18* (2006.01)
*C12N 9/06* (2006.01)

(52) U.S. Cl.
USPC ........................... 435/119; 435/191; 549/464

(58) Field of Classification Search
CPC .... C12P 17/181; C12P 13/001; C07D 493/04
USPC .................................... 435/119, 191; 549/464
See application file for complete search history.

(56) References Cited

U.S. PATENT DOCUMENTS

| 5,852,217 A | 12/1998 | Haas et al. |
| 7,148,176 B2 | 12/2006 | Beller et al. |
| 7,758,897 B2 | 7/2010 | Roettger et al. |
| 2001/0047097 A1 | 11/2001 | Trauthwein et al. |
| 2002/0087036 A1 | 7/2002 | Haas et al. |
| 2003/0212298 A1 | 11/2003 | Brasse et al. |
| 2007/0207501 A1 | 9/2007 | Wolf et al. |
| 2009/0117627 A1 | 5/2009 | Doderer et al. |
| 2009/0148899 A1* | 6/2009 | Kawano et al. .............. 435/69.1 |
| 2010/0190219 A1 | 7/2010 | Schaffer et al. |
| 2010/0261237 A1 | 10/2010 | Verseck et al. |
| 2010/0324257 A1 | 12/2010 | Karau et al. |
| 2011/0039313 A1 | 2/2011 | Verseck et al. |
| 2011/0039977 A1 | 2/2011 | Schuetz et al. |
| 2011/0171702 A1 | 7/2011 | Reinecke et al. |
| 2011/0251399 A1 | 10/2011 | Dingerdissen et al. |
| 2011/0269977 A1 | 11/2011 | Dingerdissen et al. |

FOREIGN PATENT DOCUMENTS

| EP | 2 022 852 | 2/2009 |
| WO | 2009 033957 | 3/2009 |
| WO | 2010 089171 | 8/2010 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
U.S. Appl. No. 13/642,412, filed Oct. 19, 2012, Poetter, et al.
U.S. Appl. No. 13/721,481, filed Dec. 20, 2012, Gielen, et al.
U.S. Appl. No. 13/263,761, filed Oct. 10, 2011, Haas, et al.
U.S. Appl. No. 13/820,803, filed Mar. 5, 2013, Klasovsky, et al.
Lucher, Lynne A.; et al. "Reactions Catalyzed by Purified L-Glutamine:Keto-Scyllo-Inositol Aminotransferase, an Enzyme Required for Biosynthesis of Aminocyclitol Antibiotics." Antimicrobial Agents and Chemotherapy, vol. 33, No. 4. pp. 452-459. XP 002622867 (Apr. 1989).
Baxter, Ellen W.; et al. "A review of the article Reductive aminations of carbonyl compounds with borohydride and borane reducing agents." Database Caplus [Online] Chemical Abstracts Service. Database accession No. 2008:1383655. XP 002622692 (2008).
International Search Report issued May 10, 2011 in PCT/EP10/50331 filed Jan. 13, 2010.
U.S. Appl. No. 61/074,848, filed Jun. 23, 2008, Doderer, et al.
U.S. Appl. No. 09/424,701, filed Jan. 25, 2002, Beller, et al.
U.S. Appl. No. 14/000,400, filed Aug. 20, 2013, Klasovsky, et al.
U.S. Appl. No. 13/989,419, filed May 24, 2013, Klasovsky, et al.

* cited by examiner

*Primary Examiner* — Robert Mondesi
*Assistant Examiner* — Md Younus Meah
(74) *Attorney, Agent, or Firm* — Oblon, Spivak, McClelland, Maier & Neustadt, L.L.P.

(57) ABSTRACT

The invention relates to a method for the amination of at least one keto group in a multicyclic ring system comprising at least one keto group into an amino group, using at least one enzyme E having transaminase activity.

16 Claims, 19 Drawing Sheets

SEQUENCE LISTING

<160> NUMBER OF SEQ ID NOS: 33

<210> SEQ ID NO 1
<211> LENGTH: 1257
<212> TYPE: DNA
<213> ORGANISM: Bacillus circulans

<400> SEQUENCE: 1

```
atgaccattc catttgacca ttggccagaa tggcctcaac actccgatcg tacccgccga      60
aaaattgaag aagtgtttca gtcgaacaga tgggcgataa gcggatattg gacgggcgag     120
gaaagcatgg aacggaaatt cgccaaggcg tttgcggatt tcaacggggt cccatactgt     180
gtgccgacga cgagcggctc cacggcttta atgcttgccc ttgaagcgct cggaataggc     240
gaaggggacg aagtcattgt tcccagcctc acttggattg caaccgctac cgccgtatta     300
aacgtgaatg cgcttcctgt ttttgtggac gttgaggcgg atacgtattg tattgatcct     360
caattgataa agtcggccat tacggataaa acgaaagcca ttatcccggt ccatttgttc     420
ggaagtatgg cgaatatgga tgaaataaac gaaatcgcgc aagaacacaa cctttttgtg     480
attgaagact gcgcgcaaag ccacggttcc gtatggaaca accagcgtgc cggaacgata     540
ggagatatag gggcgttcag ctgtcagcag ggcaaagtgt taacggccgg agaagggggg     600
attatcgtga cgaaaaatcc ccgtttattt gaactcatcc aacaattgag agcggattcc     660
agggtttatt gcgatgattc ctccgaattg atgcacggtg acatgcagct ggtaaaaaaa     720
ggggacattc aaggctccaa ctattgcttg tccgaatttc aatcggccat ccttctggat     780
caacttcagg agctggatga caagaacgcg atccgggaaa gaacgccat gttcttgaac     840
gatgccttaa gcaaaattga cggcattaag gtgatgaagc gccctcctca agtcagcaga     900
caaacttatt acggctatgt attccggttc gatccggtga aattcggcgg gttgaatgcg     960
gatcagttct gtgaaattct tcgcgaaaag ctcaatatgg gacgttttta cctgcatccg    1020
ccgtatctcc ccgtacacaa aaatccgttg ttctgcccct ggacaaagaa ccgttatttg    1080
aaatcggttc gtaagacaga agcttattgg agagggcttc attaccggt ctccgaacgt     1140
gcttccgggc aatccatcgt tatccaccat gctattttac tggctgaacc ctcgcatctg    1200
tcgcttctgg tcgatgccgt agccgaactt gcccggaaat tttgcgtgac tcattaa      1257
```

<210> SEQ ID NO 2
<211> LENGTH: 418
<212> TYPE: PRT
<213> ORGANISM: Bacillus circulans

<400> SEQUENCE: 2

```
Met Thr Ile Pro Phe Asp His Trp Pro Glu Trp Pro Gln His Ser Asp
  1               5                  10                  15
```

```
Arg Thr Arg Arg Lys Ile Glu Glu Val Phe Gln Ser Asn Arg Trp Ala
            20                  25                  30
Ile Ser Gly Tyr Trp Thr Gly Glu Glu Ser Met Glu Arg Lys Phe Ala
        35                  40                  45
Lys Ala Phe Ala Asp Phe Asn Gly Val Pro Tyr Cys Val Pro Thr Thr
 50                  55                  60
Ser Gly Ser Thr Ala Leu Met Leu Ala Leu Glu Ala Leu Gly Ile Gly
 65                  70                  75                  80
Glu Gly Asp Glu Val Ile Val Pro Ser Leu Thr Trp Ile Ala Thr Ala
                85                  90                  95
Thr Ala Val Leu Asn Val Asn Ala Leu Pro Val Phe Val Asp Val Glu
                100                 105                 110
Ala Asp Thr Tyr Cys Ile Asp Pro Gln Leu Ile Lys Ser Ala Ile Thr
            115                 120                 125
Asp Lys Thr Lys Ala Ile Ile Pro Val His Leu Phe Gly Ser Met Ala
 130                 135                 140
Asn Met Asp Glu Ile Asn Glu Ile Ala Gln Glu His Asn Leu Phe Val
145                 150                 155                 160
Ile Glu Asp Cys Ala Gln Ser His Gly Ser Val Trp Asn Asn Gln Arg
                165                 170                 175
Ala Gly Thr Ile Gly Asp Ile Gly Ala Phe Ser Cys Gln Gln Gly Lys
            180                 185                 190
Val Leu Thr Ala Gly Glu Gly Gly Ile Ile Val Thr Lys Asn Pro Arg
        195                 200                 205
Leu Phe Glu Leu Ile Gln Gln Leu Arg Ala Asp Ser Arg Val Tyr Cys
    210                 215                 220
Asp Asp Ser Ser Glu Leu Met His Gly Asp Met Gln Leu Val Lys Lys
225                 230                 235                 240
Gly Asp Ile Gln Gly Ser Asn Tyr Cys Leu Ser Glu Phe Gln Ser Ala
                245                 250                 255
Ile Leu Leu Asp Gln Leu Gln Glu Leu Asp Asp Lys Asn Ala Ile Arg
            260                 265                 270
Glu Lys Asn Ala Met Phe Leu Asn Asp Ala Leu Ser Lys Ile Asp Gly
        275                 280                 285
Ile Lys Val Met Lys Arg Pro Pro Gln Val Ser Arg Gln Thr Tyr Tyr
    290                 295                 300
Gly Tyr Val Phe Arg Phe Asp Pro Val Lys Phe Gly Gly Leu Asn Ala
305                 310                 315                 320
Asp Gln Phe Cys Glu Ile Leu Arg Glu Lys Leu Asn Met Gly Thr Phe
                325                 330                 335
Tyr Leu His Pro Pro Tyr Leu Pro Val His Lys Asn Pro Leu Phe Cys
            340                 345                 350
Pro Trp Thr Lys Asn Arg Tyr Leu Lys Ser Val Arg Lys Thr Glu Ala
        355                 360                 365
Tyr Trp Arg Gly Leu His Tyr Pro Val Ser Glu Arg Ala Ser Gly Gln
    370                 375                 380
Ser Ile Val Ile His His Ala Ile Leu Leu Ala Glu Pro Ser His Leu
385                 390                 395                 400
Ser Leu Leu Val Asp Ala Val Ala Glu Leu Ala Arg Lys Phe Cys Val
                405                 410                 415
Thr His
```

<210> SEQ ID NO 3
<211> LENGTH: 1275
<212> TYPE: DNA
<213> ORGANISM: Streptomyces griseus

<400> SEQUENCE: 3

```
atggatagtt cactggcaat ctctggtggg ccacgtctgt ccaaccgcga gtggccacgt     60
tggccacagc cgggtgaccg cgcgctgaaa agcctcgaag acgtcctgac aagcgggcgt    120
tggaccatta gctgcgccta tcagggccgg gattcgtatg agcgtcaatt cgcgtccgca    180
ttcgcggact actgcggctc ggcgatgtgc gtgccgatat cgacgggaac cgcttcgctg    240
gccatcgccc tggaggcctg cggggtcggc gccggcgacg aggtgatcgt ccccggactg    300
agctgggtgg cctccgcctc ggccgttctc ggcatcaacg ccgtccccgt gctggtggac    360
gtcgacccgg ccacgtactg cctggacccg cggccaccg aggcggcgat cacggagcgg    420
acccgggcca tcaccgtggt gcacgcctac tcggccgtcg cggacctgga cgcgctcctg    480
gacatcgccc ggcggcacgg cctgccgctg atcgaggact cgcacacgc gcacggcgcc    540
gggttccgcg ccgtccggt ggggggcgcac ggtgccgcgg agtcttcag catgcagggc    600
agcaagctgc tgacctgcgg cgagggcggt cgctggtga ccgacgacgc ggacgtcgcg    660
ctccgtgcgg agcacctgcg cgcggacgga cgggtggtgc ggcgcgagcc ggtgggcgtg    720
ggcgagatgg agctggagga gaccggccgg atgatgggca gcaacgcctg cctgtcggag    780
ttccacgcgg cggtactgct ggaccagctc gaactgctcg acgggcagaa cgcccgccgg    840
acccgggcgg ccgaccacct caccgaccgg ttgagcgagc tggggatgac ggcccaggcg    900
acggccccgg ggacgaccgc ccgcgcctac taccgctatc tggtgaggct gcccgacgaa    960
gtgctggccg tggcgccggt ggaacggttc gcgcacgcgc tcacggccga actgggcttc   1020
gcggtgaccc agacccaccg tccgctgaac gacaacccgc tgaaccgccc ctcgtcgcgc   1080
aggcggttcg ccaccgacgc ccgctacctg gagcgggtgg accgtcccg gttcgaccct   1140
ccggccgcca gcgcgcccca cgagagcgtt gtgagcttca gccacgaagt gctcctggct   1200
ccgctcgacg ccatcgacga catcgccccgg gcgttccgga aggtcctgga caacgtccgg   1260
gaggtttccc gctga                                                    1275
```

<210> SEQ ID NO 4
<211> LENGTH: 424
<212> TYPE: PRT
<213> ORGANISM: Streptomyces griseus

<400> SEQUENCE: 4

```
Met Asp Ser Ser Leu Ala Ile Ser Gly Gly Pro Arg Leu Ser Asn Arg
1               5                   10                  15

Glu Trp Pro Arg Trp Pro Gln Pro Gly Asp Arg Ala Leu Lys Ser Leu
            20                  25                  30

Glu Asp Val Leu Thr Ser Gly Arg Trp Thr Ile Ser Cys Ala Tyr Gln
        35                  40                  45

Gly Arg Asp Ser Tyr Glu Arg Gln Phe Ala Ser Ala Phe Ala Asp Tyr
    50                  55                  60

Cys Gly Ser Ala Met Cys Val Pro Ile Ser Thr Gly Thr Ala Ser Leu
65                  70                  75                  80

Ala Ile Ala Leu Glu Ala Cys Gly Val Gly Ala Gly Asp Glu Val Ile
                85                  90                  95

Val Pro Gly Leu Ser Trp Val Ala Ser Ala Ser Ala Val Leu Gly Ile
            100                 105                 110
```

Asn Ala Val Pro Val Leu Val Asp Val Asp Pro Ala Thr Tyr Cys Leu
    115                 120                 125

Asp Pro Ala Ala Thr Glu Ala Ala Ile Thr Glu Arg Thr Arg Ala Ile
130                 135                 140

Thr Val Val His Ala Tyr Ser Ala Val Ala Asp Leu Asp Ala Leu Leu
145                 150                 155                 160

Asp Ile Ala Arg Arg His Gly Leu Pro Leu Ile Glu Asp Cys Ala His
                165                 170                 175

Ala His Gly Ala Gly Phe Arg Gly Arg Pro Val Gly Ala His Gly Ala
                180                 185                 190

Ala Gly Val Phe Ser Met Gln Gly Ser Lys Leu Leu Thr Cys Gly Glu
            195                 200                 205

Gly Gly Ala Leu Val Thr Asp Asp Ala Asp Val Ala Leu Arg Ala Glu
        210                 215                 220

His Leu Arg Ala Asp Gly Arg Val Val Arg Arg Glu Pro Val Gly Val
225                 230                 235                 240

Gly Glu Met Glu Leu Glu Thr Gly Arg Met Met Gly Ser Asn Ala
                245                 250                 255

Cys Leu Ser Glu Phe His Ala Ala Val Leu Leu Asp Gln Leu Glu Leu
            260                 265                 270

Leu Asp Gly Gln Asn Ala Arg Arg Thr Arg Ala Ala Asp His Leu Thr
        275                 280                 285

Asp Arg Leu Ser Glu Leu Gly Met Thr Ala Gln Ala Thr Ala Pro Gly
290                 295                 300

Thr Thr Ala Arg Ala Tyr Tyr Arg Tyr Leu Val Arg Leu Pro Asp Glu
305                 310                 315                 320

Val Leu Ala Val Ala Pro Val Glu Arg Phe Ala His Ala Leu Thr Ala
                325                 330                 335

Glu Leu Gly Phe Ala Val Thr Gln Thr His Arg Pro Leu Asn Asp Asn
            340                 345                 350

Pro Leu Asn Arg Pro Ser Ser Arg Arg Phe Ala Thr Asp Ala Arg
        355                 360                 365

Tyr Leu Glu Arg Val Asp Pro Ser Arg Phe Asp Leu Pro Ala Ala Lys
    370                 375                 380

Arg Ala His Glu Ser Val Val Ser Phe Ser His Glu Val Leu Leu Ala
385                 390                 395                 400

Pro Leu Asp Ala Ile Asp Asp Ile Ala Arg Ala Phe Arg Lys Val Leu
                405                 410                 415

Asp Asn Val Arg Glu Val Ser Arg
            420

<210> SEQ ID NO 5
<211> LENGTH: 1305
<212> TYPE: DNA
<213> ORGANISM: Artificial
<220> FEATURE:
<223> OTHER INFORMATION: Codon Optimized gen

<400> SEQUENCE: 5
atgggcagca gccatcacca tcatcaccac agccaggatc cgaattccat gaccatcccg    60
tttgatcatt ggccggaatg gccgcagcat agcgatcgta cccgtcgtaa aatcgaagaa   120
gtgtttcaga gcaaccgttg ggcgattagc ggctattgga ccggcgaaga aagcatggaa   180
cgcaaatttg cgaaagcgtt tgcggatttt aacggcgtgc cgtattgcgt tccgaccacc   240

```
tctggtagca ccgcgctgat gctggccctg gaagcgctgg gcattggcga aggcgatgaa      300
gtgattgtgc cgagcctgac ctggattgcg accgcgaccg cggtgctgaa cgtgaatgcg      360
ctgccggtgt tgtggatgt ggaagcggat acctattgca ttgatccgca gctgattaaa      420
agcgcgatta ccgataaaac caaagcgatt attccggtgc acctgtttgg cagcatggcg      480
aacatggatg aaattaacga atcgcgcag gaacataacc tgttcgttat tgaagattgc      540
gcgcagagcc atggcagcgt gtggaacaac cagcgtgcgg gcaccattgg cgatattggc      600
gcgtttagct gccagcaggg caaagtgctg accgcgggtg aaggcggcat tattgtgacc      660
aaaaatccgc gtctgtttga actgattcag cagctgcgtg cggatagccg tgtgtattgc      720
gatgatagca gcgaactgat gcatggcgat atgcagctgg tgaaaaaagg cgatattcag      780
ggcagcaact attgcctgag cgaatttcag agcgcgattc tgctggatca gctgcaagaa      840
ctggacgata aaacgcgat ccgtgaaaaa aacgcgatgt tctgaacga tgccctgagc      900 aaaattgatg gcatcaaagt gatgaaacgt ccgccgcagg tgagccgtca gacctattat      960
ggctatgtgt tcgttttga tccggtgaaa tttggcggcc tgaacgcgga tcagttttgc     1020
gaaattctgc gcgaaaaact gaacatgggc accttttatc tgcatccgcc gtatctgccg     1080
gtgcataaaa atccgctgtt tgcccgtgg accaaaaacc gttatctgaa aagcgtgcgt     1140 aaaccgaag cgtattggcg tggcctgcat tatccggtga gcgaacgtgc gagcggccag     1200
agcattgtga ttcatcatgc gatcctgctg ccgaaccga gccatctgag cctgctggtt     1260
gatgcggtgg cggaactggc ccgtaaattt tgcgtgaccc attaa                    1305
```

<210> SEQ ID NO 6
<211> LENGTH: 1362
<212> TYPE: DNA
<213> ORGANISM: Vibrio fluvialis

<400> SEQUENCE: 6

```
atgaacaaac cgcagagctg ggaagcgcgt gcggaaacct atagcctgta tggctttacc       60
gatatgccga gcctgcatca gcgtggcacc gttgttgtta cccatggcga aggcccgtat      120
atcgttgatg ttaacggccg tcgttatctg atgcgaata gcggcctgtg gaatatggtt      180
gcgggctttg atcataaagg cctgatcgat gcggcgaaag cgcagtatga acgttttccg      240
ggctatcatg cgtttttgg ccgtatgagc gatcagaccg tgatgctgag cgaaaaactg      300
gttgaagtga gcccgtttga tagcggccgt gtgttttata ccaacagcgg cagcgaagcg      360
aatgatacca tggttaaaat gctgtggttt ctgcatgcgg cggaaggtaa accgcagaaa      420
cgtaaaattc tgacccgctg gaacgcgtat catggcgtta ccgcggttag cgcgagcatg      480
accggcaaac gtataacag cgtgtttggt ctgccgctgc cgggttttgt tcatctgacc      540
tgcccgcatt attggcgtta tggcgaagaa ggcgaaaccg aagaacagtt tgttgcgcgt      600
ctggcgcgtg aactggaaga accattcag cgcgaaggcg cggataccat tgcgggtttt      660
tttgcggaac cggttatggg tgcgggtggt gttattccgc cggcgaaagg ttattttcag      720
gcgattctgc cgatcctgcg caaatatgat attccggtga tcagcgatga agtgatttgc      780
ggctttggtc gtaccggtaa tacctggggt tgcgtgacct atgattttac cccggatgcg      840
atcattagca gcaaaaacct gaccgcgggc tttttcccga tgggtgcggt tattctgggt      900
ccggaactga gcaaacgtct ggaaccgcg attgaagcga tcgaagaatt ccgcatggt      960 tttaccgcga gcgttcatcc ggttggttgt gcgattgcgc tgaaagcgat cgatgtggtt     1020
atgaacgaag gcctggcgga aaatgttcgt cgtctggcgc gcgttttga agaacgcctg     1080
```

```
aaacatattg cggaacgtcc gaacattggc gaatatcgcg gcattggttt tatgtgggcg    1140
ctggaagcgg ttaaagataa agcgagcaaa accccgtttg atggcaatct gagcgtgagc    1200
gaacgtattg cgaataccctg caccgatctg ggtctgattt gtcgtccgct gggtcagagc    1260
gttgttctgt gcccgccgtt tattctgacc gaagcgcaga tggatgaaat gttcgataaa    1320
ctggaaaaag cgctggataa agttttcgcg gaagttgcgt aa                       1362
```

<210> SEQ ID NO 7
<211> LENGTH: 453
<212> TYPE: PRT
<213> ORGANISM: Vibrio fluvialis

<400> SEQUENCE: 7

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320
```

```
Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 8
<211> LENGTH: 1425
<212> TYPE: DNA
<213> ORGANISM: Bacillus megaterium

<400> SEQUENCE: 8
atgagcctga ccgtgcagaa aattaattgg gaacaggtga agaatgggga tcgcaaatat      60
ctgatgcgta cctttagcac ccagaatgaa atcagccgg ttccgattga agcaccgaa      120 ggcgattatc tgattatgcc ggatggcacc cgtctgctgg atttttttaa tcagctgtat     180
tgcgttaatc tgggccagaa aaaccagaaa gtgaacgcag caattaaaga agcactggat     240
cgttacggtt ttgtgtggga tacctatgcc accgattata agcaaaagc cgcaaaaatt     300 attattgaag atattctggg cgatgaagat tggcctggta agttcgtttt tgttagcacc     360
ggtagcgaag cagttgaaac cgcactgaat attgcacgtc tgtataccaa tcgtccgctg     420
gttgttaccc gtgaacatga ttatcatggt tggaccggtg tgcagcaac cgttacccgt     480 ctgcgtagct atcgtagcgg tctggttggt gaaaatagcg aaagctttag cgcacagatt     540
ccgggtagca gctataatag cgcagttctg atggcaccga gcccgaatat gtttcaggat     600
tccgatggta atctgctgaa agatgaaaat ggtgaactgc tgtccgttaa atatacccgt     660
cgcatgattg aaaattatgg tccggaacag gttgcagcag ttattaccga agttagccag     720
ggtgcaggta gcgcaatgcc tccgtatgaa tatattccgc agattcgtaa atgaccaaa     780 gaactgggtg ttctgtggat taatgatgaa gtgctgaccg ttttggtcg taccggtaaa     840 tggtttggct atcagcatta tggtgttcag ccggatatta ttaccatggg taaaggtctg     900
agcagcagca gcctgcctgc aggtgcagtt ctggttagca agaaatcgc agcctttatg     960 gataaacatc gttgggaaag cgttagcacc tatgcaggtc atccggttgc aatggcagca    1020
gtttgtgcaa atctggaagt gatgatgaa gaaaattttg tggaacaggc caaagatagc    1080
ggtgaatata tccgtagcaa actggaactg ctgcaggaaa acataaaag cattggcaat    1140 tttgatggtt atggcctgct gtggattgtt gatattgtga atgccaaaac caaaccccg    1200 tatgttaaac tggatcgcaa ttttacccat ggcatgaatc cgaatcagat tccgacccag    1260
attatcatga aaaagcccct ggaaaaaggt gttctgattg gtggtgttat gccgaatacc    1320
```

```
atgcgtattg gtgcaagcct gaatgttagc cgtggcgata ttgataaagc aatggatgca    1380
ctggattatg ccctggatta tctggaaagc ggtgaatggc agtaa                   1425
```

<210> SEQ ID NO 9
<211> LENGTH: 474
<212> TYPE: PRT
<213> ORGANISM: Bacillus megaterium

<400> SEQUENCE: 9

```
Met Ser Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Tyr Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asp Gly Asn Leu Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Ile Arg
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser
    290                 295                 300

Leu Pro Ala Gly Ala Val Leu Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Phe Val Glu Gln Ala Lys Asp Ser Gly Glu Tyr Ile Arg Ser Lys Leu
```

```
            355                 360                 365
Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln
465                 470

<210> SEQ ID NO 10
<211> LENGTH: 1323
<212> TYPE: DNA
<213> ORGANISM: Alcaligenes denitrificans Y2k-2

<400> SEQUENCE: 10
atgagcgcag caaaactgcc ggatctgagc catctgtgga tgccgtttac cgcaaatcgt      60
cagtttaaag caaatccgcg tctgttagct tctgcaaaag gtatgtatta taccagcttt     120
gatggtcgcc agattctgga tggcaccgca ggtctgtggt gtgttaatgc aggtcattgc     180
cgtgaagaaa ttgttagcgc aattgcaagc caggcaggtg ttatggatta tgcaccgggt     240
tttcagctgg tcatccgct ggcctttgaa gcagcaaccg cagttgcagg tctgatgccg      300
cagggtctgg atcgtgtttt ttttaccaat agcggtagcg aaagcgttga taccgcactg     360
aaaattgcac tggcctatca tcgtgcacgt ggtgaagcac agcgtacccg tctgatcggt     420
cgtgaacgtg ttatcatgg tgttggtttt ggtggtattt ctgtgggtgg tattagcccg      480
aatcgtaaaa cctttagcgg tgcactgctg cctgcagttg atcatctgcc gcataccccat    540 agcctggaac ataatgcatt tacccgtggc agccggaat ggggtgcaca tctggccgat      600
gaactggaac gtattattgc actgcatgat gcaagcacca ttgcagcagt tattgttgaa     660
ccgatggcag gtagcaccgg tgttctggtt ccgcctaaag gttatctgga aaaactgcgt     720
gaaattaccg cacgtcatgg tattctgctg atttttgatg aagtgattac cgcctatggt     780
cgtctgggtg aagcaaccgc agcagcatat tttggtgtta caccggatct gattaccatg     840
gcaaaaggtg ttagcaatgc agcagttccg gcaggtgcag ttgcagttcg tcgtgaagtt     900
catgatgcca ttgttaatgg tccgcagggt ggcattgaat ttttcatgg ctataccctat    960 agcgcacatc cgctggctgc agcagcagtt ctggccaccc tggatattta tcgtcgcgag    1020
gacctgttcg ctcgtgctcg taaactgagc gcagcatttg aagaagcagc ccattctctg    1080
aaaggtgcac cgcatgttat tgatgtgcgt aatattggtc tggttgccgg tattgaactg    1140
tctccgcgtg aaggcgctcc tggcgctcgt gcagctgagg ctttccaaaa atgctttgat    1200
accggtctga tggttcgtta taccggtgat attctggccg ttagccctcc gctgattgtg    1260
gatgaaaatc agatcggcca gatttttgaa ggtattggca aagtgctgaa agaagtggcc    1320
taa                                                                  1323

<210> SEQ ID NO 11
```

<211> LENGTH: 440
<212> TYPE: PRT
<213> ORGANISM: Alcaligenes denitrificans Y2k-2

<400> SEQUENCE: 11

| | | | | | | | | | | | | | | |
|---|---|---|---|---|---|---|---|---|---|---|---|---|---|---|
| Met | Ser | Ala | Ala | Lys | Leu | Pro | Asp | Leu | Ser | His | Leu | Trp | Met | Pro | Phe |
| 1 | | | | 5 | | | | | 10 | | | | | 15 | |

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Thr Ala Val Ala
                85                  90                  95

Gly Leu Met Pro Gln Gly Leu Asp Arg Val Phe Phe Thr Asn Ser Gly
            100                 105                 110

Ser Glu Ser Val Asp Thr Ala Leu Lys Ile Ala Leu Ala Tyr His Arg
        115                 120                 125

Ala Arg Gly Glu Ala Gln Arg Thr Arg Leu Ile Gly Arg Glu Arg Gly
130                 135                 140

Tyr His Gly Val Gly Phe Gly Gly Ile Ser Val Gly Gly Ile Ser Pro
145                 150                 155                 160

Asn Arg Lys Thr Phe Ser Gly Ala Leu Leu Pro Ala Val Asp His Leu
                165                 170                 175

Pro His Thr His Ser Leu Glu His Asn Ala Phe Thr Arg Gly Gln Pro
            180                 185                 190

Glu Trp Gly Ala His Leu Ala Asp Glu Leu Glu Arg Ile Ile Ala Leu
        195                 200                 205

His Asp Ala Ser Thr Ile Ala Ala Val Ile Val Glu Pro Met Ala Gly
210                 215                 220

Ser Thr Gly Val Leu Val Pro Pro Lys Gly Tyr Leu Glu Lys Leu Arg
225                 230                 235                 240

Glu Ile Thr Ala Arg His Gly Ile Leu Leu Ile Phe Asp Glu Val Ile
                245                 250                 255

Thr Ala Tyr Gly Arg Leu Gly Glu Ala Thr Ala Ala Ala Tyr Phe Gly
            260                 265                 270

Val Thr Pro Asp Leu Ile Thr Met Ala Lys Gly Val Ser Asn Ala Ala
        275                 280                 285

Val Pro Ala Gly Ala Val Ala Val Arg Arg Glu Val His Asp Ala Ile
290                 295                 300

Val Asn Gly Pro Gln Gly Gly Ile Glu Phe Phe His Gly Tyr Thr Tyr
305                 310                 315                 320

Ser Ala His Pro Leu Ala Ala Ala Val Leu Ala Thr Leu Asp Ile
                325                 330                 335

Tyr Arg Arg Glu Asp Leu Phe Ala Arg Ala Lys Leu Ser Ala Ala
            340                 345                 350

Phe Glu Glu Ala Ala His Ser Leu Lys Gly Ala Pro His Val Ile Asp
        355                 360                 365

Val Arg Asn Ile Gly Leu Val Ala Gly Ile Glu Leu Ser Pro Arg Glu
370                 375                 380

Gly Ala Pro Gly Ala Arg Ala Ala Glu Ala Phe Gln Lys Cys Phe Asp 385                 390                 395                 400
Thr Gly Leu Met Val Arg Tyr Thr Gly Asp Ile Leu Ala Val Ser Pro
                405                 410                 415

Pro Leu Ile Val Asp Glu Asn Gln Ile Gly Gln Ile Phe Glu Gly Ile
            420                 425                 430

Gly Lys Val Leu Lys Glu Val Ala
        435                 440

<210> SEQ ID NO 12
<211> LENGTH: 1380
<212> TYPE: DNA
<213> ORGANISM: Chromobacterium violaceum

<400> SEQUENCE: 12

```
atgcagaaac agcgtaccac ctctcagtgg cgtgaactgg atgcagcaca tcatctgcat     60
ccgtttaccg ataccgcaag cctgaatcag gcaggtgcac gtgttatgac ccgtggtgaa    120
ggtgtttatc tgtgggatag cgaaggcaac aaaattattg atggtatggc aggtctgtgg    180
tgtgttaatg ttggttatgg tcgcaaagat tttgcagaag cagcacgtcg tcagatggaa    240
gaactgccgt tttataatac cttttttaaa accaccccatc cggcagttgt tgaactgagc    300
agcctgctgg ccgaagttac accggcaggt tttgatcgtg tgttttatac caatagcggt    360
agcgaaagcg ttgataccat gattcgcatg gttcgtcgtt attgggatgt tcagggcaaa    420
ccggaaaaaa aaaccctgat cggtcgttgg aatggttatc atggtagcac cattggtggt    480
gccagcctgg gtggtatgaa atatatgcat gaacagggtg atctgccgat tccgggtatg    540
gcacatattg aacagccgtg gtggtataaa catggcaaag atatgaccac cggatgaattt    600
ggtgttgttg cagcacgttg gctggaagaa aaaattctgg aaattggtgc cgataaagtt    660
gcagcatttg tgggtgaacc gattcagggt gcaggtggtg ttattgttcc gcctgcaacc    720
tattggcctg aaattgaacg tatctgccgc aaatatgatg ttctgctggt tgccgatgaa    780
gttatttgtg ttttggtcg taccggtgaa tggtttggtc atcagcattt tggttttcag    840
ccggacctgt ttaccgcagc caaaggctta tcttctggct atctgccgat tggtgcagtt    900
tttgttggta acgtgttgc agaaggtctg attgcaggcg gtgattttaa tcatggcttt    960
acctatagcg tcatccggt ttgtgcagca gttgcacatg caaatgttgc agcactgcgt   1020
gatgaaggta ttgttcagcg cgtgaaagat gatattggtc gtatatgca gaaacgttgg   1080
cgtgaaacct ttagccgttt tgaacatgtt gatgatgttc gtggtgttgg tatggttcag   1140
gcatttaccc tggtgaaaaa caaagcaaaa cgcgaactgt ttccggattt tggtgaaatt   1200
ggcaccctgt gccgtgatat tttttttcgc aataatctga ttatgcgtgc ctgtggtgat   1260
cacattgtta gcgcaccgcc tctggtgatg acccgtgccg aagttgatga atgctggcc   1320
gttgcagaac gctgtctgga agaatttgaa cagaccctga agcacgtgg tctggcctaa   1380
```

<210> SEQ ID NO 13
<211> LENGTH: 459
<212> TYPE: PRT
<213> ORGANISM: Chromobacterium violaceum

<400> SEQUENCE: 13

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

```
Ala Arg Val Met Thr Arg Gly Glu Gly Val Tyr Leu Trp Asp Ser Glu
         35                  40                  45

Gly Asn Lys Ile Ile Asp Gly Met Ala Gly Leu Trp Cys Val Asn Val
 50                  55                  60

Gly Tyr Gly Arg Lys Asp Phe Ala Glu Ala Ala Arg Arg Gln Met Glu
 65                  70                  75                  80

Glu Leu Pro Phe Tyr Asn Thr Phe Phe Lys Thr Thr His Pro Ala Val
                 85                  90                  95

Val Glu Leu Ser Ser Leu Leu Ala Glu Val Thr Pro Ala Gly Phe Asp
             100                 105                 110

Arg Val Phe Tyr Thr Asn Ser Gly Ser Glu Ser Val Asp Thr Met Ile
         115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                 165                 170                 175

Ile Pro Gly Met Ala His Ile Glu Gln Pro Trp Trp Tyr Lys His Gly
             180                 185                 190

Lys Asp Met Thr Pro Asp Glu Phe Gly Val Val Ala Ala Arg Trp Leu
         195                 200                 205

Glu Glu Lys Ile Leu Glu Ile Gly Ala Asp Lys Val Ala Ala Phe Val
         210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                 245                 250                 255

Val Ala Asp Glu Val Ile Cys Gly Phe Gly Arg Thr Gly Glu Trp Phe
             260                 265                 270

Gly His Gln His Phe Gly Phe Gln Pro Asp Leu Phe Thr Ala Ala Lys
         275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                 325                 330                 335

Ala Ala Leu Arg Asp Glu Gly Ile Val Gln Arg Val Lys Asp Asp Ile
             340                 345                 350

Gly Pro Tyr Met Gln Lys Arg Trp Arg Glu Thr Phe Ser Arg Phe Glu
         355                 360                 365

His Val Asp Asp Val Arg Gly Val Gly Met Val Gln Ala Phe Thr Leu
         370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                 405                 410                 415

Ala Cys Gly Asp His Ile Val Ser Ala Pro Pro Leu Val Met Thr Arg
             420                 425                 430

Ala Glu Val Asp Glu Met Leu Ala Val Ala Glu Arg Cys Leu Glu Glu
         435                 440                 445

Phe Glu Gln Thr Leu Lys Ala Arg Gly Leu Ala
```

```
                 450                 455
```

<210> SEQ ID NO 14
<211> LENGTH: 1431
<212> TYPE: DNA
<213> ORGANISM: Arthrobacter sp.

<400> SEQUENCE: 14

```
atgggtctga ccgtgcagaa aattaattgg gaacaggtga agaatgggga tcgcaaatat      60
ctgatgcgta cctttagcac ccagaatgaa atcagccgg ttccgattga agcaccgaa       120
ggcgattatc tgattacacc gggtggtaca cgtctgctgg attttttaa tcagctgtgc      180
tgtgttaatc tgggtcagaa aaatcagaaa gtgaatgcag ccattaaaga agcactggat     240
cgttacggtt ttgtgtggga tacctatgcc accgattata agcaaaagc cgcaaaaatt      300
attattgaag atattctggg agatgaagat tggcctggta agttcgtttt gttagcacc     360
ggtagcgaag cagttgaaac cgcactgaat attgcacgtc tgtataccaa tcgtccgctg    420
gttgttaccc gtgaacatga ttatcatggt tggaccggtg gtgcagcaac cgttacccgt    480
ctgcgtagct tcgtagcgg tctggttggt gaaaatagcg aaagctttag cgcacagatt     540
ccgggtagca gctgtagcag cgcagttctg atggcaccga gcagcaatac ctttcaggat    600
agcaatggca attatctgaa agatgaaaac ggtgaactgc tgtctgttaa atatacccgt    660
cgcatgattg aaaattatgg tccggaacag gttgcagcag ttattaccga agttagccag   720
ggtgttggta gcaccatgcc tccgtatgaa tatgttccgc agattcgcaa atgaccaaa    780
gaactgggtg ttctgtggat ttctgatgaa gttctgaccg gttttggtcg taccggtaaa   840
tggtttggct atcagcatta tggtgttcag ccggatatta ttaccatggg taaaggtctg   900
agcagcagca gctgcctgc aggtgcagtt gttgtgagca agaaatcgc agcctttatg      960
gataaacatc gttgggaaag cgttagcacc tatgcaggtc atcctgtggc tatggctgcc  1020
gtttgtgcaa atctggaagt gatgatggaa gaaaatctgg ttgaacaggc caaaatagc    1080
ggtgaatata tccgtagcaa actggaactg ctgcaggaaa acataaaag cattggcaat   1140
tttgatggtt atggcctgct gtggattgtt gatattgtga atgccaaaac caaaccccg    1200
tatgttaaac tggatcgcaa ttttcgtcat ggcatgaatc cgaatcagat tccgacccag  1260
atcattatgg aaaaagccct ggaaaaaggt gttctgattg gtggtgcaat gccgaatacc  1320
atgcgtattg gtgcaagcct gaatgttagc cgtggcgata ttgataaagc aatggatgca  1380
ctggattatg ccctggatta tctggaaagc ggtgaatggc agcagagcta a            1431
```

<210> SEQ ID NO 15
<211> LENGTH: 476
<212> TYPE: PRT
<213> ORGANISM: Arthrobacter sp.

<400> SEQUENCE: 15

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Thr Pro Gly
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
```

```
               65                  70                  75                  80
Arg Tyr Gly Phe Val Trp Asp Thr Tyr Ala Thr Asp Tyr Lys Ala Lys
                    85                  90                  95
Ala Ala Lys Ile Ile Ile Glu Asp Ile Leu Gly Asp Glu Asp Trp Pro
                100                 105                 110
Gly Lys Val Arg Phe Val Ser Thr Gly Ser Glu Ala Val Glu Thr Ala
                115                 120                 125
Leu Asn Ile Ala Arg Leu Tyr Thr Asn Arg Pro Leu Val Val Thr Arg
            130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Cys Ser Ser Ala Val Leu Met Ala
                180                 185                 190
Pro Ser Ser Asn Thr Phe Gln Asp Ser Asn Gly Asn Tyr Leu Lys Asp
            195                 200                 205
Glu Asn Gly Glu Leu Leu Ser Val Lys Tyr Thr Arg Arg Met Ile Glu
        210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Val Pro Gln Ile Arg
                245                 250                 255
Lys Met Thr Lys Glu Leu Gly Val Leu Trp Ile Ser Asp Glu Val Leu
                260                 265                 270
Thr Gly Phe Gly Arg Thr Gly Lys Trp Phe Gly Tyr Gln His Tyr Gly
            275                 280                 285
Val Gln Pro Asp Ile Ile Thr Met Gly Lys Gly Leu Ser Ser Ser Ser
        290                 295                 300
Leu Pro Ala Gly Ala Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
Ala Met Ala Ala Val Cys Ala Asn Leu Glu Val Met Met Glu Glu Asn
                340                 345                 350
Leu Val Glu Gln Ala Lys Asn Ser Gly Glu Tyr Ile Arg Ser Lys Leu
            355                 360                 365
Glu Leu Leu Gln Glu Lys His Lys Ser Ile Gly Asn Phe Asp Gly Tyr
        370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
                420                 425                 430
Ile Gly Gly Ala Met Pro Asn Thr Met Arg Ile Gly Ala Ser Leu Asn
            435                 440                 445
Val Ser Arg Gly Asp Ile Asp Lys Ala Met Asp Ala Leu Asp Tyr Ala
        450                 455                 460
Leu Asp Tyr Leu Glu Ser Gly Glu Trp Gln Gln Ser
465                 470                 475

<210> SEQ ID NO 16
```

-continued

<211> LENGTH: 1359
<212> TYPE: DNA
<213> ORGANISM: Vibrio fluvialis

<400> SEQUENCE: 16
atgaataaac cgcagagctg ggaagcacgt gcagaaacct atagcctgta tggctttacc 60
gatatgccga gcctgcatca gcgtggcacc gttgttgtta cccatggtga aggtccgtat 120
atcgtggatg ttaatggtcg tcgttatctg gatgcaaata gcggtctggg taatatggtt 180
gccggttttg atcacaaagg cttaatcgat gcagcaaaag cacagtatga acgctttccg 240
ggttatcatg catttttttgg tcgtatgagc gatcagaccg ttatgctgtc tgaaaaactg 300
gttgaagtga gcccgtttga tagcggtcgt gtgttttatg ataatagcgg cagcgaagcg 360
aatgatacca tggttaaaat gctgtggttt ctgcatgcag cagaaggtaa accgcagaaa 420
cgtaaaattc tgacccgttg gaatgcatat catggtgtta ccgcagttag cgcaagcatg 480
accggtaaac cgtataatag cgtttttggt ctgccgctgc ctggttttgt tcatctgacc 540
tgtccgcatt attggcgtta tggtgaagaa ggtgaaaccg aagaacagtt tgttgcacgt 600
ctggctcgtg aactggaaga aaccattcag cgtgaaggtg cagataccat tgcaggtttt 660
tttgcagaac cggttatggg tgcaggtggt gttattccgc ctgccaaagg ttattttcag 720
gccattctgc cgattctgcg caaatatgat attccggtga tctccgatga agttatttgt 780
ggttttggtc gtaccggtaa tacctggggt tgtgtgacct atgattttac accggatgcc 840
attattagca gcaaaaatct gaccgcaggc tttttttccga tgggtgcagt tattctgggt 900
ccggaactga gcaaacgtct ggaaaccgca attgaagcca ttgaagaatt tccgcatggt 960
tttaccgcaa gcggtcatcc ggttggttgc gctatcgctc tgaaagccat tgatgtggtg 1020
atgaatgaag gtctggccga aaatgttcgt cgtctggctc cgcgttttga agaacgcctg 1080
aaacatattg cagaacgtcc gaatattggt tatcgtggca ttggttttat gtgggcactg 1140
gaagccgtta aagataaagc aagcaaaacc ccgtttgatg gtaatctgag cgttagcgaa 1200
cgtattgcaa atacctgtac cgatctgggt ctgatttgtc gtccgctggg tcagagcgtt 1260
gttctgtgtc cgccttttat tctgaccgaa gcccagatgg atgaaatgtt tgataaactg 1320
gaaaaagccc tggataaagt tttgcagaa gttgcataa 1359

<210> SEQ ID NO 17
<211> LENGTH: 452
<212> TYPE: PRT
<213> ORGANISM: Vibrio fluvialis

<400> SEQUENCE: 17

Met Asn Lys Pro Gln Ser Trp Glu Ala Arg Ala Glu Thr Tyr Ser Leu
1 5 10 15

Tyr Gly Phe Thr Asp Met Pro Ser Leu His Gln Arg Gly Thr Val Val
20 25 30

Val Thr His Gly Glu Gly Pro Tyr Ile Val Asp Val Asn Gly Arg Arg
35 40 45

Tyr Leu Asp Ala Asn Ser Gly Leu Gly Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Phe Gly Arg Met Ser Asp Gln Thr Val Met Leu
85 90 95

Ser Glu Lys Leu Val Glu Val Ser Pro Phe Asp Ser Gly Arg Val Phe

```
            100             105             110
Tyr Asp Asn Ser Gly Ser Glu Ala Asn Asp Thr Met Val Lys Met Leu
        115             120             125

Trp Phe Leu His Ala Ala Glu Gly Lys Pro Gln Lys Arg Lys Ile Leu
130             135             140

Thr Arg Trp Asn Ala Tyr His Gly Val Thr Ala Val Ser Ala Ser Met
145             150             155             160

Thr Gly Lys Pro Tyr Asn Ser Val Phe Gly Leu Pro Leu Pro Gly Phe
            165             170             175

Val His Leu Thr Cys Pro His Tyr Trp Arg Tyr Gly Glu Glu Gly Glu
        180             185             190

Thr Glu Glu Gln Phe Val Ala Arg Leu Ala Arg Glu Leu Glu Glu Thr
    195             200             205

Ile Gln Arg Glu Gly Ala Asp Thr Ile Ala Gly Phe Phe Ala Glu Pro
210             215             220

Val Met Gly Ala Gly Gly Val Ile Pro Pro Ala Lys Gly Tyr Phe Gln
225             230             235             240

Ala Ile Leu Pro Ile Leu Arg Lys Tyr Asp Ile Pro Val Ile Ser Asp
            245             250             255

Glu Val Ile Cys Gly Phe Gly Arg Thr Gly Asn Thr Trp Gly Cys Val
        260             265             270

Thr Tyr Asp Phe Thr Pro Asp Ala Ile Ile Ser Ser Lys Asn Leu Thr
    275             280             285

Ala Gly Phe Phe Pro Met Gly Ala Val Ile Leu Gly Pro Glu Leu Ser
290             295             300

Lys Arg Leu Glu Thr Ala Ile Glu Ala Ile Glu Glu Phe Pro His Gly
305             310             315             320

Phe Thr Ala Ser Gly His Pro Val Gly Cys Ala Ile Ala Leu Lys Ala
            325             330             335

Ile Asp Val Val Met Asn Glu Gly Leu Ala Glu Asn Val Arg Arg Leu
        340             345             350

Ala Pro Arg Phe Glu Glu Arg Leu Lys His Ile Ala Glu Arg Pro Asn
    355             360             365

Ile Gly Tyr Arg Gly Ile Gly Phe Met Trp Ala Leu Glu Ala Val Lys
370             375             380

Asp Lys Ala Ser Lys Thr Pro Phe Asp Gly Asn Leu Ser Val Ser Glu
385             390             395             400

Arg Ile Ala Asn Thr Cys Thr Asp Leu Gly Leu Ile Cys Arg Pro Leu
            405             410             415

Gly Gln Ser Val Val Leu Cys Pro Pro Phe Ile Leu Thr Glu Ala Gln
        420             425             430

Met Asp Glu Met Phe Asp Lys Leu Glu Lys Ala Leu Asp Lys Val Phe
    435             440             445

Ala Glu Val Ala
450

<210> SEQ ID NO 18
<211> LENGTH: 1470
<212> TYPE: DNA
<213> ORGANISM: Pseudomonas putida

<400> SEQUENCE: 18
atgagaattt caagcgtgtc atcagctcct gggagcgtga gttcctgctg tttgctgtct      60
gatcaacttg gtgccgcagg acgcggctgt cgaacaacgg agaagcacat gagcgtcaac     120
```

```
aacccgcaaa cccgtgaatg gcaaaccctg agcggggagc atcacctcgc gcccttcagc    180
gactacaagc agctgaagga aaggggccg cgcatcatca ccaagcccca gggtgtgcat    240
ttgtgggata gcgaggggca caagatcctc gacggcatgg ctggcctgtg gtgcgtggca    300
gtgggttatg gccgtgaaga actggttcag gcggcagaaa agcagatgcg cgagctgccg    360
tactacaacc tgttcttcca gactgcccac ccgcctgcgc tggaactggc caaggcaatc    420
accgatgtcg cgccgcaagg catgacccat gtgttcttca ccggctccgg ctccgaaggc    480
aacgacaccg tgctgcgcat ggtccgccat tactgggcgc tgaaaggcaa gccacagaag    540
cagaccatca tcgccgcat caacggctac acggctcca ccgtggctgg tgccagcctg    600
ggcggcatga gcggcatgca cgagcagggc ggcctgccga tcccgggcat cgtgcatatc    660
ccgcagcctt actggttcgg cgaaggcggc gacatgaccc cggatgagtt cggggtgtgg    720
gcggccgagc aattggagaa aaaaatcctc gaagtcggcg aagacaacgt cgcagccttc    780
atcgccgagc cgatccaggg cgccggcggc gtgatcatcc cgccggaaac ctactggccg    840
aaggtgaagg agattctcgc caagtacgac atcctgttcg tcgccgacga agtgatctgc    900
ggtttcggcc gtaccggcga gtggttcggc tccgactact acgacctcaa gcctgacctg    960
atgaccatcg ccaagggcct gacttccggt tacatcccca tgggcggtgt gatcgtgcgt   1020
gacaccgtgg cccaggtact cagcgaaggc ggcgacttca ccacggctt cacctactcc   1080
ggccacccgg tagcggccgc cgtgggcctg aaaacctgc gcatcctgcg tgacgagaaa   1140
atcgtcgaga aggcgcgcag cgaagcggca ccgtatttgc aaaagcgttt gcgtgaactg   1200
caggaccacc ctctggtggg cgaggtacgc ggcctgggcc tgctcggcgc gatcgagctg   1260
gtcaaggaca aggccacccg cagccgttac gagggcaagg gcgtgggcat gatctgccgc   1320
accttctgct cgaaaacgg cctgatcatg cgcgcggtag gtgacaccat gatcattgcg   1380
ccgccgctgg tgatcagcca tgcagagatc gacgaactgg tggaaaaggc acgtaaatgc   1440
ctggacctga ccctcgaagc gatccgttga                                    1470
```

<210> SEQ ID NO 19
<211> LENGTH: 489
<212> TYPE: PRT
<213> ORGANISM: Pseudomonas putida

<400> SEQUENCE: 19

```
Met Arg Ile Ser Ser Val Ser Ser Ala Pro Gly Ser Val Ser Cys
1               5                   10                  15

Cys Leu Leu Ser Asp Gln Leu Gly Ala Ala Gly Arg Gly Cys Arg Thr
            20                  25                  30

Thr Glu Lys His Met Ser Val Asn Asn Pro Gln Thr Arg Glu Trp Gln
        35                  40                  45

Thr Leu Ser Gly Glu His His Leu Ala Pro Phe Ser Asp Tyr Lys Gln
    50                  55                  60

Leu Lys Glu Lys Gly Pro Arg Ile Ile Thr Lys Ala Gln Gly Val His
65                  70                  75                  80

Leu Trp Asp Ser Glu Gly His Lys Ile Leu Asp Gly Met Ala Gly Leu
                85                  90                  95

Trp Cys Val Ala Val Gly Tyr Gly Arg Glu Glu Leu Val Gln Ala Ala
            100                 105                 110

Glu Lys Gln Met Arg Glu Leu Pro Tyr Tyr Asn Leu Phe Phe Gln Thr
        115                 120                 125
```

```
Ala His Pro Pro Ala Leu Glu Leu Ala Lys Ala Ile Thr Asp Val Ala
    130                 135                 140

Pro Gln Gly Met Thr His Val Phe Phe Thr Gly Ser Gly Ser Glu Gly
145                 150                 155                 160

Asn Asp Thr Val Leu Arg Met Val Arg His Tyr Trp Ala Leu Lys Gly
                165                 170                 175

Lys Pro Gln Lys Gln Thr Ile Ile Gly Arg Ile Asn Gly Tyr His Gly
                180                 185                 190

Ser Thr Val Ala Gly Ala Ser Leu Gly Gly Met Ser Gly Met His Glu
                195                 200                 205

Gln Gly Gly Leu Pro Ile Pro Gly Ile Val His Ile Pro Gln Pro Tyr
    210                 215                 220

Trp Phe Gly Glu Gly Gly Asp Met Thr Pro Asp Glu Phe Gly Val Trp
225                 230                 235                 240

Ala Ala Glu Gln Leu Glu Lys Lys Ile Leu Glu Val Gly Glu Asp Asn
                245                 250                 255

Val Ala Ala Phe Ile Ala Glu Pro Ile Gln Gly Ala Gly Gly Val Ile
                260                 265                 270

Ile Pro Pro Glu Thr Tyr Trp Pro Lys Val Lys Glu Ile Leu Ala Lys
    275                 280                 285

Tyr Asp Ile Leu Phe Val Ala Asp Glu Val Ile Cys Gly Phe Gly Arg
    290                 295                 300

Thr Gly Glu Trp Phe Gly Ser Asp Tyr Tyr Asp Leu Lys Pro Asp Leu
305                 310                 315                 320

Met Thr Ile Ala Lys Gly Leu Thr Ser Gly Tyr Ile Pro Met Gly Gly
                325                 330                 335

Val Ile Val Arg Asp Thr Val Ala Gln Val Leu Ser Glu Gly Gly Asp
                340                 345                 350

Phe Asn His Gly Phe Thr Tyr Ser Gly His Pro Val Ala Ala Ala Val
    355                 360                 365

Gly Leu Glu Asn Leu Arg Ile Leu Arg Asp Glu Lys Ile Val Glu Lys
    370                 375                 380

Ala Arg Ser Glu Ala Ala Pro Tyr Leu Gln Lys Arg Leu Arg Glu Leu
385                 390                 395                 400

Gln Asp His Pro Leu Val Gly Glu Val Arg Gly Leu Gly Leu Leu Gly
                405                 410                 415

Ala Ile Glu Leu Val Lys Asp Lys Ala Thr Arg Ser Arg Tyr Glu Gly
                420                 425                 430

Lys Gly Val Gly Met Ile Cys Arg Thr Phe Cys Phe Glu Asn Gly Leu
    435                 440                 445

Ile Met Arg Ala Val Gly Asp Thr Met Ile Ile Ala Pro Pro Leu Val
    450                 455                 460

Ile Ser His Ala Glu Ile Asp Glu Leu Val Glu Lys Ala Arg Lys Cys
465                 470                 475                 480

Leu Asp Leu Thr Leu Glu Ala Ile Arg
                485

<210> SEQ ID NO 20
<211> LENGTH: 1362
<212> TYPE: DNA
<213> ORGANISM: Pseudomonas putida

<400> SEQUENCE: 20
atgagcgtca caacccgcaa aacccgtgaa tggcaaaccc tgagcgggga gcaccatctc      60
```

```
gcacctttca gtgactacaa gcagctgaag gagaaggggc cgcgcatcat caccaaggcc      120 caggggtgc atttgtggga cagcgagggg cacaagatcc tcgacggcat ggcgggcctg       180
tggtgcgtgg cggtgggtta cggccgtgaa gagctggttc aggcagcaga aaagcagatg      240
cgcgagctgc cgtactacaa cctgttcttc cagacggccc accgcctgc actggaactg      300 gccaaggcca ttaccgatgt ggcgcccgag ggcatgaccc atgtgttctt caccggctcc     360
ggctccgaag gcaacgacac cgtgctgcgc atggtgcgcc actactgggc gttgaagggc     420
aagccgcaca agcagaccat catcggccgt atcaacggct accacggctc caccttcgcc     480
ggtgcttgcc tgggcggcat gagcggcatg cacgagcagg gcggcctgcc gatcccgggc     540
atcgtgcaca tcccgcagcc gtactggttc ggcgaaggcg gtgacatgac cccggatgcg     600
ttcggtatct gggcggccga acagctggag aagaaaatcc tcgaagtcgg cgaagacaac     660
gtcgccgcct tcatcgccga gcctatccag ggcgcaggcg gcgtgatcat cccgccggaa     720
acctactggc cgaaggtgaa ggagattctc gccaagtacg acatcctgtt cgttgccgac     780
gaagtcatct gtggtttcgg ccgtaccggc gagtggttcg gctctgatta ctacgacctc     840
aagcccgacc tgatgaccat cgccaagggc ctgacctccg gttacatccc catgggcggt     900
gtgatcgtgc gtgacaaagt ggccaaggtg atcagcgaag cggtgacttc aaccacggc     960 ttcacctatt cgggccaccc ggtagcggcg gcggtgggcc tggaaaacct gcgcatcctg    1020
cgcgacgagc aaattgtcga gaaggcgcgt actgaagcgg caccgtattt gcaaaagcgt    1080
ttgcgtgagc tgcaggacca cccgctggtg ggtgaagtgc gcggccttgg catgcttggc    1140
gcgatcgagc tggtgaaaga caaggccacc cgcagccgtt acgagggcaa gggcgtgggc    1200
atgatctgcc gcaccttctg cttcgaaaac ggcctgatca tgcgtgcggt gggtgacacc    1260
atgatcatcg cgccgccgct ggtcatcagc catgcgaaa tcgacgaact ggtggaaaag    1320
gcacgcaaat gcctcgacct gacccttgag gcgattcgat aa                        1362
```

<210> SEQ ID NO 21
<211> LENGTH: 453
<212> TYPE: PRT
<213> ORGANISM: Pseudomonas putida

<400> SEQUENCE: 21

```
Met Ser Val Asn Asn Pro Gln Thr Arg Glu Trp Gln Thr Leu Ser Gly
  1               5                  10                  15

Glu His His Leu Ala Pro Phe Ser Asp Tyr Lys Gln Leu Lys Glu Lys
             20                  25                  30

Gly Pro Arg Ile Ile Thr Lys Ala Gln Gly Val His Leu Trp Asp Ser
         35                  40                  45

Glu Gly His Lys Ile Leu Asp Gly Met Ala Gly Leu Trp Cys Val Ala
     50                  55                  60

Val Gly Tyr Gly Arg Glu Glu Leu Val Gln Ala Ala Glu Lys Gln Met
 65                  70                  75                  80

Arg Glu Leu Pro Tyr Tyr Asn Leu Phe Phe Gln Thr Ala His Pro Pro
                 85                  90                  95

Ala Leu Glu Leu Ala Lys Ala Ile Thr Asp Val Ala Pro Glu Gly Met
            100                 105                 110

Thr His Val Phe Phe Thr Gly Ser Gly Ser Glu Gly Asn Asp Thr Val
        115                 120                 125

Leu Arg Met Val Arg His Tyr Trp Ala Leu Lys Gly Lys Pro His Lys
    130                 135                 140
```

Gln Thr Ile Ile Gly Arg Ile Asn Gly Tyr His Gly Ser Thr Phe Ala
145                 150                 155                 160

Gly Ala Cys Leu Gly Gly Met Ser Gly Met His Glu Gln Gly Gly Leu
                165                 170                 175

Pro Ile Pro Gly Ile Val His Ile Pro Gln Pro Tyr Trp Phe Gly Glu
            180                 185                 190

Gly Gly Asp Met Thr Pro Asp Ala Phe Gly Ile Trp Ala Ala Glu Gln
        195                 200                 205

Leu Glu Lys Lys Ile Leu Glu Val Gly Glu Asp Asn Val Ala Ala Phe
    210                 215                 220

Ile Ala Glu Pro Ile Gln Gly Ala Gly Gly Val Ile Ile Pro Pro Glu
225                 230                 235                 240

Thr Tyr Trp Pro Lys Val Lys Glu Ile Leu Ala Lys Tyr Asp Ile Leu
                245                 250                 255

Phe Val Ala Asp Glu Val Ile Cys Gly Phe Gly Arg Thr Gly Glu Trp
            260                 265                 270

Phe Gly Ser Asp Tyr Tyr Asp Leu Lys Pro Asp Leu Met Thr Ile Ala
        275                 280                 285

Lys Gly Leu Thr Ser Gly Tyr Ile Pro Met Gly Gly Val Ile Val Arg
    290                 295                 300

Asp Lys Val Ala Lys Val Ile Ser Glu Gly Gly Asp Phe Asn His Gly
305                 310                 315                 320

Phe Thr Tyr Ser Gly His Pro Val Ala Ala Val Gly Leu Glu Asn
                325                 330                 335

Leu Arg Ile Leu Arg Asp Glu Gln Ile Val Glu Lys Ala Arg Thr Glu
        340                 345                 350

Ala Ala Pro Tyr Leu Gln Lys Arg Leu Arg Glu Leu Gln Asp His Pro
    355                 360                 365

Leu Val Gly Glu Val Arg Gly Leu Gly Met Leu Gly Ala Ile Glu Leu
370                 375                 380

Val Lys Asp Lys Ala Thr Arg Ser Arg Tyr Glu Gly Lys Gly Val Gly
385                 390                 395                 400

Met Ile Cys Arg Thr Phe Cys Phe Glu Asn Gly Leu Ile Met Arg Ala
                405                 410                 415

Val Gly Asp Thr Met Ile Ile Ala Pro Pro Leu Val Ile Ser His Ala
            420                 425                 430

Glu Ile Asp Glu Leu Val Glu Lys Ala Arg Lys Cys Leu Asp Leu Thr
        435                 440                 445

Leu Glu Ala Ile Arg
    450

<210> SEQ ID NO 22
<211> LENGTH: 1359
<212> TYPE: DNA
<213> ORGANISM: Pseudomonas putida

<400> SEQUENCE: 22
atgagtgaac agaattcgca gacccttgcc tggcaatcga tgagccgcga ccaccacctg      60
gccccgttca gcgatgtcaa acaactggcc gagaaaggcc gcgcatcat cacctcggcc     120 aagggcgtgt acctgtggga cagcgagggc aacaagattc ttgatggcat ggcgggcctg     180
tggtgcgtgg cggtgggcta cggtcgcgat gagctggccg aggttgccag ccagcagatg     240
aagcagctgc cttactacaa cctgttcttc cagaccgcgc accgcctgc gctggagctg     300 gccaaggcaa tcgccgatgt ggcgccgcaa ggcatgaacc atgtgttctt caccggctcc     360

```
ggttccgaag gcaacgacac cgtgctgcgc atggtgcgcc attactgggc gctgaagggc      420
aagaagaaca agaacgtcat cattggccgc atcaacggct accacggctc gactgtggcg      480
ggggcagcat tgggtggcat gagcggcatg caccagcagg gcggggtgat tccggatatc      540
gtgcacatcc cgcagccata ttggttcggc gaaggcggcg acatgaccga ggccgacttc      600
ggcgtgtggg cggccgagca gttggagaag aaaatcctcg aagttggcgt ggacaacgtt      660
gccgccttca tcgccgagcc gatccagggc gccggtggtg tgatcattcc accgcaaacc      720
tactggccga aggtgaagga atcctggcc aggtacgaca tcctgttcgt tgccgacgaa       780
gtgatttgcg gttttggccg caccggtgag tggttcggta ccgactacta cgacctcaag      840
cccgacctga tgaccattgc caagggcctg acctctggtt acatccccat gggcggggtg      900
atcgtgcgtg acgaagtggc caaggtcatc agcgaaggcg cgacttcaa ccacggcttc       960
acctattctg ccacccggt ggcggctgcg gtgggcctgg agaacctgcg catcctgcgt      1020
gatgagcaga tcatccagca ggtgcacgat aaaaccgcgc cttatctgca caacgcctg      1080
cgcgaactgg ctgaccaccc gctggtaggc gaagtgcgcg gcctgggcat gctcggcgca      1140
atcgagctgt gaaagacaa ggccaccccg gccaggtacg aaggcaaagg tgtcggcatg      1200
atctgccgcc agcactgctt cgacaacggc ctgatcatgc gcgccgtggg cgacaccatg      1260
atcatcgcgc cgccgctggt gatcagcatc gaggagatcg acgaactggt tgaaaaagcc      1320
cgcaagtgcc tggacctgac ctatgaggct gttcggtaa                            1359
```

<210> SEQ ID NO 23
<211> LENGTH: 452
<212> TYPE: PRT
<213> ORGANISM: Pseudomonas putida

<400> SEQUENCE: 23

```
Met Ser Glu Gln Asn Ser Gln Thr Leu Ala Trp Gln Ser Met Ser Arg
1               5                   10                  15

Asp His His Leu Ala Pro Phe Ser Asp Val Lys Gln Leu Ala Glu Lys
            20                  25                  30

Gly Pro Arg Ile Ile Thr Ser Ala Lys Gly Val Tyr Leu Trp Asp Ser
        35                  40                  45

Glu Gly Asn Lys Ile Leu Asp Gly Met Ala Gly Leu Trp Cys Val Ala
    50                  55                  60

Val Gly Tyr Gly Arg Asp Glu Leu Ala Glu Val Ala Ser Gln Gln Met
65                  70                  75                  80

Lys Gln Leu Pro Tyr Tyr Asn Leu Phe Phe Gln Thr Ala His Pro Pro
                85                  90                  95

Ala Leu Glu Leu Ala Lys Ala Ile Ala Asp Val Ala Pro Gln Gly Met
            100                 105                 110

Asn His Val Phe Phe Thr Gly Ser Gly Ser Glu Gly Asn Asp Thr Val
        115                 120                 125

Leu Arg Met Val Arg His Tyr Trp Ala Leu Lys Gly Lys Lys Asn Lys
    130                 135                 140

Asn Val Ile Ile Gly Arg Ile Asn Gly Tyr His Gly Ser Thr Val Ala
145                 150                 155                 160

Gly Ala Ala Leu Gly Gly Met Ser Gly Met His Gln Gln Gly Gly Val
                165                 170                 175

Ile Pro Asp Ile Val His Ile Pro Gln Pro Tyr Trp Phe Gly Glu Gly
            180                 185                 190
```

```
Gly Asp Met Thr Glu Ala Asp Phe Gly Val Trp Ala Ala Glu Gln Leu
            195                 200                 205
Glu Lys Lys Ile Leu Glu Val Gly Val Asp Asn Val Ala Ala Phe Ile
        210                 215                 220
Ala Glu Pro Ile Gln Gly Ala Gly Gly Val Ile Ile Pro Pro Gln Thr
225                 230                 235                 240
Tyr Trp Pro Lys Val Lys Glu Ile Leu Ala Arg Tyr Asp Ile Leu Phe
                245                 250                 255
Val Ala Asp Glu Val Ile Cys Gly Phe Gly Arg Thr Gly Glu Trp Phe
            260                 265                 270
Gly Thr Asp Tyr Tyr Asp Leu Lys Pro Asp Leu Met Thr Ile Ala Lys
        275                 280                 285
Gly Leu Thr Ser Gly Tyr Ile Pro Met Gly Gly Val Ile Val Arg Asp
    290                 295                 300
Glu Val Ala Lys Val Ile Ser Glu Gly Gly Asp Phe Asn His Gly Phe
305                 310                 315                 320
Thr Tyr Ser Gly His Pro Val Ala Ala Val Gly Leu Glu Asn Leu
                325                 330                 335
Arg Ile Leu Arg Asp Glu Gln Ile Ile Gln Gln Val His Asp Lys Thr
            340                 345                 350
Ala Pro Tyr Leu Gln Gln Arg Leu Arg Glu Leu Ala Asp His Pro Leu
        355                 360                 365
Val Gly Glu Val Arg Gly Leu Gly Met Leu Gly Ala Ile Glu Leu Val
    370                 375                 380
Lys Asp Lys Ala Thr Arg Ala Arg Tyr Glu Gly Lys Gly Val Gly Met
385                 390                 395                 400
Ile Cys Arg Gln His Cys Phe Asp Asn Gly Leu Ile Met Arg Ala Val
                405                 410                 415
Gly Asp Thr Met Ile Ile Ala Pro Pro Leu Val Ile Ser Ile Glu Glu
            420                 425                 430
Ile Asp Glu Leu Val Glu Lys Ala Arg Lys Cys Leu Asp Leu Thr Tyr
        435                 440                 445
Glu Ala Val Arg
    450

<210> SEQ ID NO 24
<211> LENGTH: 1380
<212> TYPE: DNA
<213> ORGANISM: Chromobacterium violaceum

<400> SEQUENCE: 24
atgcagaaac agcgtaccac ctctcagtgg cgtgaactgg atgcggcgca tcatctgcat      60
ccgtttaccg ataccgcgag cctgaatcag gcgggtgcgc gtgtgatgac ccgtggcgaa     120
ggcgtgtatc tgtgggatag cgaaggcaac aaaattattg atggcatggc gggcctgtgg     180
tgcgtgaacg tgggctatgg ccgtaaagat tttgcggaag cggcgcgtcg tcagatggaa     240
gaactgccgt tttataacac cttctttaaa accacccatc cggcggtggt ggaactgagc     300
agcctgctgg ccgaagttac cccggcaggt tttgatcgtg tgttttatac caacagcggc     360
agcgaaagcg tggataccat gattcgtatg gtgcgtcgtt attgggatgt gcagggcaaa     420
ccggaaaaaa aaaccctgat ggccgttgg aacggctatc acggcagcac cattggcgt      480 gcgagcctgg gcggcatgaa atatatgcat gaacagggcg atctgccgat tccgggcatg     540
gcgcatattg aacagccgtg gtggtataaa catggcaaag atatgacccc ggatgaattt     600
```

```
ggcgtggttg cggcgcgttg gctggaagaa aaaattctgg aaatcggcgc ggataaagtg    660
gcggcgtttg tgggcgaacc gattcagggt gcgggcggtg tgattgttcc gccggcaacc    720
tattggccgg aaattgaacg tatttgccgc aaatatgatg tgctgctggt tgcggatgaa    780
gtgatttgcg gctttggccg taccggcgaa tggtttggcc atcagcattt tggctttcag    840
ccggacctgt ttaccgcggc gaaaggcctg agcagcggct atctgccgat ggcgcggtg     900 tttgtgggca acgtgttgc ggaaggtctg attgcgggcg gtgattttaa ccatggcttt    960
acctatagcg gccatccggt gtgtgcggcg gtggcgcatg cgaatgttgc ggcgctgcgt   1020
gatgaaggca ttgtgcagcg tgtgaaagat gatattggcc gtatatgca gaaacgttgg    1080 cgtgaaacct ttagccgttt tgaacatgtg gatgatgtgc gtggcgtggg catggtgcag   1140
gcgtttaccc tggtgaaaaa caaagcgaaa cgtgaactgt ttccggattt tggcgaaatt   1200
ggcaccctgt gccgcgatat ttttttttcgc aacaacctga ttatgcgtgc gtgcggcgat   1260
cacattgtgt ctgcaccgcc gctggttatg acccgtgcgg aagtggatga atgctggcc    1320 gtggcggaac gttgcctgga agaatttgaa cagaccctga agcgcgtgg cctggcctaa    1380
```

<210> SEQ ID NO 25
<211> LENGTH: 459
<212> TYPE: PRT
<213> ORGANISM: Chromobacterium violaceum

<400> SEQUENCE: 25

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240
```

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
        260                 265                 270

Gly His Gln His Phe Gly Phe Gln Pro Asp Leu Phe Thr Ala Ala Lys
    275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 26
<211> LENGTH: 1368
<212> TYPE: DNA
<213> ORGANISM: Rhodobacter sphaeroides

<400> SEQUENCE: 26
atgcgtgacg atgcgccgaa ttcctgggag tcgcgggccg acgcctcttc cttctacggc      60
ttcaccgatc tgccctcggt gcaccagcgc gggacggtcg tgctgaccca cggcaagggg     120
ccctacatct acgacgtgca cgggcgcgcc tatctcgacg cgaactcggg cctctggaac     180
atggtcgcgg gcttcgatca tccggggctg atcgaggctg ccaaggcgca gtacgagcgc     240
ttccccggct atcatgcctt tttcgggcgg atgtcggacc agacggtcat gctgagcgag     300
aagctggtcg aggtctcgcc cttcgcgcgg ggcgggtct tctacaccaa ctccggctcc     360
gaggcgaacg acacgatggt caagatgctc tggttcctcg gcgcggccga gggccacccg     420
gagcggcgca agatcatcac ccgcgtgaac agctatcacg gcgtgaccgc cgtctcggcc     480
tcgatgaccg gcaagcccta caacagtctc ttcgggctgc cgctgccggg cttcatccat     540
gtgggctgcc gcattactg gcgcttcggg caggcgggcg agaccgaggc cgagttcacc     600
cagcggcttg cgcgcgagct cgaggccacc atcatcaagg aaggcccgga cacgatcgcg     660
ggcttcttcg ccgagccggt gatgggtgcc ggtggggtga tcccgccctc cgagggctat     720
ttccaggcgg tccagccggt gctgaagcgc tacggcatcc cgctcatcgc cgacgaggtg     780
atctgcggct cggggcgcac gggcaacacc tgggcctgcc agacctacga tttcatgccc     840
gacgggatca tcagctcgaa gaacatcacc gcgggcttct tcccgatggg cgcggtgatc     900

```
ctcgggccgg agctggccga ccggctgcag gccgcttcgg aagcggtcga ggaattcccg    960
catgggttca ccgcgagcgg ccatccggtc ggctgcgcca tcgcgctgaa ggccatcgat   1020
gtggtgatga acgaggggct ggccgagaat gtccgcgccc tcacgccgaa attcgaggcg   1080
gggctcgcct atctggccga gaacccgaac atcggcgaat ggcgcggcaa ggggctgatg   1140
ggggcgctgg aagcggtgaa ggacaaggcc accaagaccc ccttcccggg cgacctctcg   1200
gtgtcggagc ggattgccaa cagctgcacc gaccatgggc tgatctgccg gccgctcggc   1260
cagtcgatcg tgctctgccc gcccttcatc atgacggagg cgcagatgga cgagatgttc   1320
gagaagctgg cgccgcgct aaaaaaggtc ttcgcagagg tcgcctga                 1368
```

<210> SEQ ID NO 27
<211> LENGTH: 455
<212> TYPE: PRT
<213> ORGANISM: Rhodobacter sphaeroides

<400> SEQUENCE: 27

```
Met Arg Asp Asp Ala Pro Asn Ser Trp Glu Ser Arg Ala Asp Ala Ser
1               5                   10                  15

Ser Phe Tyr Gly Phe Thr Asp Leu Pro Ser Val His Gln Arg Gly Thr
            20                  25                  30

Val Val Leu Thr His Gly Lys Gly Pro Tyr Ile Tyr Asp Val His Gly
        35                  40                  45

Arg Ala Tyr Leu Asp Ala Asn Ser Gly Leu Trp Asn Met Val Ala Gly
    50                  55                  60

Phe Asp His Pro Gly Leu Ile Glu Ala Ala Lys Ala Gln Tyr Glu Arg
65                  70                  75                  80

Phe Pro Gly Tyr His Ala Phe Phe Gly Arg Met Ser Asp Gln Thr Val
                85                  90                  95

Met Leu Ser Glu Lys Leu Val Glu Val Ser Pro Phe Ala Arg Gly Arg
            100                 105                 110

Val Phe Tyr Thr Asn Ser Gly Ser Glu Ala Asn Asp Thr Met Val Lys
        115                 120                 125

Met Leu Trp Phe Leu Gly Ala Ala Glu Gly His Pro Glu Arg Arg Lys
    130                 135                 140

Ile Ile Thr Arg Val Asn Ser Tyr His Gly Val Thr Ala Val Ser Ala
145                 150                 155                 160

Ser Met Thr Gly Lys Pro Tyr Asn Ser Leu Phe Gly Leu Pro Leu Pro
                165                 170                 175

Gly Phe Ile His Val Gly Cys Pro His Tyr Trp Arg Phe Gly Gln Ala
            180                 185                 190

Gly Glu Thr Glu Ala Glu Phe Thr Gln Arg Leu Ala Arg Glu Leu Glu
        195                 200                 205

Ala Thr Ile Ile Lys Glu Gly Pro Asp Thr Ile Ala Gly Phe Phe Ala
    210                 215                 220

Glu Pro Val Met Gly Ala Gly Gly Val Ile Pro Ser Glu Gly Tyr
225                 230                 235                 240

Phe Gln Ala Val Gln Pro Val Leu Lys Arg Tyr Gly Ile Pro Leu Ile
                245                 250                 255

Ala Asp Glu Val Ile Cys Gly Phe Gly Arg Thr Gly Asn Thr Trp Gly
            260                 265                 270

Cys Gln Thr Tyr Asp Phe Met Pro Asp Gly Ile Ile Ser Ser Lys Asn
        275                 280                 285
```

```
Ile Thr Ala Gly Phe Phe Pro Met Gly Ala Val Ile Leu Gly Pro Glu
        290                 295                 300

Leu Ala Asp Arg Leu Gln Ala Ala Ser Glu Ala Val Glu Glu Phe Pro
305                 310                 315                 320

His Gly Phe Thr Ala Ser Gly His Pro Val Gly Cys Ala Ile Ala Leu
                325                 330                 335

Lys Ala Ile Asp Val Val Met Asn Glu Gly Leu Ala Glu Asn Val Arg
                340                 345                 350

Ala Leu Thr Pro Lys Phe Glu Ala Gly Leu Ala Tyr Leu Ala Glu Asn
                355                 360                 365

Pro Asn Ile Gly Glu Trp Arg Gly Lys Gly Leu Met Gly Ala Leu Glu
370                 375                 380

Ala Val Lys Asp Lys Ala Thr Lys Thr Pro Phe Pro Gly Asp Leu Ser
385                 390                 395                 400

Val Ser Glu Arg Ile Ala Asn Ser Cys Thr Asp His Gly Leu Ile Cys
                405                 410                 415

Arg Pro Leu Gly Gln Ser Ile Val Leu Cys Pro Pro Phe Ile Met Thr
                420                 425                 430

Glu Ala Gln Met Asp Glu Met Phe Glu Lys Leu Gly Ala Ala Leu Lys
                435                 440                 445

Lys Val Phe Ala Glu Val Ala
                450                 455

<210> SEQ ID NO 28
<211> LENGTH: 1362
<212> TYPE: DNA
<213> ORGANISM: Paracoccus denitrificans

<400> SEQUENCE: 28
atgaaccaac cgcaaagctg ggaagcccgg gccgagacct attcgctcta cggtttcacc      60
gacatgccct cggtccatca gcggggcacg gtcgtcgtga cccatggcga ggggccctat     120
atcgtcgatg tccatggccg ccgctatctg gatgccaatt cgggcctgtg aacatggtc     180 gcgggcttcg accacaaggg cctgatcgag gccgccaagg cgcaatacga ccgctttccc     240
ggctatcacg cctttttcgg ccgcatgtcc gaccagaccg tgatgctgtc ggaaaagctg     300
gtcgaggtct cgccattcga caacggccgg gtcttctata ccaattccgg ctccgaggcg     360
aacgacacca tggtcaagat gctgtggttc ctgcatgccg ccgagggcaa gccgcaaaag     420
cgcaagatcc tgacgcgctg gaacgcctat acggcgtgac cgcggtttc ggcctcgatg     480 accggcaagc cctacaactc ggtcttcggc ctgccgctgc ccggcttcat ccacctgacc     540
tgcccgcatt actggcgcta tggcgaggaa ggcgagaccg aggcgcaatt cgtcgcccgc     600
ctggcacgcg agcttgagga taccatcacc cgcgagggcg ccgacaccat cgccggcttc     660
ttcgccgagc cggtgatggg cgcgggggg gtgatcccgc cggcgaaggg ttatttccag     720
gccatcctgc cgatcttgcg caagtatgac atcccgatga tctcggacga ggtgatctgc     780
ggcttcgggc gcaccggcaa cacctggggc tgcctgacct acgacttcat gcccgatgcg     840
atcatctcgt ccaagaacct gactgcgggc ttcttcccga tgggcgccgt catcctcggg     900
cccgacctcg ccaagcgggt cgaggccgcg gtcgaggcga tcgaggagtt ccgcacggc     960 ttcaccgcct cgggccatcc ggtcggctgc gccatcgcgc tgaaggccat cgacgtggtg    1020
atgaacgagg gctgccgcga gaatgtccgc gcctcgcac cccgcttcga ggcggggctg    1080
aagcgcatcg ccgaccgccc gaacatcggc gaataccgcg gcatcggctt catgtgggcg    1140
```

```
ctggaggcgg tcaaggacaa gccgaccaag accccttcg acgccaatct ttcggtcagc    1200
gagcgcatcg ccaatacctg caccgatctg gggctgatct gccggccgct gggccagtcc    1260
atcgtgctgt gcccgccctt catcctgacc gaggcgcaga tggacgagat gttcgaaaag    1320
ctggaaaagg cgctcgacaa ggtctttgcc gaggtggcct ga                        1362

<210> SEQ ID NO 29
<211> LENGTH: 453
<212> TYPE: PRT
<213> ORGANISM: Paracoccus denitrificans

<400> SEQUENCE: 29

Met Asn Gln Pro Gln Ser Trp Glu Ala Arg Ala Glu Thr Tyr Ser Leu
1               5                   10                  15

Tyr Gly Phe Thr Asp Met Pro Ser Val His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Glu Ala Ala Lys Ala Gln Tyr Asp Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Asn Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Ile His Leu Thr Cys Pro His Tyr Trp Arg Tyr Gly Glu Glu Gly Glu
            180                 185                 190

Thr Glu Ala Gln Phe Val Ala Arg Leu Ala Arg Glu Leu Glu Asp Thr
        195                 200                 205

Ile Thr Arg Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Met Ile Ser Asp
                245                 250                 255

Glu Val Ile Cys Gly Phe Gly Arg Thr Gly Asn Thr Trp Gly Cys Leu
            260                 265                 270

Thr Tyr Asp Phe Met Pro Asp Ala Ile Ile Ser Ser Lys Asn Leu Thr
        275                 280                 285

Ala Gly Phe Phe Pro Met Gly Ala Val Ile Leu Gly Pro Asp Leu Ala
290                 295                 300

Lys Arg Val Glu Ala Val Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Ala Gly Leu Lys Arg Ile Ala Asp Arg Pro Asn
        355                 360                 365

Ile Gly Glu Tyr Arg Gly Ile Gly Phe Met Trp Ala Leu Glu Ala Val
    370                 375                 380

Lys Asp Lys Pro Thr Lys Thr Pro Phe Asp Ala Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Ile Val Leu Cys Pro Pro Phe Ile Leu Thr Glu Ala
                420                 425                 430

Gln Met Asp Glu Met Phe Glu Lys Leu Glu Lys Ala Leu Asp Lys Val
            435                 440                 445

Phe Ala Glu Val Ala
    450

<210> SEQ ID NO 30
<211> LENGTH: 1380
<212> TYPE: DNA
<213> ORGANISM: Mesorhizobium loti

<400> SEQUENCE: 30
atgctcaacc agtccaacga actcgccgcc tgggatcgcg accacttctt ccatccctcg      60
acccatatgg gcacgcacgc acgcggcgaa agcccgacgc gcatcatggc cggcggtgaa     120
ggcgtcaccg tctgggataa caatggcagg aagagcctgg atgcctttgc cggcctctat     180
tgcgtcaatg tcggctacgg ccgccagaag atcgctgacg ccatcgccgc ccaggcgaaa     240
aacctcgctt actaccacgc ctatgtcggc acggcaccg aggcctcgat aacgctggcc      300
aagatgatca tcgaccgcgc gccaaagggc atgtcgaggg tctatttcgg cctgtcgggc     360
tcggatgcca cgaaaccaa catcaagctg atctggtact acaacaatgt gctgggacgg      420
ccggaaaaga agaagatcat ctcgcgctgg cgcggctatc acggctcggg cgtgatgacc     480
ggttcactga ccgggctcga cctgttccac aacgccttcg acctgccgcg cgcgccgatc     540
ctgcataccg aggcgcccta ctatttccgc cgcgccgacc gctcgatgag cgaagagcag     600
ttctcgcagt attgcgccga caagcttgag gagatgatcc tggccgaggg cccggaaacg     660
gtcgctgcct tcatcggcga gccgattctc ggcactggcg gtatcgtgcc gccgccggct     720
ggctactggg agaaaatcca ggcggtgctg aagaagtacg acgtgctgct ggtcgccgac     780
gaggtggtga cgggcttcgg ccggctgggc accatgttcg gctccgacca ctatggtatc     840
aagccggacc tgatcaccat cgccaagggc ctgacctcgg cctatgcgcc actgtcgggc     900
gtcatcgtcg ccgacaagat gtggcaggtg ctggtcgagg ctccgacaa gctcggctcg      960 ctcggccatg gctggaccta tcggcgcat ccgatctgcg ttgccgccgg ggtagccaat     1020
ctcgaactga tcgacgagat ggatctggtg acgaatgccc gcgagaccgg cgcctatttc    1080
cgcgcagagc tggccaaagc ggtcggcggc cacaaacatg tcggcgacgt gcgcggcgac    1140
ggcatgctgg cggcggtcga gttcgtcgcc gacaaggacg accgggtgtt cttcgacgcg    1200
tcgcagaaga tcgggccgca agtggcgacg gcgcttgccg caagcggcgt catcggccgc    1260
gccatgccgc agggtgacat cctcggcttc gccccgccgc tctgcctgac ccgcgaagaa    1320
gccgacatcg tcgtttcgaa gacggctgat gcggtgaaga gtgtgtttgc caatctctaa    1380
```

<210> SEQ ID NO 31
<211> LENGTH: 459
<212> TYPE: PRT
<213> ORGANISM: Mesorhizobium loti

<400> SEQUENCE: 31

```
Met Leu Asn Gln Ser Asn Glu Leu Ala Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Leu Asp Ala Phe Ala Gly Leu Tyr Cys Val Asn Val
50                  55                  60

Gly Tyr Gly Arg Gln Lys Ile Ala Asp Ala Ile Ala Ala Gln Ala Lys
65                  70                  75                  80

Asn Leu Ala Tyr Tyr His Ala Tyr Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Ile Leu His Thr Glu Ala Pro Tyr Tyr Phe Arg Arg Ala
            180                 185                 190

Asp Arg Ser Met Ser Glu Glu Gln Phe Ser Gln Tyr Cys Ala Asp Lys
        195                 200                 205

Leu Glu Glu Met Ile Leu Ala Glu Gly Pro Glu Thr Val Ala Ala Phe
210                 215                 220

Ile Gly Glu Pro Ile Leu Gly Thr Gly Gly Ile Val Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
290                 295                 300

Asp Lys Met Trp Gln Val Leu Val Glu Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Arg Glu Thr Gly Ala Tyr Phe Arg Ala Glu Leu Ala Lys Ala Val
        355                 360                 365

Gly Gly His Lys His Val Gly Asp Val Arg Gly Asp Gly Met Leu Ala
370                 375                 380
```

```
Ala Val Glu Phe Val Ala Asp Lys Asp Asp Arg Val Phe Phe Asp Ala
385                 390                 395                 400

Ser Gln Lys Ile Gly Pro Gln Val Ala Thr Ala Leu Ala Ala Ser Gly
            405                 410                 415

Val Ile Gly Arg Ala Met Pro Gln Gly Asp Ile Leu Gly Phe Ala Pro
        420                 425                 430

Pro Leu Cys Leu Thr Arg Glu Glu Ala Asp Ile Val Val Ser Lys Thr
            435                 440                 445

Ala Asp Ala Val Lys Ser Val Phe Ala Asn Leu
        450                 455
```

<210> SEQ ID NO 32
<211> LENGTH: 1404
<212> TYPE: DNA
<213> ORGANISM: Rhodobacter sphaeroides

<400> SEQUENCE: 32

```
atgacgcgga atgacgcgac gaatgctgcc ggagcggtgg gcgcggcgat gcgggatcac      60
atcctcttgc ctgcacagga atggcgaag ctcggcaagt ccgcgcagcc ggtgctgact     120
catgccgagg gcatctatgt ccataccgag acggccgcc gcctgatcga cgggccggcg     180
ggcatgtggt gcgcgcaggt gggctacggc cgccgcgaga tcgtcgatgc catggcgcat     240
caggcgatgg tgctgcccta tgcctcgccc tggtatatgg ccacgagccc cgcggcgcgg     300
ctggcggaga agatcgccac gctgacgccg ggcgatctca accggatctt tttcaccacg     360
ggcgggtcga ccgcggtgga cagcgcgctg cgcttctcgg aattctacaa caacgtgctg     420
ggccggccgc agaagaagcg catcatcgtg cgctacgacg gctatcacgg ctcgacggcg     480
ctcaccgccg cctgcaccgg ccgcaccggc aactggccga acttcgacat cgcgcaggac     540
cggatctcgt tcctctcgag ccccaatccg cgccacgccg caaccgcag caggaggcg     600
ttcctcgacg atctggtgca ggaattcgag gaccggatcg agagcctcgg ccccgacacg     660
atcgcggcct tcctggccga ccgatcctc gcctcgggcg gcgtcattat tccgcccgca     720
ggctatcatg cgcgcttcaa ggcgatctgc gagaagcacg acatcctcta tatctcggac     780
gaggtggtga cgggcttcgg ccgttgcggc gagtggttcg cctcggagaa ggtgttcggg     840
gtggtgccgg acatcatcac cttcgccaag ggcgtgacct cgggctatgt gccgctcggc     900
ggccttgcga tctccgaggc ggtgctggcg cggatctcgg gcgagaatgc caagggaagc     960
tggttcacca acggctatac ctacagcaat cagccggtgg cctgcgccgc ggcgcttgcc    1020
aacatcgagc tgatggagcg cgagggcatc gtcgatcagg cgcgcgagat gcggactat    1080
ttcgccgcgg cgctggcttc gctgcgcgat ctgccgggcg tggcggaaac ccggtcggtg    1140
ggcctcgtgg gttgcgtgca atgcctgctc gacccgaccc gggcggacgg cacggccgag    1200
gacaaggcct tcaccctgaa gatcgacgag cgctgcttcg agctcgggct gatcgtgcgc    1260
ccgctgggcg atctctgcgt gatctcgccg ccgctcatca tctcgcgcgc gcagatcgac    1320
gagatggtcg cgatcatgcg gcaggccatc accgaagtga gcgccgccca cggtctgacc    1380
gcgaaagaac cggccgccgt ctaa                                          1404
```

<210> SEQ ID NO 33
<211> LENGTH: 467
<212> TYPE: PRT
<213> ORGANISM: Rhodobacter sphaeroides

<400> SEQUENCE: 33

-continued

```
Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
    275                 280                 285

Ala Lys Gly Val Thr Ser Gly Tyr Val Pro Leu Gly Gly Leu Ala Ile
290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
```

```
                420                 425                 430

Ile Ile Ser Arg Ala Gln Ile Asp Glu Met Val Ala Ile Met Arg Gln
            435                 440                 445

Ala Ile Thr Glu Val Ser Ala Ala His Gly Leu Thr Ala Lys Glu Pro
        450                 455                 460

Ala Ala Val
465
```

METHOD FOR PRODUCING MULTICYCLICAL RING SYSTEMS CARRYING AMINO GROUPS

CROSS-REFERENCE TO RELATED APPLICATIONS

The present application is a 35 U.S.C. §371 National Stage patent application of International patent application PCT/EP2010/050331, filed on Jan. 13, 2010, which claims priority to German patent application DE 102009000592.7, filed on Feb. 4, 2009.

SUBJECT OF THE INVENTION

The subject of the invention is an enzymatic process for the preparation of multicyclic ring systems bearing amino groups.

PRIOR ART

Diaminodianhydrodidesoxyhexitols, being bifunctional amines, are interesting intermediates for chemical reactions. Three stereoisomers are described of 2,5-diamino-1,4:3,6-dianhydro-2,5-didesoxy-D-hexitol (for example Bashford, V. G. and Wiggins, L. F. (1950). *Anhydrides of polyhydric alcohols. XIII. The amino derivatives of* 1,4:3,6-*dianhydromannitol, -sorbitol, and L-iditol and their behavior towards nitrous acid*. Journal of the Chemical Society 1950 371-374): 2,5-diamino-1,4:3,6-dianhydro-2,5-didesoxy-D-mannitol (I), 2,5-diamino-1,4:3,6-dianhydro-2,5-didesoxy-D-glucitol (II) and 2,5-diamino-1,4:3,6-dianhydro-2,5-didesoxy-L-iditol (III). The three stereoisomers differ with regard to the chirality at positions 2 and 5. The amino groups here may be in the endo, endo (I), in the endo, exo (II) or in the exo, exo (III) position, relative to the chair form of the fused five-membered rings.

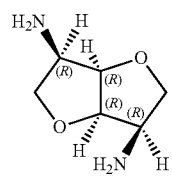
(I)

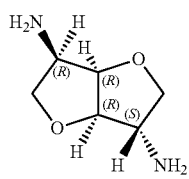
(II)

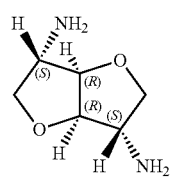
(III)

To date, these molecules have successfully been synthesized starting from the corresponding 1:4,3:6-dianhydrohexitols 1,4:3,6-dianhydro-D-mannitol, Trivial Name Isomannide (IV)

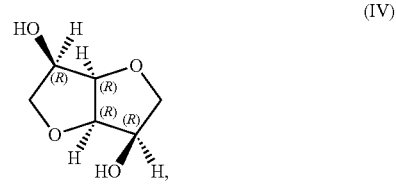
(IV)

1,4:3,6-dianhydro-D-glucitol, Trivial Name Isosorbide (V)

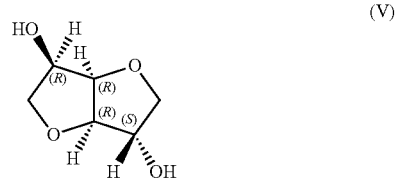
(V)

and 1,4:3,6-dianhydro-L-iditol, Trivial Name Isoidide (VI)

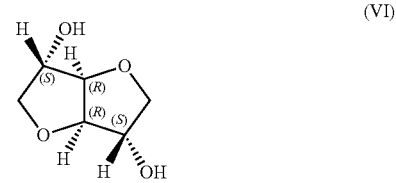
(VI)

via
1.) esterification of the hydroxyl groups (specifically, mesylation or tosylation) and
2.) nucleophilic substitution of the acid groups by azide, followed by reduction to give the diamine.
(cf., for example, Bashford, V. G. and Wiggins, L. F. (1950). *Anhydrides of polyhydric alcohols. XIII. The amino derivatives of* 1, 4:3, 6-*dianhydromannitol, -sorbitol, and L-iditol and their behavior towards nitrous acid* Journal of the Chemical Society 1950 371-374; Thiem, J. and Bachmann, F. (1991). *Synthesis and properties of polyamides derived from anhydro- and dianhydroalditols* Makromolekulare Chemie 192 2163-2182).

Reaction scheme 1 shows this by way of example with reference to example (IV).

Reaction scheme 1:

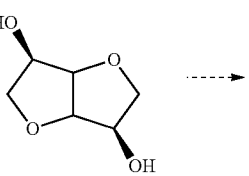

-continued

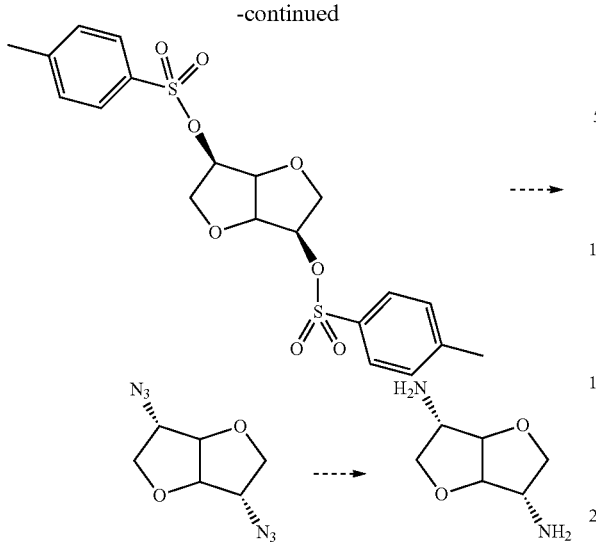

While various modifications of the route shown were tested, they have all been without success:
A) The substitution was not carried out with azide, but directly with ammonia (Montgomery, R. and Wiggins, L. F. (1946). *Anhydrides of polyhydric alcohols. V. 2,5-Diamino-1,4:3,6-dianhydromannitol and -sorbitol and their sulfanilamide derivatives* Journal of the Chemical Society 1946 393-396; Klessing, U.S. Pat. No. 4,535,158; Klessing, DE3028288). This only allowed very low diamine yields to be obtained.
B) Primary amines were used for the substitution instead of azide. Again, the yields were low, and, moreover, only alkylated variants of the diamines were synthesized (Hayashi, H.; Ueno, H.; Suzuki, F. (1992) *Synthesis of stereoisomers of 1,4:3,6-dianhydrohexitol nitrate derivative*, KF-14124. Bioorganic & Medicinal Chemistry Letters, 2(10), 1187-92; Klessing, U.S. Pat. No. 4,535,158; Klessing, DE3028288).
C) As an alternative to the reduction, the diazide was reacted with ketones to give the imine, which was subsequently reduced (De Coster, G., Vandyck K., Van der Eycken, E., Van der Eycken, J. Elseviers, M. and Röper, H. (2002) *D-Isomannide in synthesis: asymmetric Diels-Alder reactions with novel homochiral bis-imine Cu2+-catalysts*. Tetrahedron: Asymmetry 13 (2002) 1673-1679). Again, however, only alkylated variants of the diamines were obtained.

All these routes start with the stereoisomerically pure anhydrohexitols (IV to VI), which show different reactivities in the individual reaction steps, and lead to stereoisomerically pure products (I-III). Here, the azide route results in an inversion of stereochemistry, for example the endo, endo-diol (IV) becomes the exo, exo-diamine (III) (Cope, A. C. and Shen, T. Y. (1956). *Stereochemistry of 1,4:3,6-dianhydrohexitol derivatives* Journal of the American Chemical Society 78, 3177-3182), so that, in the terminology used here, 1,4:3,6-dianhydro-D-mannitol (IV), for example, must be used as the starting material for synthesizing 2,5-diamino-1,4:3,6-dianhydro-2,5-didesoxy-L-iditol (III).

The reaction pathways described have the disadvantage that they are either highly inefficient (substitution of the ditosylate by ammonia, Montgomery, R. and Wiggins, L. F. (1946). *Anhydrides of polyhydric alcohols. V. 2,5-Diamino-1,4:3,6-dianhydromannitol and -sorbitol and their sulfanilamide derivatives* Journal of the Chemical Society 1946 393-396) or that they are very difficult to perform on an industrial scale, such as, for example, the substitution by azide. Moreover, starting from a pure stereoisomer as the starting material yields only precisely one stereoisomer as the product.

This is important in as far as only the isosorbide (V) is available in large amounts and at low cost, and, starting from this compound, only product (II) can be synthesized via the route described. However, it would be interesting to be able to synthesize all three amines (I-III) on an industrial scale, starting from this one available starting material (V).

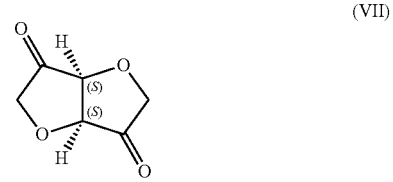

(VII)

The synthesis of the diamines (I) to (III) from diulose (VII) has not been demonstrated to date.

The only substance where synthesis has been successful was the nitrogen-alkylated derivative of the diamine (I), which has the endo/endo configuration (Limberg, G.; Thiem, J. (1994), *Synthetic Approach to N-Alkylated 2,5-Diamino-2,5-didesoxy-1,4;3,6-dianhydroalditols by Reductive Alkylation*. Synthesis; 1994 (3) 317-321).

Various routes, and hence classes of enzymes, for synthesizing amines are found in nature. Examples of these enzymes are transaminases (also referred to as aminotransferases, EC 2.6.1.x), amino acid dehydrogenases (EC 1.4.1.x) and ammonium lyases (EC 4.3.1.x). Here, the typical products of amine formation are α-amino acids, starting from α-ketocarboxylic acids, or α-β-unsaturated carboxylic acids (lyases). In recent times, moreover, so-called amino alcohol dehydrogenases have also been described (U.S. Pat. No. 6,432,688, WO0023608).

Transaminases are pyridoxal phosphate (PLP)-dependent enzymes which, with formation of an oxo group, transfer amino groups from one molecule to the oxo group of a second molecule, with formation of an amino group. Each transaminase, thus, has at least two substrates: the amino donor (in vivo typically an α-amino acid) and the amino acceptor (see scheme). As a rule, however, transaminases have a very high specificity for these two substrates.

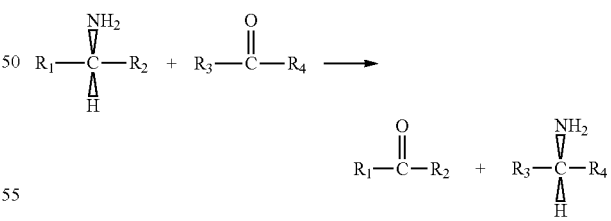

If the amino group is located at a chiral center, then the reactions of transaminases will typically preferentially yield one enantiomer. This is why transaminases are frequently used for the chiral resolution of racemic mixtures (for example Matcham, G. W. and Bowen, A. R. S. Biocatalysis for chiral intermediates: Meeting commercial and technical challenges. Chimica Oggi, 1996, 14(6), 20-24. U.S. Pat. No. 6,344,351, EP404146). A specific group of the transaminases are the ω-transaminases, which have the advantage of being able to transfer amino groups to oxo groups which are not activated by adjacent carboxyl groups. Interestingly, however, these enzymes appear to be predominantly (S)-specific (Shin and Kim, 2001, Comparison of the ω-Transaminase from Different Microorganisms and Application to Production of Chiral Amines Biosci. Biotechnol. Biochem. 65 (8): 1782-88).

There is a great number of transaminases, and a series of substrates and products of transaminases have been described. Thus, it is mainly linear aliphatic ketones and aromatic ketones that have been aminated. A small number of transaminases capable of forming monocyclic aliphatic amines have been described (Lynne A. Lucher, Yu-Ming Chen and James B. Walker (1989) *Reactions Catalyzed by Purified L-Glutamine: Keto-Scyllo-Inositol Aminotransferase, an Enzyme Required for Biosynthesis of Aminocyclitol Antibiotics*. Antimicrobial Agents and Chemotherapy, 1989, p. 452-459; Bum-Yeol Hwang, Hwa-Jin Lee, Yung-Hun Yang, Hwang-Soo Joo, and Byung-Gee Kim (2004) *Characterization and Investigation of Substrate Specificity of the Sugar Aminotransferase WecE from E. coli K12*. Chemistry & Biology, Vol. 11, p. 915-925). In contrast, however, the amination of fused multicyclic aliphatic ketones, and in particular of ketones in multicyclic cis-linked aliphatic ring systems, has, however, been unsuccessful as yet.

SUMMARY OF THE INVENTION

It is an object of the invention to provide a process by means of which multicyclic ring systems bearing at least one amino groups can be prepared and which can be used widely. It is a further object of the invention to be able to carry out stereochemistry-independent syntheses regarding starting materials and/or products.

DESCRIPTION OF THE INVENTION

Figure 1:
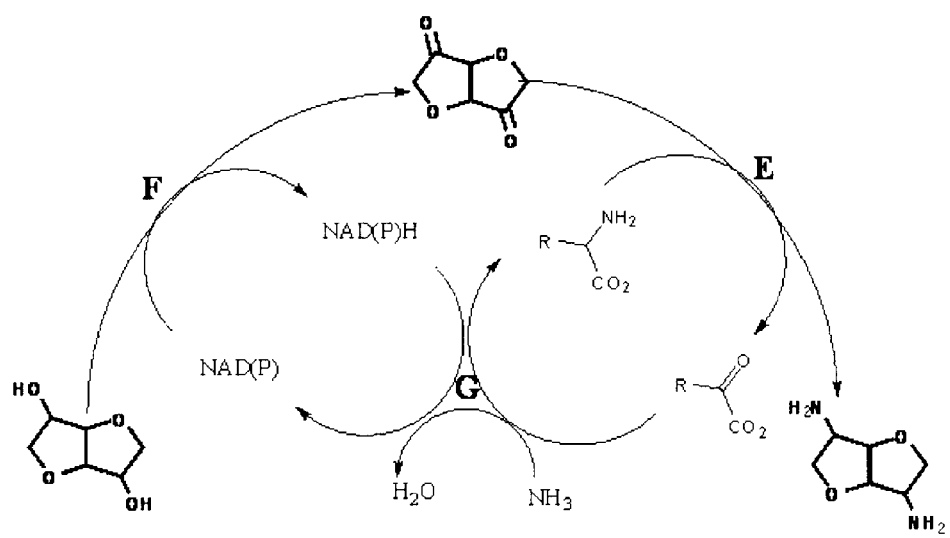
FIG. 1 illustrates a principle of cofactor regeneration with reference to examples of substances.

Surprisingly, it has been found that the enzymatic, transaminase-catalyzed conversion of multicyclic ketone compounds leads to enantiomer mixtures of multicyclic amino compounds.

This could not have been predicted by a person skilled in the art, and, as specified hereinabove, is entirely unexpected since these enzymatic reactions should, as a rule, be highly stereospecific and enzymes furthermore will, as a rule, be highly substrate-specific.

Furthermore, it has been found entirely surprisingly that this enantiomer ratio can be influenced by the pH during the reaction.

In addition it has been found entirely surprisingly that the transaminases accept a very wide range of stereochemical structures of the multicyclic starting materials as substrates. Amines prepared by the process according to the invention are suitable in particular for the preparation of epoxides, polyurethanes or polyamides.

Subject matter of the present invention, therefore, is a process for the amination of at least one keto group in a multicyclic ring system bearing at least one keto group to give an amino group, using at least one enzyme E with transaminase activity.

The process according to the invention for the preparation of a multicyclic ring system bearing amino groups is hereinbelow described by way of example, without it being intended to limit the invention to these exemplary embodiments. If ranges, general formulae or classes of compounds are specified hereinbelow, they are intended not only to comprise the ranges or groups of compounds in question which are explicitly mentioned, but also all subranges and subgroups of compounds which can be obtained by taking out individual values (ranges) or compounds. If documents are cited within the scope of the present description, their content shall belong fully to the disclosure content of the present invention. Unless otherwise specified, all percentages (%) indicated are mass percentages.

A "multicyclic ring system" is understood as meaning substances which are composed of at least two covalently linked ring-shaped molecules.

A "wild type" of a cell preferably refers to a cell whose genome is present in a state as it has been formed by natural means as the result of evolution. The term is used not only for the entire cell, but also for individual genes. Therefore, the term "wild type" therefore will, in particular, not include those cells or those genes whose gene sequences have at least in part been modified by man by means of recombinant methods.

The term "overexpression" describes the increase of the intracellular activity or concentration of one or more enzymes or proteins in an organism which are encoded by the relevant DNA, for example by increasing the copy number of the gene(s), of the open reading frame (ORF) or of the ORFS by at least one copy, functionally linking a strong promoter to the gene or using a gene or allele or ORF which codes for a corresponding enzyme or protein with a high activity and, if appropriate, combining these measures. Examples of strong promoters in $E.\ coli$ which may be mentioned are lac, tac and trp.

By "transamination" there is meant in general the conversion of a ketone into an amine; in contrast to the conventional use, it is not only alpha-keto acids, but all ketones in general, which are meant to be starting materials.

"Homologous expression" or "homologous overexpression" is intended to mean the overexpression of a protein which has already previously existed in the microorganism.

"Heterologous expression" or "heterologous overexpression" is intended to mean the expression or overexpression of a protein which has not previously been present in the microorganism.

In the process according to the invention, the ring system may be any multicyclic ring system which has at least one keto group. It may be a substance composed of a plurality of substituted or unsubstituted, saturated or unsaturated, aliphatic or aromatic rings; in particular, it takes the form of substances whose rings are linked via a molecular bridge or in which at least one atom is involved in the structure of at least two rings at the same time. The rings may be pure carbon rings or heterocycles or mixtures of the two. The preferred hetero atom in heterocycles is oxygen. Preferred are those rings which exclusively include carbon atoms.

Suitable preferred substituents on the ring system are short-chain (1 to 5 C atoms) alkyl radicals or alkoxy radicals which are optionally substituted further.

Multicyclic ring systems which are preferably employed in the process according to the invention are those which include cis-linked rings.

The number of rings in the ring system is preferably two or three rings. It is especially preferred to employ ring systems having two rings.

The ring size of an individual ring forming the ring system is preferably 3 to 9, preferably 4 to 7, especially preferably 5 atoms.

The keto group may be linked to a ring carbon or to a substituent carbon, i.e. to a carbon atom which is not a component of a ring in the ring system.

In the process according to the invention, the keto group is preferably linked to a ring carbon. Especially preferably, the carbon of the keto group is a component of one of the rings.

It is preferred to employ in the process according to the invention compounds selected from the group:

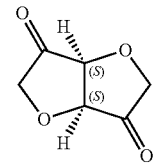

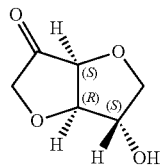

as the multicyclic ring system.

It is possible to employ, in the process according to the invention, multicyclic ring systems of any origin which bear keto groups.

In an especially preferred embodiment of the process according to the invention, there is employed a multicyclic ring system bearing keto groups, which ring system is obtained by oxidation of at least one secondary hydroxyl group of a multicyclic starting ring system to give a ketone (process step A).

This can be illustrated by way of example by reaction scheme 2, where process steps marked with an A represent the oxidation of at least one secondary hydroxyl group to give a keto group, while process steps marked with a B show the transamination step. As shown, steps A and B may proceed one after the other, but also in turns.

Reaction scheme 2:

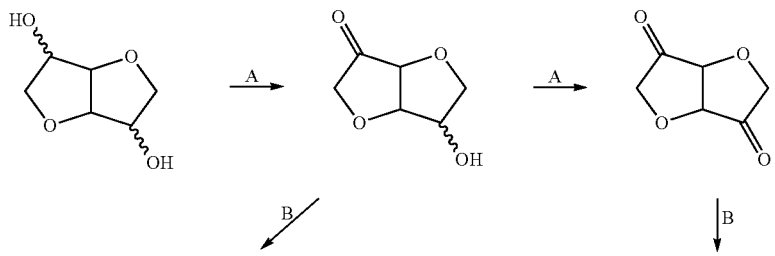

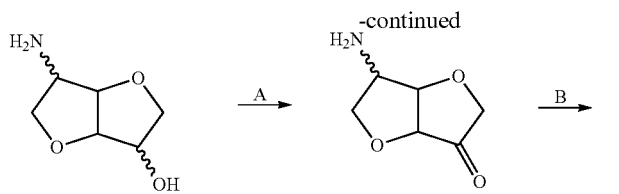

In the multicyclic starting ring system having at least one secondary hydroxyl group, which system is employed in process step A, it is preferred that at least one of the secondary hydroxyl groups is in the endo-position relative to the multicyclic starting ring system. It is equally preferred that at least one of the secondary hydroxyl groups is in the exo-position relative to the multicyclic starting ring system.

The multicyclic starting ring system employed in process step A is preferably at least one compound selected from the group:
isomannide,
isosorbide,
isoidide,

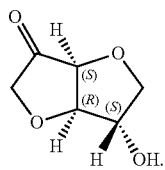

It is possible to employ all known oxidizing processes for the oxidation of the secondary hydroxyl group in the multicyclic starting ring system, for example electrochemical processes, homogeneous or heterogeneous catalytic processes or else enzymatic processes. It is preferred here to employ heterogeneous or homogeneous catalysis processes.

In an especially preferred embodiment of the process according to the invention, the oxidation of the secondary hydroxyl group in the multicyclic starting ring system is catalyzed by an enzyme F with alcohol dehydrogenase activity; F originates especially preferably from *Pichia carsonii, Pichia guillermondii* or *Pichia jadinii*.

Any enzyme with transaminase activity which accepts as substrate the multicyclic ring system employed may be used in the process. It is preferred to use in these processes glutamine-scyllo-inositol transaminases (EC number: 2.6.1.50), preferably from microorganisms of the genera *Bacillus, Micromonospora* or *Streptomyces*, especially preferably *Bacillus circulans* and *Streptomyces griseus*.

Especially preferred enzymes with transaminase activity in the process according to the invention comprise, preferably composed of, amino acid sequence according to SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

In a further especially preferred embodiment of the process, the enzyme with transaminase activity is selected from the group of the functional equivalents of the group composed of functional equivalents of the enzymes selected from among the group composed of the enzymes comprising, preferably composed of, SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, where up to 25%, preferably up to 20%, especially preferably up to 15%, in particular up to 10, 9, 8, 7, 6, 5, 4, 3, 2, 1% of the amino acid residues have been modified by deletion, substitution, an insertion or a combination of deletion, substitution and insertion, over the corresponding SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, respectively, where the functional equivalents retain at least 50%, preferably 65%, especially preferably 80%, in particular more than 90%, of the enzymatic activity of the enzyme comprising, preferably composed of, SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, respectively. In this context, enzymatic activity of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, respectively, is understood as meaning the ability of transaminating diulose (VII) to give the corresponding diamines diaminoisosorbide (II) and diaminoisoidide (III). Enzymes with transaminase activity E which can be employed in the process according to the invention are also "functional equivalents" or "functional derivatives". "Functional equivalents" or analogs of the specifically disclosed enzymes are, within the scope of the present invention, polypeptides which differ from the above but which still have the desired biological activity, such as, for example, substrate specificity. Thus, for example, "functional equivalents" are understood as meaning enzymes which transanimate diulose (VII) to give the corresponding diamines and which have at least 50%, preferably 60%, especially preferably 75%, very especially preferably 90% of the activity of an enzyme with the amino acid sequence mentioned in SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, respectively. Moreover, enzyme E and its functional equivalents are preferably stable between pH 4 to 10 and advantageously have a pH activity optimum at between pH 5 and 8 and a temperature activity optimum in the range of from 20° C. to 80° C.

"Functional equivalents" may in particular also be understood as meaning mutants which include in at least one sequence position of the abovementioned amino acid sequences an amino acid which is other than the specifically mentioned amino acid, but which mutants still retain one of the abovementioned biological activities. Therefore, "functional equivalents" comprise the mutants obtainable by one or more amino acid additions, substitutions, deletions and/or inversions, it being possible for the abovementioned modifications to occur in any sequence position as long as they lead to a mutant with the property profile according to the invention. Functional equivalence exists in particular also when the reactivity patterns between mutant and unmodified polypeptide agree in terms of quality, i.e. when, for example, identical substrates are converted at different rates.

Examples of suitable amino acid substitutions can be gleaned from the following table:

| Original residue | Substitution examples |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Met; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" may, according to the invention, also be understood as meaning in particular mutants which include in at least one sequence position of the abovementioned amino acid sequences an amino acid other than the specifically mentioned amino acid, but which mutants still retain one of the abovementioned biological activities. Therefore, "functional equivalents" also preferably comprise the mutants obtainable by one or more amino acid additions, substitutions, deletions and/or inversions, it being possible for the abovementioned modifications to occur in any sequence position as long as they lead to a mutant with the property profile according to the invention. Functional equivalence exists in particular also when the reactivity patterns between mutant and unmodified polypeptide agree in terms of quality, i.e. when, for example, identical substrates are converted at different rates.

"Functional equivalents" in the above sense may also be "precursors" of the described polypeptides, and "functional derivatives" and "salts" of the polypeptides. "Precursors" may be natural or synthetic precursors of the polypeptides with or without the desired biological activity. The term "salts" is understood as meaning not only salts of carboxyl groups, but also acid addition salts of amino groups of the protein molecules according to the invention. Salts of carboxyl groups can be prepared in a manner known per se and comprise inorganic salts, such as, for example, sodium salts, calcium salts, ammonium salts, iron salts and zinc salts, and salts with organic bases, such as, for example, amines, such as triethanolamine, arginine, lysine, piperidine and the like. Acid addition salts such as, for example, salts with mineral acids, such as hydrochloric acid or sulfuric acid, and salts with organic acids, such as acetic acid and oxalic acid, are likewise subject matter of the invention.

"Functional derivatives" of polypeptides according to the invention can be prepared on functional amino acid side groups or on their N- or C-terminal ends, using known techniques. Such derivatives comprise, for example, aliphatic esters of carboxylic acid groups, amides of carboxylic acid groups, obtainable by reaction with ammonia or with a primary or secondary amine, N-acyl derivatives of free amino groups, obtained by reaction with acyl groups, or O-acyl derivatives of free hydroxyl groups, obtained by reaction with acyl groups. Naturally, "functional equivalents" may also be polypeptides which can be obtained from other organisms, and naturally occurring variants. For example, ranges of homologous sequence regions can be determined by sequence comparison, and equivalent enzymes can be found by referring to the specific requirements of the invention.

"Functional equivalents" likewise comprise fragments, preferably individual domains or sequence motives, of the polypeptides according to the invention which have for example the desired biological function.

"Functional equivalents" may, moreover, be fusion proteins which include one of the abovementioned polypeptide sequences or functional equivalents derived therefrom and at least one further, functionally different, heterologous sequence in functional N- or C-terminal linkage (i.e. without the fusion protein moieties mutually adversely affecting each other functionally to a substantial degree). Nonlimiting examples of such heterologous sequences are, for example, signal peptides or enzymes.

According to the invention, "functional equivalents" may be homologs to the specifically disclosed enzymes. The homologs have at least 60%, preferably at least 75%, in particular at least 85%, such as, for example, 90%, 95% or 99%, homology to one of the specifically disclosed amino acid sequences, calculated by the algorithm of Pearson and Lipman (Pearson W R, Lipman D J. *Improved tools for biological sequence comparison*. Proc Natl Acad Sci USA. 1988 April; 85(8):2444-8). A percentage homology of a homologous polypeptide according to the invention means in particular the percentage identity of the amino acid residues based on the total length of one of the amino acid sequences described specifically herein.

In the event of protein glycosylation, which is possible, "functional equivalents" according to the invention comprise enzymes of the above-specified type in deglycosylated or glycosylated form, and modified forms obtainable by altering the glycosylation pattern.

Homologs of the enzymes according to the invention can be generated by mutagenesis, for example by point mutation or by truncating the enzyme.

Homologs of the enzyme according to the invention can be identified by screening combinatorial libraries of mutants, such as, for example, truncation mutants. For example, such a library of protein variants can be generated by combinatorial mutagenesis at the nucleic acid level such as, for example, by enzymatically ligating a mixture of synthetic oligonucleotides. A multiplicity of processes exist which can be used for generating libraries of potential homologs, starting with a degenerate oligonucleotide sequence. The chemical synthesis of a degenerate gene sequence may be performed in an automatic DNA synthesizer, and the synthetic gene may then be ligated into a suitable expression vector. The use of a set of degenerate genes makes it possible to provide a mixture of all sequences which code for the desired set of potential protein sequences. Processes for the synthesis of degenerate oligonucleotides are known to a person skilled in the art (for example Ike Y, Ikuta S, Sato M, Huang T, Itakura K. *Solid phase synthesis of polynucleotides. VIII. Synthesis of mixed oligodeoxyribonucleotides by the phosphotriester solid phase method*. Nucleic Acids Res. 1983 Jan. 25; 11(2):477-88). The prior art knows a plurality of techniques for screening gene products of combinatorial libraries which have been generated by point mutations or by truncation, and for screening cDNA libraries for gene products with a selected property. These techniques can be adapted to the rapid screening of the gene libraries which have been generated by combinatorial mutagenesis of homologs according to the invention. The most frequently used techniques for screening large gene libraries which are subjected to high-throughput analysis comprise cloning the gene library into replicating expression vectors, transforming the suitable cells with the resulting vector library and expressing the combinatorial genes under conditions under which the detection of the desired activity simplifies the isolation of the vector which codes for the gene whose product has been detected. Recursive ensemble mutagenesis (REM), a technique which increases the frequency of functional mutants in the libraries, may, in combination with the screening tests, be used to identify homologs (Arkin A P, Youvan D C. *An algorithm for protein engineering: simulations of recursive ensemble mutagenesis.* Proc. Natl. Acad. Sci. USA. 1992 Aug. 15; 89(16):7811-5).

The enzymes employed in the process according to the invention can be prepared by the methods known to a person skilled in the art, which include, for example, the production in cell cultures or in microorganisms, or in-vitro translation. These methods require in particular nucleic acid sequences (single- and double-stranded DNA and RNA sequences such as, for example, cDNA and mRNA).

Subject matter of the invention is the use of the nucleic acid sequences which code for an enzyme with transaminase activity according to the invention or for one of its functional equivalents. Preferred are nucleic acid sequences which code for the amino acid sequence according to SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33 or characteristic part-sequences thereof. The nucleic acids in question can be determined readily by back-translating SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33 according to the genetic code. Here, what is known as codon optimization, in other words the adaptation of the codons to the frequently used codons of particularly highly expressed genes of the envisaged host organism in which the nucleic acid is intended to be expressed. Nucleic acid sequences can be prepared by chemical synthesis from the nucleotide units, such as, for example, by fragment condensation of individual overlapping complementary nucleic acid units. The chemical synthesis of oligonucleotides can be performed for example by the phosphoamidite method (Koster H, Blocker H, Frank R, Geussenhainer S, Kaiser W. *Total synthesis of a structural gene for the human peptide hormone angiotensin II.* Hoppe Seylers Z Physiol Chem. 1975 October; 356(10):1585-93). It is also possible to employ nucleic acid sequences which code for one of the above polypeptides and their functional equivalents, which are available for example using artificial nucleotide analogs, in the process according to the invention.

Likewise, it is possible to employ nucleic acids which hybridize with abovementioned coding sequences under stringent conditions. This characteristic is understood as meaning the ability of a poly- or oligonucleotide to bind under stringent conditions to a virtually complementary sequence, while unspecific binding between noncomplementary partners fails to materialize under these conditions. To this end, the sequences should have a complementarity of 70-100%, preferably 90-100%. The property of complementary sequences of being able to bind specifically with each other is exploited for example in the screening of genomic libraries or cDNA libraries, in the Northern or Southern blot technique or in the binding of primers in the PCR or RT-PCR. Usually, one employs oligonucleotides of a length of 30 base pairs or longer. Stringent conditions, for example in the Northern blot technique, are understood as meaning the use of a wash solution with a temperature of 50-70° C., preferably 60-65° C., for example 0.1×SSC buffer containing 0.1% SDS (20× SSC: 3M NaCl, 0.3M Na citrate, pH 7.0) for eluting unspecifically hybridized cDNA probes or oligonucleotides. During this process, only highly complementary nucleic acids remain bound to each other, as has been mentioned above. The setting of stringent conditions is known to a person skilled in the art and described, for example, in Ausubel et al., *Current Protocols in Molecular Biology*, John Wiley & Sons, N.Y. (1989), 6.3.1-6.3.6. If appropriate, such polynucleotides can be multiplied by means of PCR, using suitable primers, and subsequently isolated. Moreover, such polynucleotides may also be synthesized chemically.

It is especially preferred to use a nucleic acid sequence comprising SEQ ID NO: 1 to provide the enzyme E in the process according to the invention.

The invention furthermore relates to expression constructs, comprising, under the genetic control of regulatory nucleic acid sequences, a nucleic acid sequence which codes for a polypeptide according to the invention, and to vectors, comprising at least one of these expression constructs.

Preferably, such constructs according to the invention comprise a promoter 5'-upstream of the respective coding sequence, and, 3'-downstream, a terminator sequence and, if appropriate, further customary regulatory elements, in each case in operable linkage with the coding sequence.

An "operable linkage" is understood as meaning the sequential arrangement of promoter, coding sequence, terminator and, if appropriate, further regulatory elements in such a way that each of the regulatory elements can fulfil its intended function upon expression of the coding sequence. Examples of operably linkable sequences are targeting sequences, and also enhancers, polyadenylation signals and the like. Further regulatory elements comprise selectable markers, amplification signals, replication origins and the like. Examples of suitable regulatory sequences are described in Goeddel, *Gene Expression Technology: Methods in Enzymology* 185, Academic Press, San Diego, Calif. (1990).

A nucleic acid construct according to the invention is understood as meaning in particular those in which the gene for a transaminase according to the invention have been operably or functionally linked to one or more regulatory signals for regulating, for example increasing, gene expression.

A preferred nucleic acid construct advantageously also comprises one or more of the already-mentioned "enhancer" sequences, in functional linkage with the promoter, which sequences make possible an enhanced expression of the nucleic acid sequence. It is also possible to insert additional advantageous sequences at the 3' end of the DNA sequences, such as further regulatory elements or terminators. One or more copies of the nucleic acids according to the invention may be present in the construct. Further markers, such as genes complementing antibiotic resistances or auxotrophisms, may also be present in the construct, if appropriate in order to select for the construct. For expression in a host organism, the nucleic acid construct is advantageously inserted into a vector such as, for example, a plasmid or a phage, which vector makes possible the optimal expression of the genes in the host. Apart from plasmids and phages, vectors are also understood as meaning all the other vectors with which the person skilled in the art is familiar, that is, for example, viruses such as SV40, CMV, baculovirus and adenovirus, and linear or circular DNA. These vectors can be replicated autonomously in the host organism or else they can be replicated chromosomally. Further vectors and plasmids are known to a person skilled in the art and can be found for example in the book *Cloning Vectors, A laboratory Manual* (Eds. Pouwels P. H. et al. Elsevier, Amsterdam-N.Y.-Oxford, 1985). In a further embodiment of the vector, the vector comprising the nucleic acid construct according to the invention or the nucleic acid according to the invention can advantageously also be introduced into the microorganisms in the form of a linear DNA and integrated into the genome of the host organism via heterologous or homologous recombination. This linear DNA can consist of a linearized vector such as a plasmid or else only of the nucleic acid construct or the nucleic acid according to the invention.

It is preferred to produce the enzymes used in the process according to the invention in microorganisms. Microorganisms are, as a rule, grown in a liquid medium which contains a carbon source, in most cases in the form of sugars, a nitrogen source, in most cases in the form of organic nitrogen sources such as yeast extract or salts such as ammonium sulfate, trace elements such as iron salts, manganese salts, magnesium salts and, if appropriate, vitamins, at temperatures of between 0° C. and 100° C., preferably between 10° C. to 60° C., while passing in oxygen. During this process, the pH of the liquid medium can be maintained at a fixed value, that is can be regulated during culturing or not. Culturing can be carried out batchwise, semi-batchwise or continuously. Nutrients can be provided at the beginning of the fermentation or fed in semicontinuously or continuously.

The enzymes can be purified with the aid of known chromatographic methods. These include, for example, gel filtration, anion and cation exchange chromatography and hydrophobic interaction chromatography. Other customary methods such as ultrafiltration, crystallization, salting out, dialysis and native gel electrophoresis may also be employed. Further suitable methods are described, for example, in Cooper, F. G., *Biochemische Arbeitsmethoden*, Verlag Walter de Gruyter, Berlin, N.Y. To isolate the recombinant protein, it may be advantageous to use vector systems or oligonucleotides which extend the cDNA by certain nucleotide sequences and thus code for modified polypeptides or fusion proteins which serve the purpose of, for example, simplifying purification. Such suitable modifications are, for example, so-called "tags", which act as anchors and which can frequently also be recognized by antibodies as antigens such as, for example, His tags, Strep tags, myc tags, Flag tags, MBP tags and GST tags. These anchors can serve the purpose of attaching the proteins to a solid support such as, for example, a polymer matrix which, for example, can be packed into a chromatography column, or to a microtiter plate or to any other support.

In a preferred embodiment, the process according to the invention is carried out in the presence of the organisms required for the production of the enzymes E and/or F, i.e. the transamination on the multicyclic ring system and/or, if appropriate, the oxidation on the starting ring system may take place during the culturing and growth of the organisms which produce E and/or F. The starting material may be added directly to the cultivation or after the cultivation.

The organism employed for the production of the enzymes used in the process according to the invention may be immobilized or else freely mobile in the culture. This organism employed may be a prokaryote or a eukaryote. It may take the form of mammalian cells (such as, for example, human cells), plant cells or microorganisms such as yeasts, fungi or bacteria. It is preferred to employ a microorganism as the organism in the process according to the invention.

It is especially preferred to employ, in the process according to the invention, an organism which is selected from the group:
at least one member of the genus *Bacillus*,
at least one member of the genus *Lactobacillus*,
at least one member of the genus *Pseudomonas*,
at least one member of the genus *Streptococcus*,
at least one member of the genus *Streptomyces*,
at least one member of the genus *Hansenula*,
at least one member of the genus *Pichia*,
at least one member of the genus *Aspergillus*,
at least one member of the genus *Escherichia* and/or
at least one member of the genus *Saccharomyces*.

It is advantageous to employ Gram-positive or Gram-negative bacteria, preferably bacteria from the families Enterobacteriaceae, Pseudomonadaceae, Rhizobiaceae, Streptomycetaceae or Nocardiaceae, especially preferably bacteria of the genera *Escherichia, Corynebacteria, Pseudomonas, Streptomyces, Nocardia, Burkholderia, Salmonella, Agrobacterium* or *Rhodococcus*. The species *Escherichia coli* or *Corynebacterium glutamicum* are very especially preferred. Further advantageous bacteria can furthermore be found in the group of the Gram-positive, alpha-Proteobacteria, beta-Proteobacteria or gamma-Proteobacteria, and further advantageous microorganisms in the genus *Saccharomyces*.

In the process according to the invention, the enzymes E and F can be expressed separately from each other in at least two different organisms. The simultaneous expression of the enzymes E and F in one organism is preferred.

The organism may already naturally express, as the wild type, the enzyme employed in the process according to the invention. It may be advantageous to increase the activity of the employed enzyme E and/or F in the organism. This can be achieved for example by overexpressing the enzyme by known or above-described recombinant DNA techniques, but, for example, also by mutagenesis, followed by screening methods of the organisms for increased activity.

It is possible to employ, in the process according to the invention, an organism which, as the wild type, does not express any enzyme to be employed, but which, with the aid of recombinant techniques, has been made capable of heterologously expressing a suitable enzyme.

In the process according to the invention, the expressed enzyme is preferably overexpressed homologously, the expressed enzyme is especially preferably overexpressed heterologously. This can be done with the aid of an expression cassette in which a suitable promoter has been fused to a suitable coding nucleotide sequence and to a terminator or polyadenylation signal. To this end, one employs customary recombination and cloning techniques as they are described for example in T. Maniatis, E. F. Fritsch and J. Sambrook, Molecular Cloning: A Laboratory Manual, Cold Spring Harbor Laboratory, Cold Spring Harbor, N.Y. (1989) and in T J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987). For expression, the recombinant nucleic acid construct or gene construct is inserted into a suitable host organism, advantageously into a host-specific vector, which makes possible the optimal expression of the genes in the host. Vectors are well known to a person skilled in the art and can be found for example in "Cloning Vectors" (Pouwels P. H. et al., Ed., Elsevier, Amsterdam-N.Y.-Oxford, 1985).

The expressed enzymes which are employed in the process according to the invention can be secreted or else expressed intracellularly by the produced organism.

In the process according to the invention, the transamination of the keto group and, if appropriate, the preceding oxidation of the hydroxyl group may take place during the culturing of the organism or else after culturing. The organism can be separated from the culture medium or else remain therein. In the case of the intracellular expression of the enzyme employed, it may be advantageous to disrupt the organism cells using methods known to a person skilled in the art, such as, for example, with detergents, a French press or a ball mill.

Owing to technical advantages of the process, it is preferred for the enzyme E and/or F to exert their catalytic function in the cell and for the process to be carried out continuously in the whole-cell catalyst.

In a further embodiment of the process according to the invention, the enzyme E and/or F is employed in purified form. Purification may be performed with known, above-described or chromatographic methods.

In this embodiment of the process according to the invention, the enzyme E and/or F may be present in immobilized form, for example coupled to latex spheres, or else free in solution. The preferred solvent in the process according to the invention is water.

The process according to the invention is advantageously carried out at a temperature between 0° C. to 95° C., preferably between 10° C. to 85° C., especially preferably between 15° C. to 75° C.

The pH in the process according to the invention is advantageously maintained at between pH 4 and 12, preferably between pH 5 and 10, especially preferably between pH 6 and 9. The process according to the invention can be carried out batchwise, semi-batchwise or continuously.

It may be advantageous to vary the reaction conditions, preferably the pH, during the enzymatic amination, that is to say process step B. In this manner, it is possible to influence, or adjust, the ratio of the formed enantiomers in the product. The process according to the invention is therefore preferably characterized in that the ratio of the formed enantiomers of the ring systems bearing at least one amino group is influenced by varying the reaction conditions, preferably the pH.

In the process according to the invention, the enzyme F and E can be used for oxidizing the hydroxyl group and for transaminating the keto group of the multicyclic ring system, and an enzyme G with amino acid dehydrogenase activity can simultaneously be employed for simultaneously regenerating the reduction equivalents. This principle of cofactor regeneration is illustrated in FIG. 1 with reference to examples of substances. In a further, preferred embodiment of the process according to the invention, therefore, the byproducts, such as, for example, reduction equivalents or amino group donors, which are generated by the enzymatic reactions of enzymes E and F are regenerated by using at least one enzyme G with amino acid dehydrogenase activity, such as, for example, alanine dehydrogenase, phenylalanine dehydrogenase, aspartate dehydrogenase and serine dehydrogenase, in particular glutamate dehydrogenase.

If a scyllo-inositol transaminases is employed in the process according to the invention, it is preferred additionally to employ the enzymes glutamine synthetase and w-amidase in order to regenerate glutamine, the amino group donor employed here.

Products of the Transamination

The invention furthermore relates to the products produced by the process according to the invention, that is the multicyclic ring systems bearing at least one amino group.

Preferably, the product prepared by the process according to the invention is an enantiomer mixture. The product prepared by the process according to the invention is especially preferably an enantiomer mixture comprising a ratio of diaminoisoidide (III) to diaminoisosorbide (II) of from 0.5 to 4, preferably from 0.8 to 3 and especially preferably from 1 to 2.

In the examples mentioned hereinbelow, the present invention is described by way of example without this being intended to be a limitation of the invention, whose use range can be seen from the entire description and the claims, to the embodiments mentioned in the examples.

Examples 1 to 3 hereinbelow describe the synthesis of the diamines (II)-(III) from hexodiulose (VII), the synthesis of the mixed diamines/diols (IX and X) from the monoketone (VIII)

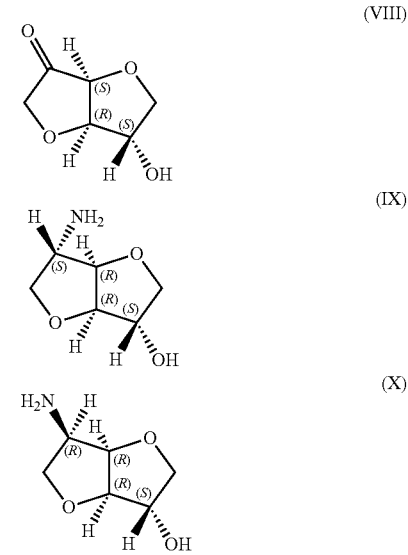

and
the synthesis of the diamines (II)-(III) directly from (V) and (IV).

EXAMPLES

Figure 2:
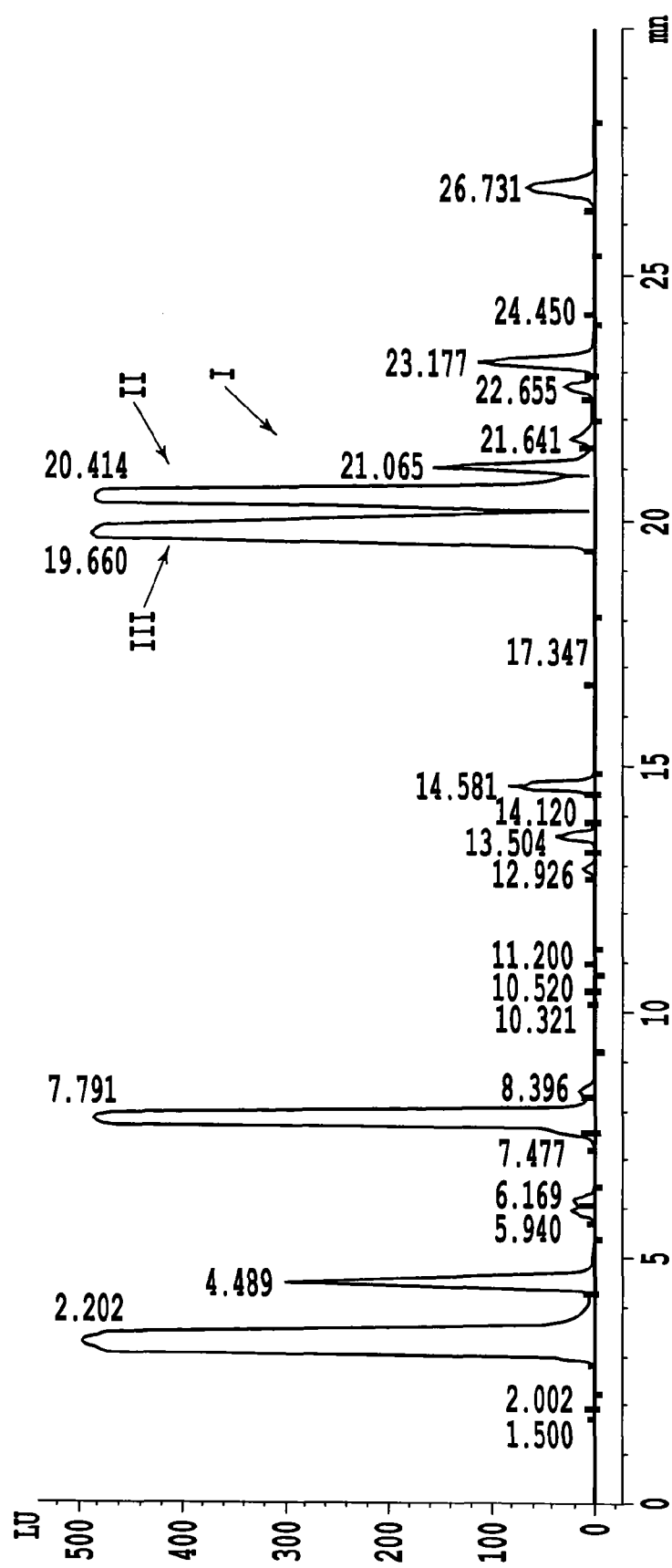
FIG. 2 shows the HPLC chromatogram of the standards diaminoisoidide (III) (0.5 g/l) and diaminoisosorbide (II) (0.5 g/l) and diaminoisomannitol (I).

The figures which follow illustrate the subject matter of the example:

FIG. 2 shows the HPLC chromatogram of the standards diaminoisoidide (III) (0.5 g/l) and diaminoisosorbide (II) (0.5 g/l) and diaminoisomannitol (I).

Figure 3:
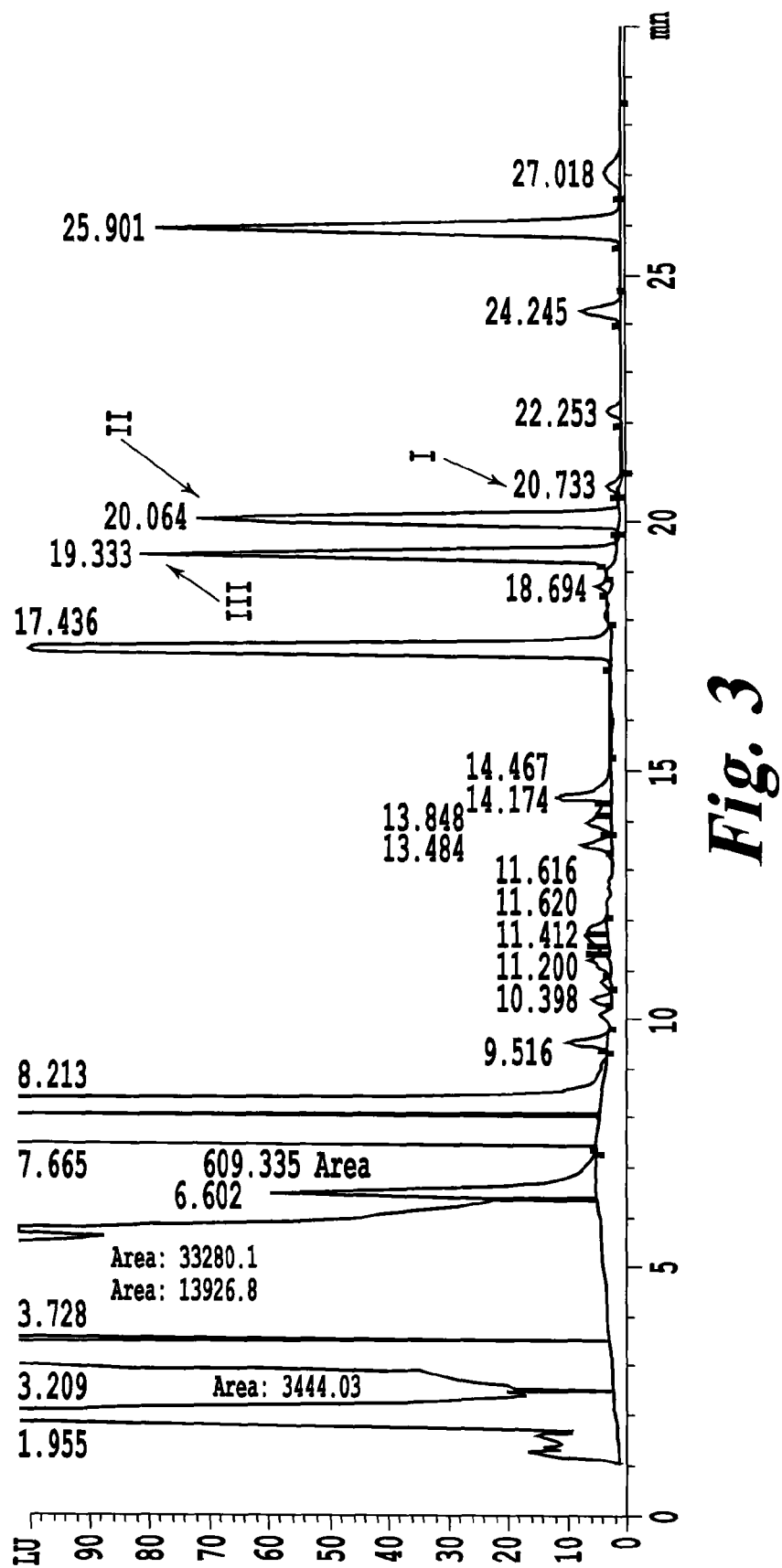
FIG. 3 shows the HPLC chromatogram of the reductive amination with the products diaminoisosorbide, diaminoisoidide and traces of diaminoisomannide at pH 7.2.

FIG. 3 shows the HPLC chromatogram of the reductive amination with the products diaminoisosorbide, diaminoisoidide and traces of diaminoisomannide at pH 7.2.

Figure 4:
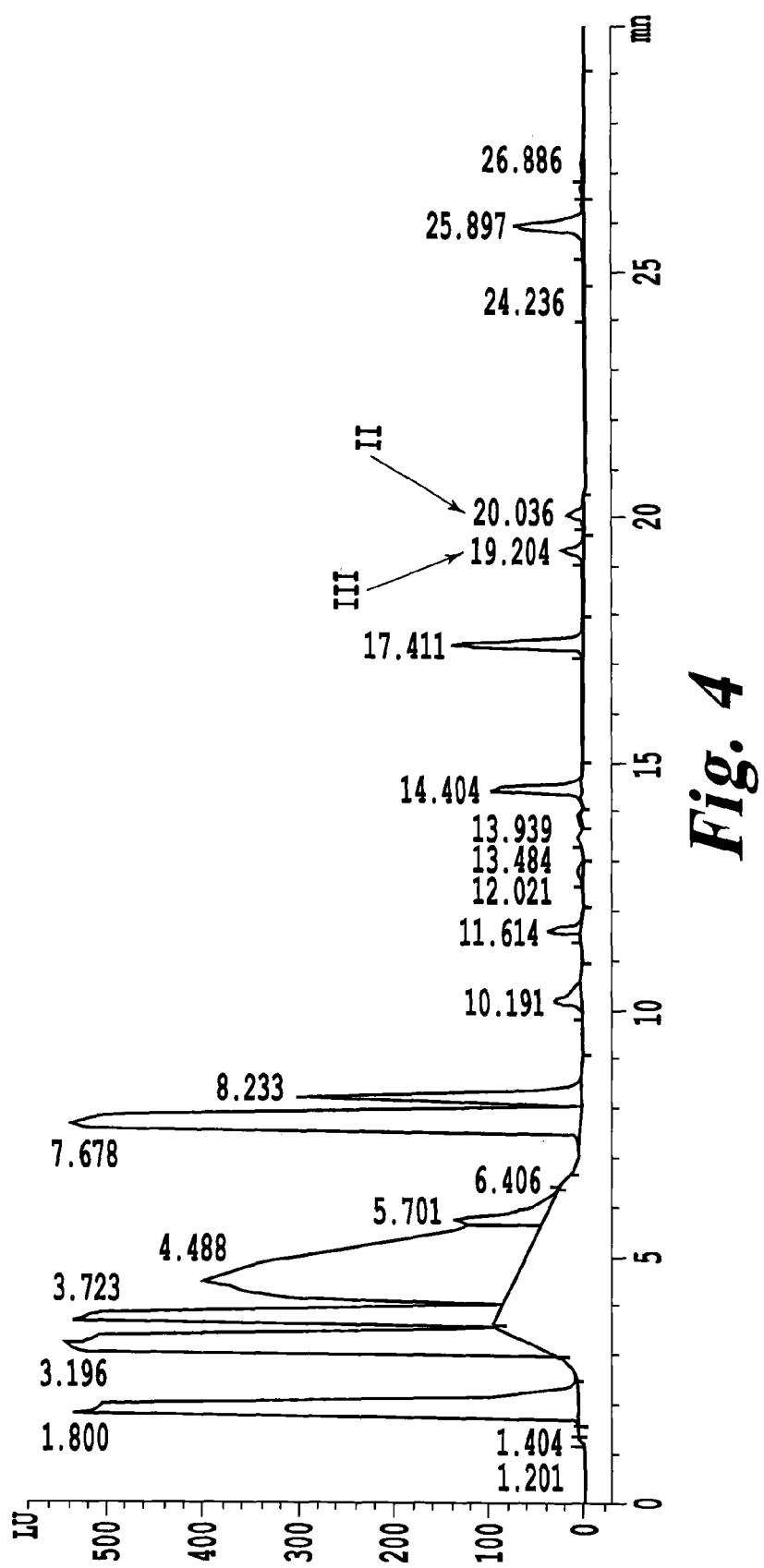
FIG. 4 shows the HPLC chromatogram of the separation of the reaction mixture of aminotransferase BtrR and diulose (VII) as substrate at pH 9.

FIG. 4 shows the HPLC chromatogram of the separation of the reaction mixture of aminotransferase BtrR and diulose (VII) as substrate at pH 9.

Figure 5:
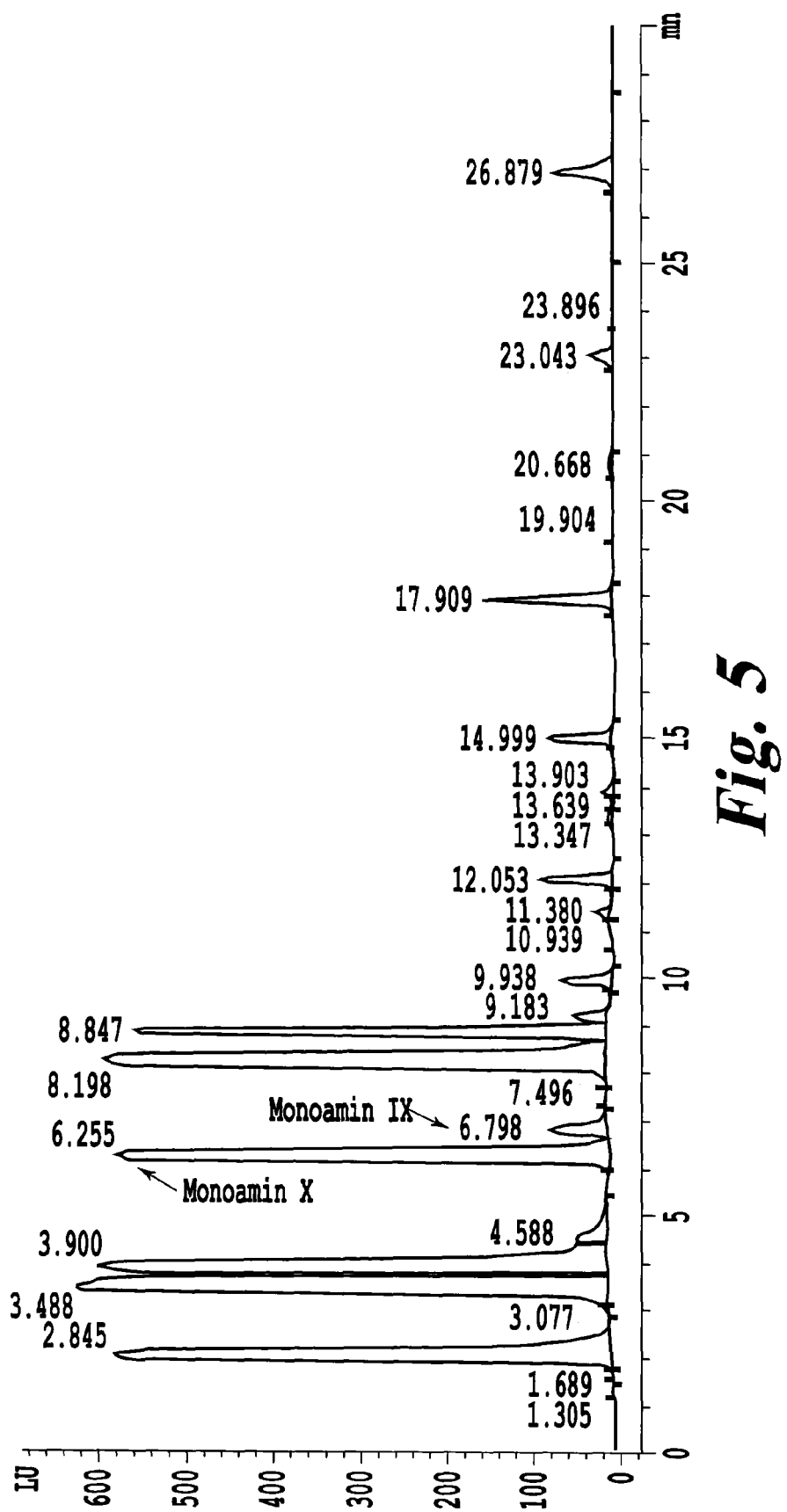
FIG. 5 shows the HPLC chromatogram of the separation of the reaction mixture of aminotransferase BtrR and monoketone (VIII) as substrate at pH 9.

FIG. 5 shows the HPLC chromatogram of the separation of the reaction mixture of aminotransferase BtrR and monoketone (VIII) as substrate at pH 9.

Figure 6:
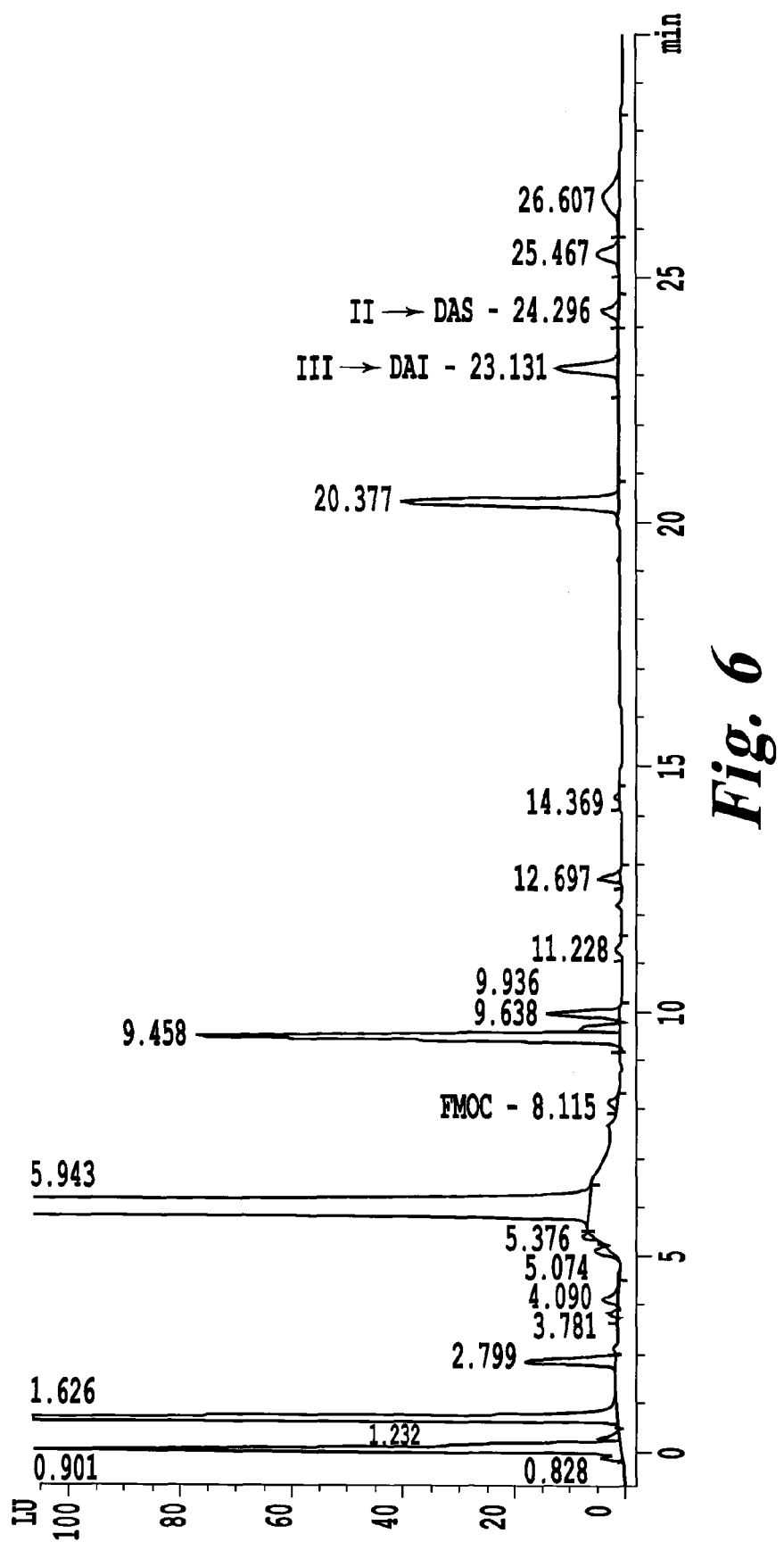
FIG. 6 shows the HPLC chromatogram of the separation of the reaction mixture of an aminotransferase from *Vibrio fluvialis* and diulose (VII) as the substrate.

FIG. 6 shows the HPLC chromatogram of the separation of the reaction mixture of an aminotransferase from *Vibrio fluvialis* and diulose (VII) as the substrate.

Figure 7:
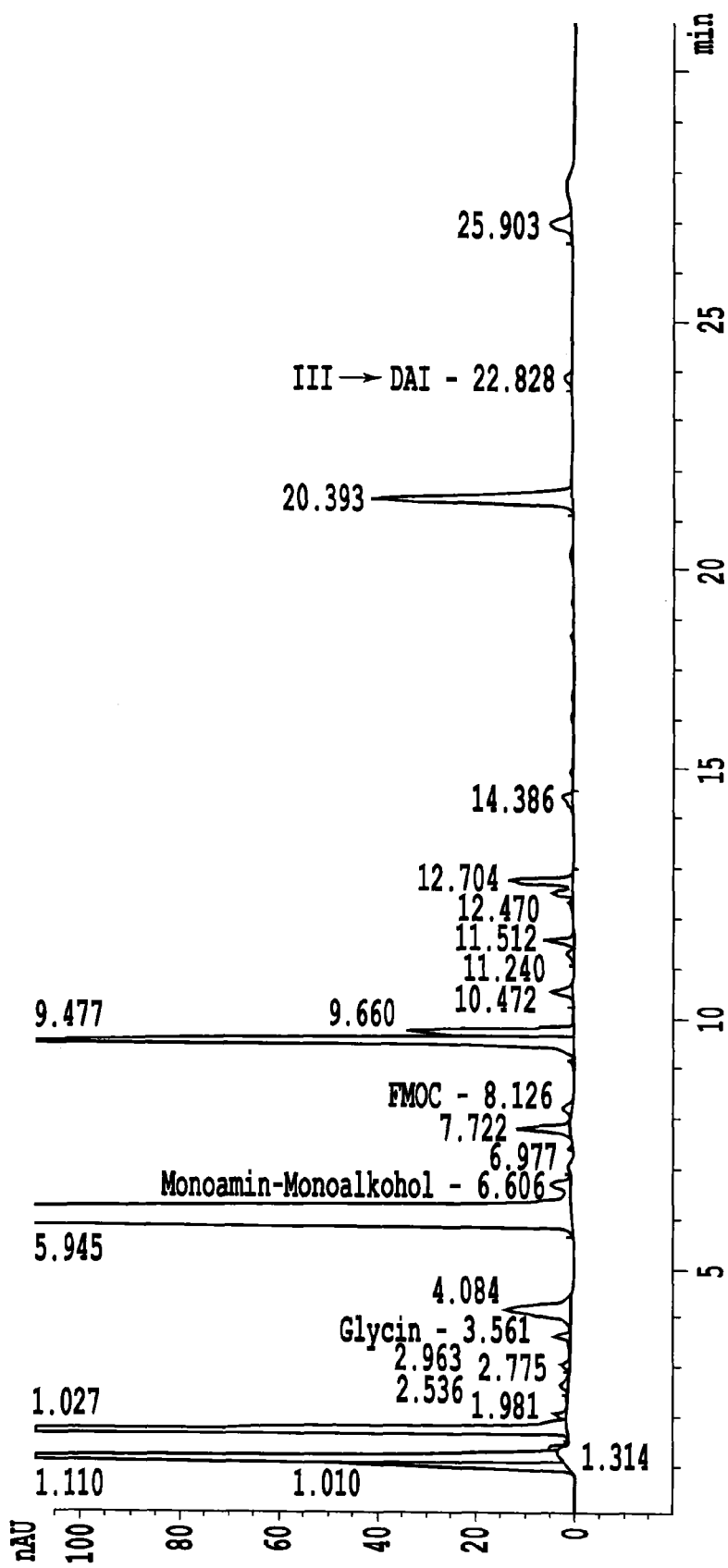
FIG. 7 shows the HPLC chromatogram of the separation of the reaction mixture of an aminotransferase from *Bacillus megaterium* and diulose (VII) as the substrate.

FIG. 7 shows the HPLC chromatogram of the separation of the reaction mixture of an aminotransferase from *Bacillus megaterium* and diulose (VII) as the substrate.

Figure 8:
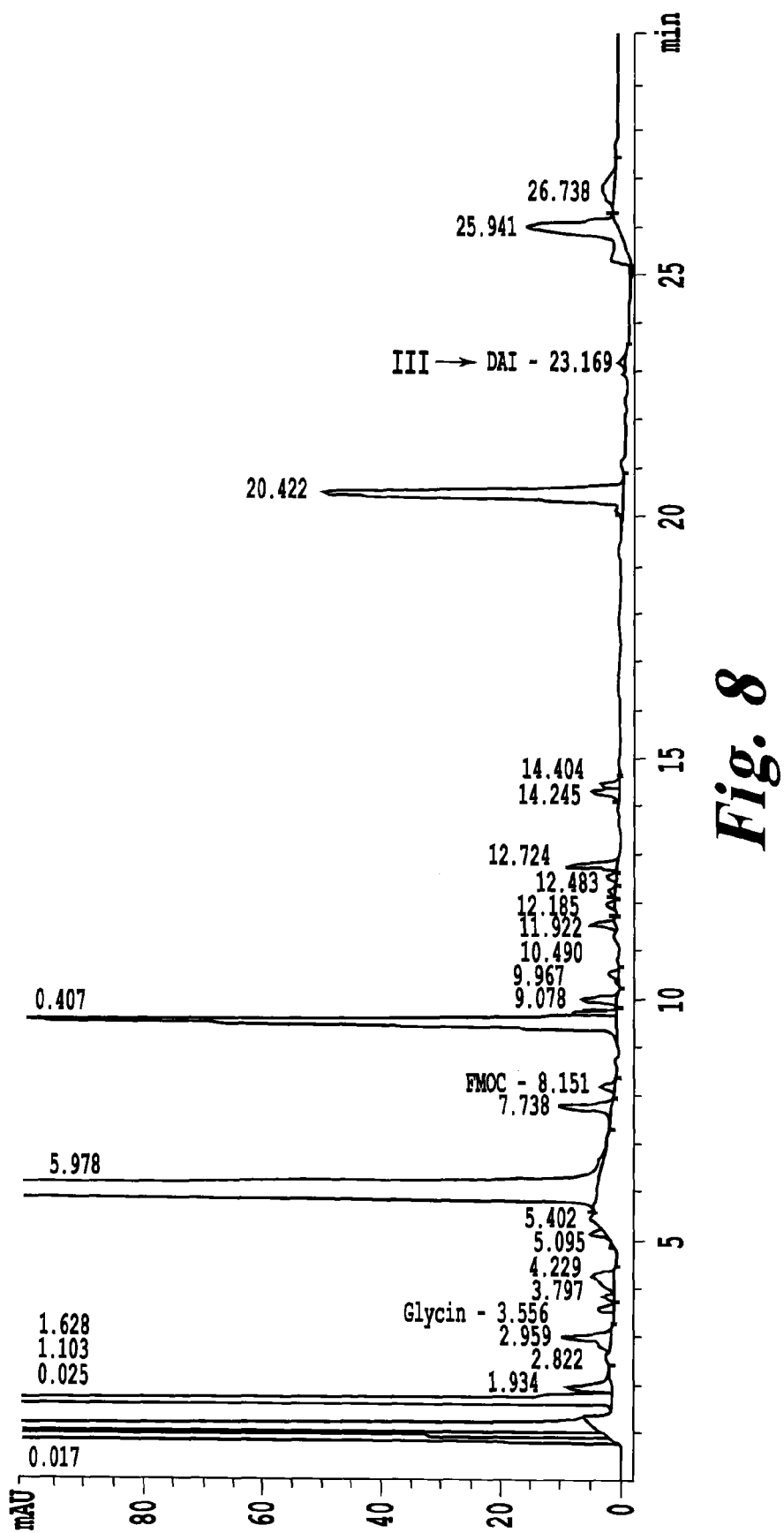
FIG. 8 shows the HPLC chromatogram of the separation of the reaction mixture of an aminotransferase from *Alcaligenes denitrificans* and diulose (VII) as the substrate.

FIG. 8 shows the HPLC chromatogram of the separation of the reaction mixture of an aminotransferase from *Alcaligenes denitrificans* and diulose (VII) as the substrate.

Figure 9:
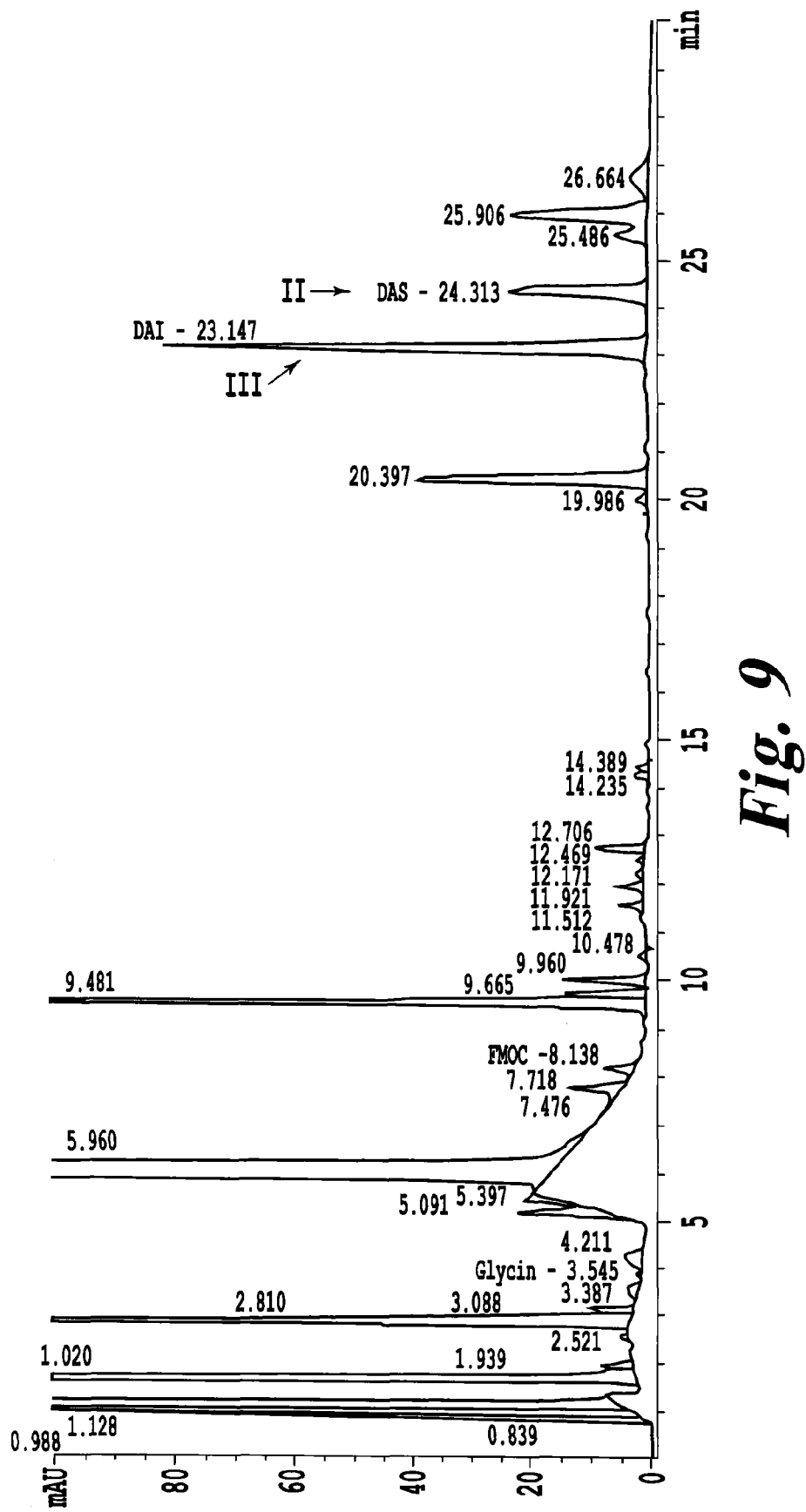
FIG. 9 shows the HPLC chromatogram of the separation of the reaction mixture of an aminotransferase from *Chromobacterium violaceum* and diulose (VII) as the substrate.

FIG. 9 shows the HPLC chromatogram of the separation of the reaction mixture of an aminotransferase from *Chromobacterium violaceum* and diulose (VII) as the substrate.

Figure 10:
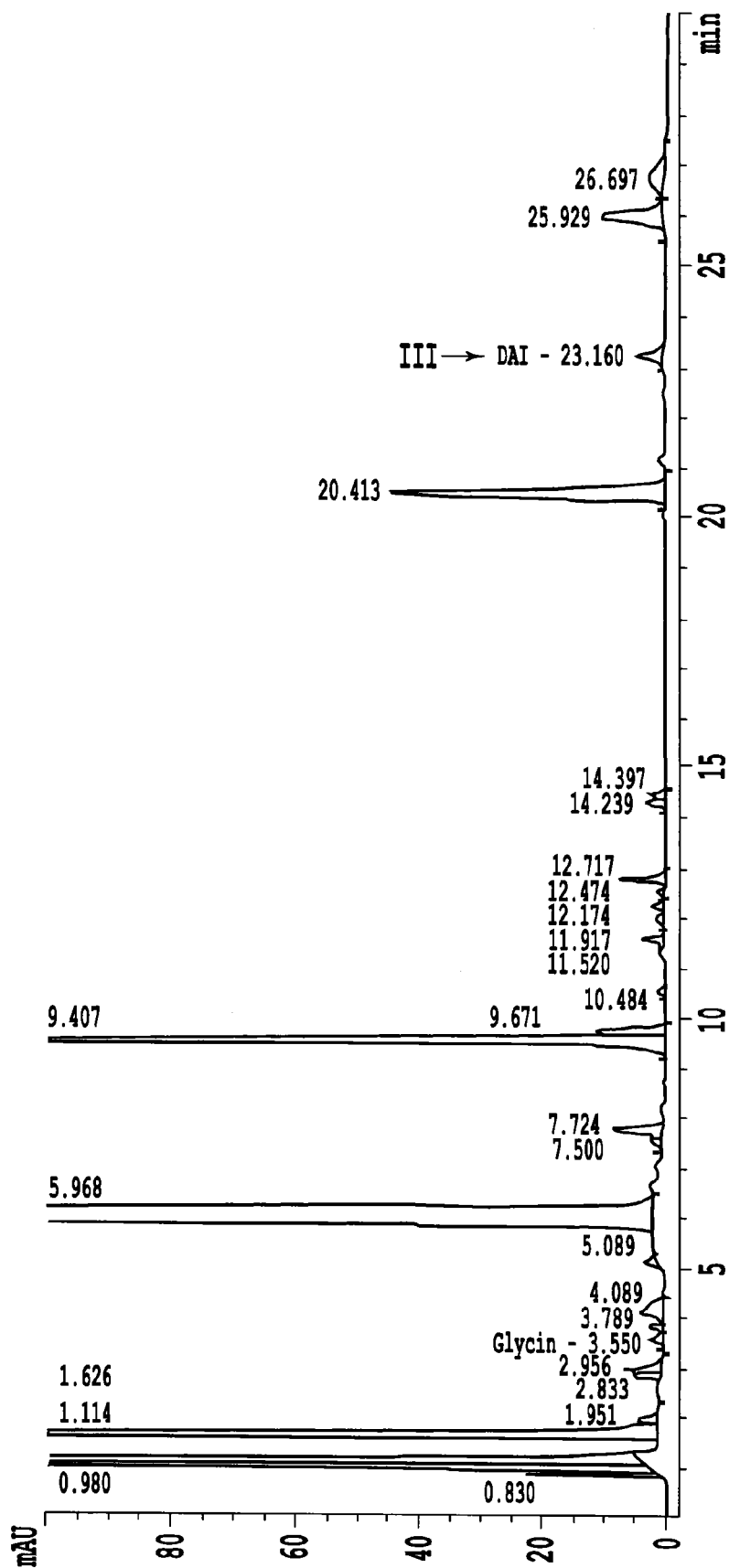
FIG. 10 shows the HPLC chromatogram of the separation of the reaction mixture of an aminotransferase from *Anthrobacter* sp. and diulose (VII) as the substrate.

FIG. 10 shows the HPLC chromatogram of the separation of the reaction mixture of an aminotransferase from *Anthrobacter* sp. and diulose (VII) as the substrate.

Figure 11:
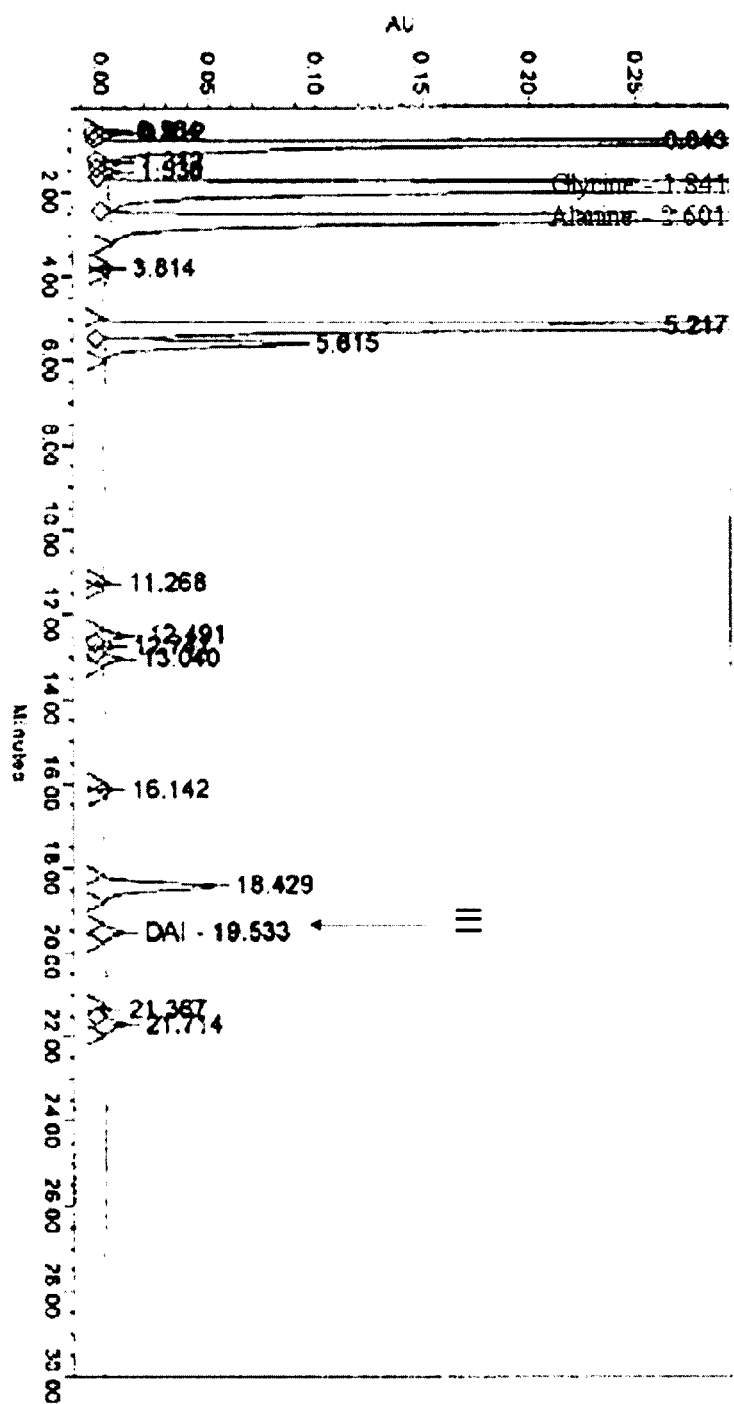
FIG. 11 shows the HPLC chromatogram of the separation of the reaction mixture of an aminotransferase from *Vibrio fluvialis* and diulose (VII) as the substrate.

FIG. 11 shows the HPLC chromatogram of the separation of the reaction mixture of an aminotransferase from *Vibrio fluvialis* and diulose (VII) as the substrate.

Figure 12:
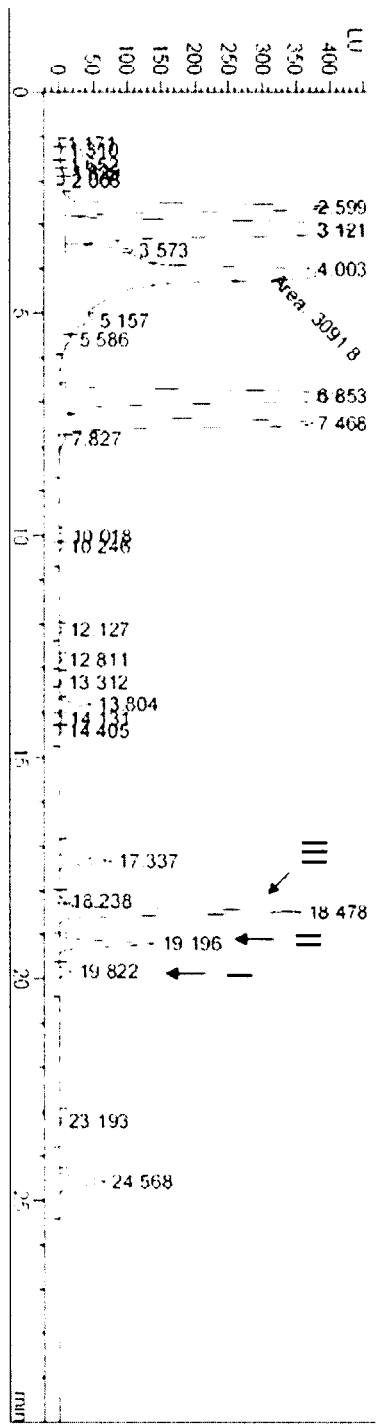
FIG. 12 shows the HPLC chromatogram of the separation of the reaction mixture of an aminotransferase from *Pseudomonas putida* and diulose (VII) as the substrate.

FIG. 12 shows the HPLC chromatogram of the separation of the reaction mixture of an aminotransferase from *Pseudomonas putida* and diulose (VII) as the substrate.

Figure 13:
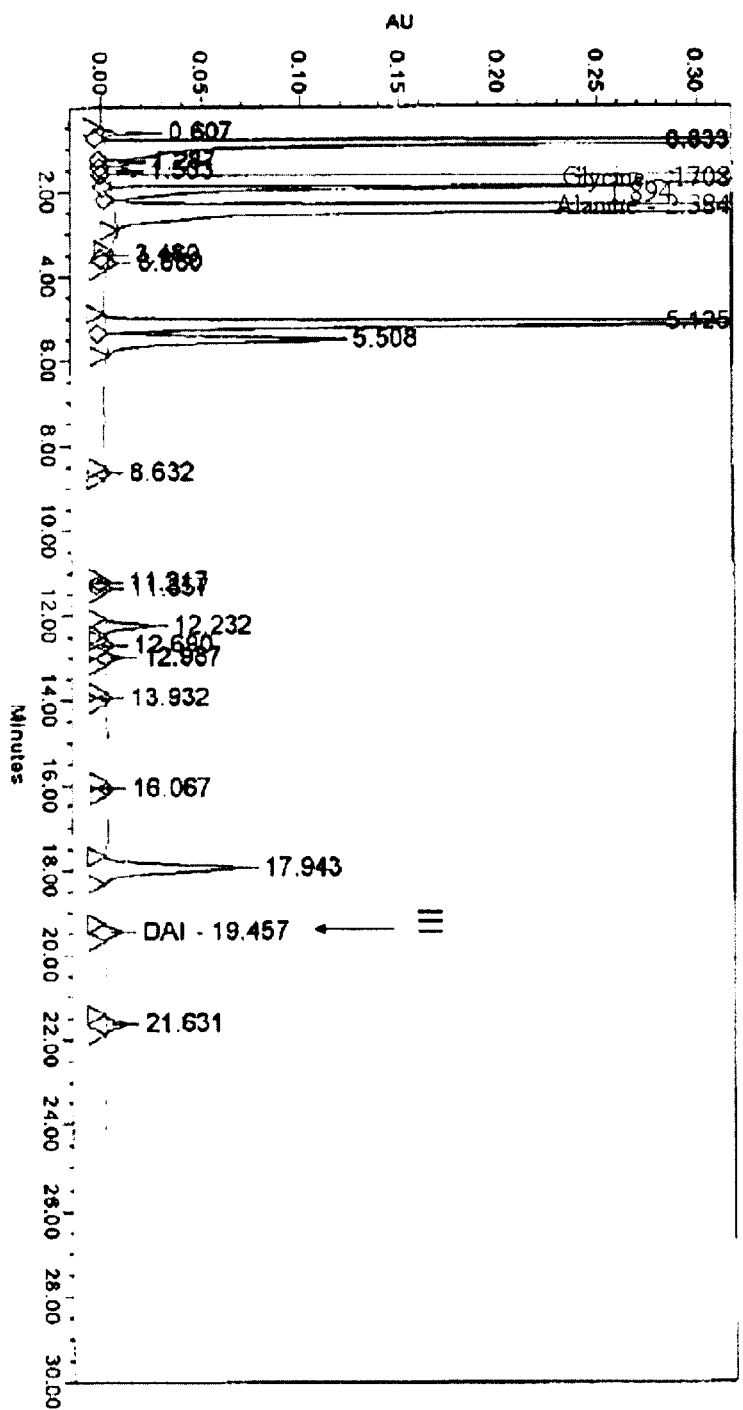
FIG. 13 shows the HPLC chromatogram of the separation of the reaction mixture of an aminotransferase from *Pseudomonas putida* and diulose (VII) as the substrate.

FIG. 13 shows the HPLC chromatogram of the separation of the reaction mixture of an aminotransferase from *Pseudomonas putida* and diulose (VII) as the substrate.

Figure 14:
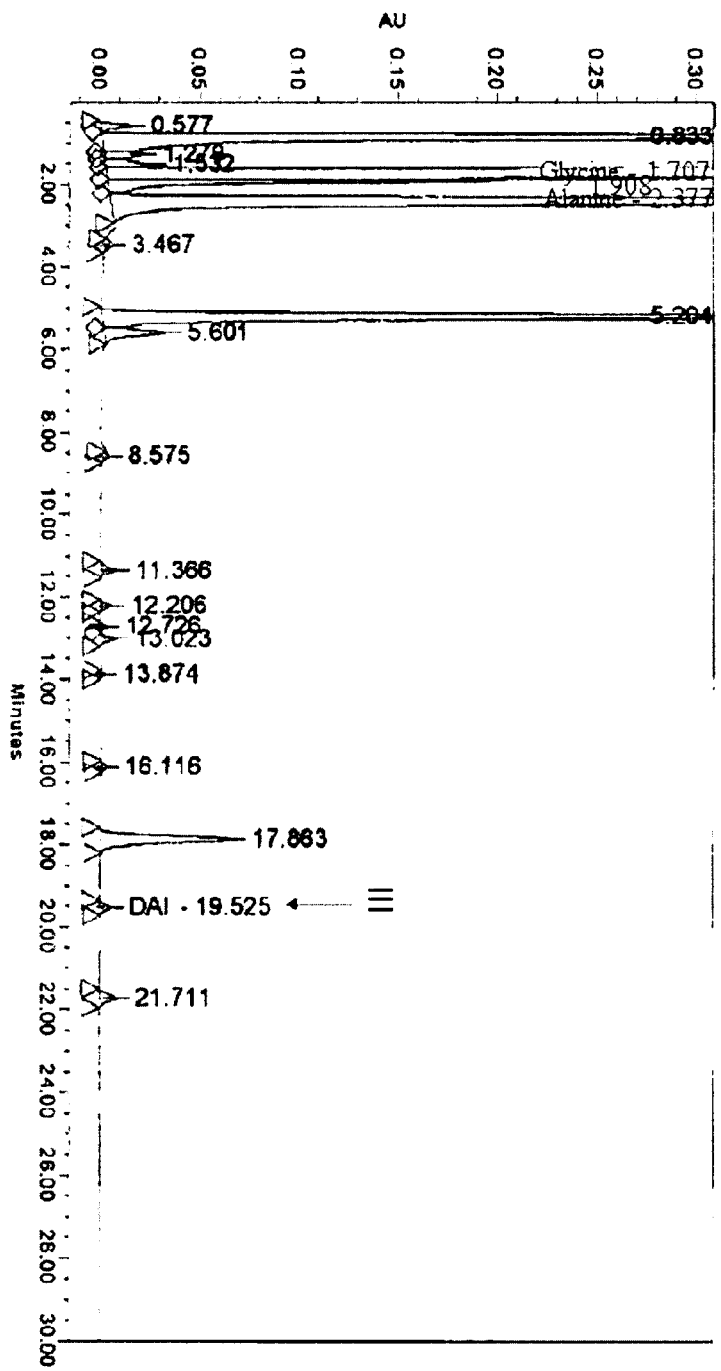
FIG. 14 shows the HPLC chromatogram of the separation of the reaction mixture of an aminotransferase from *Pseudomonas putida* and diulose (VII) as the substrate.

FIG. 14 shows the HPLC chromatogram of the separation of the reaction mixture of an aminotransferase from *Pseudomonas putida* and diulose (VII) as the substrate.

Figure 15:
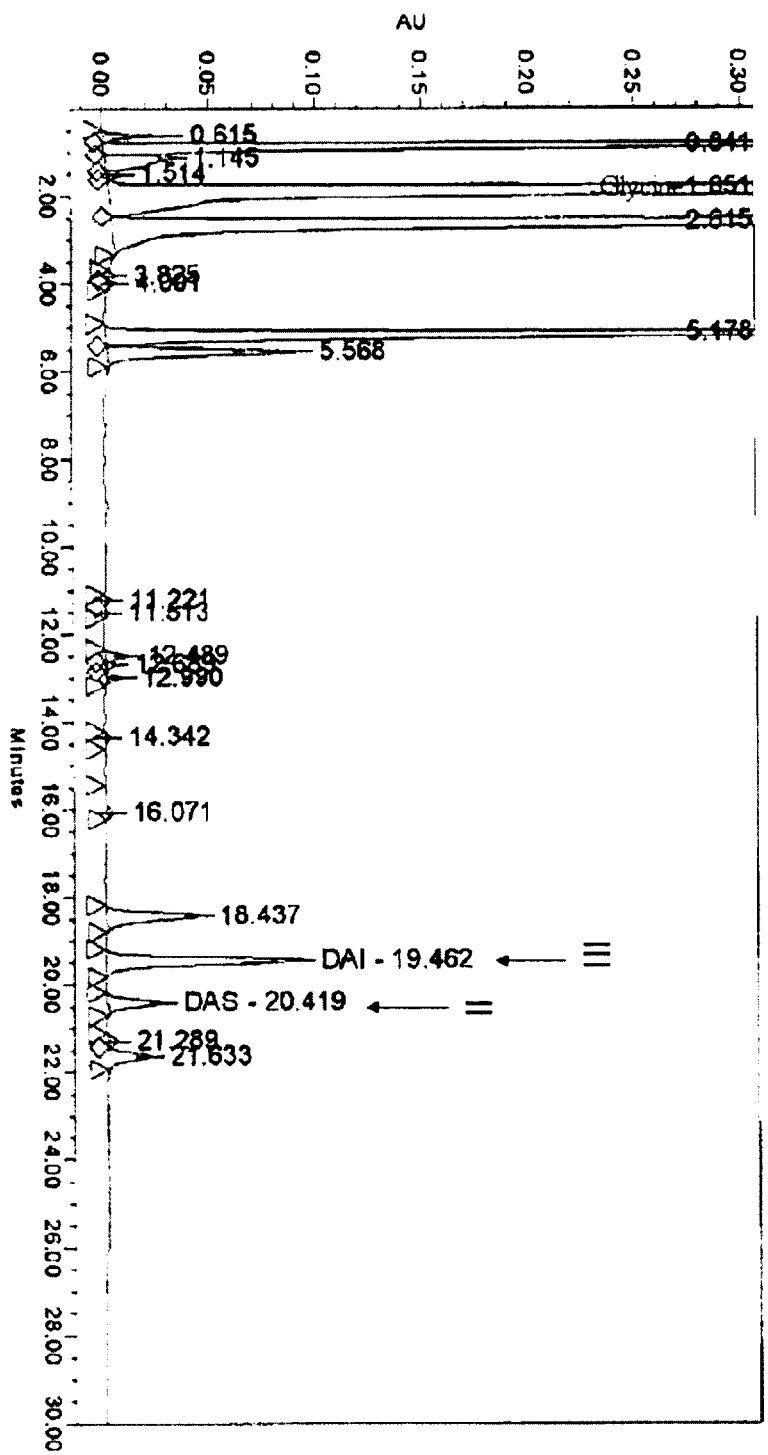
FIG. 15 shows the HPLC chromatogram of the separation of the reaction mixture of an aminotransferase from *Chromobacterium violaceum* and diulose (VII) as the substrate.

FIG. 15 shows the HPLC chromatogram of the separation of the reaction mixture of an aminotransferase from *Chromobacterium violaceum* and diulose (VII) as the substrate.

Figure 16:
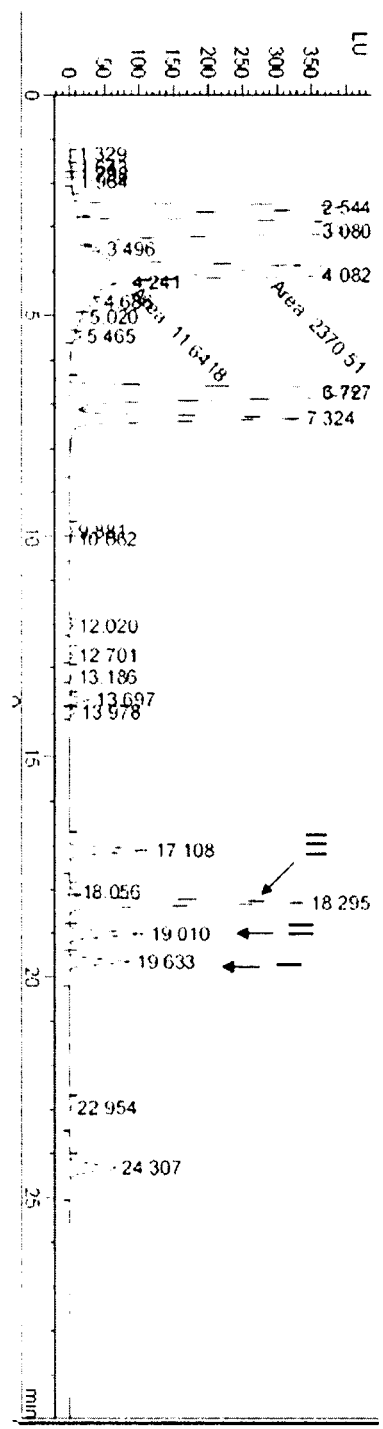
FIG. 16 shows the HPLC chromatogram of the separation of the reaction mixture of an aminotransferase from *Rhodobacter sphaeroides* and diulose (VII) as the substrate.

FIG. 16 shows the HPLC chromatogram of the separation of the reaction mixture of an aminotransferase from *Rhodobacter sphaeroides* and diulose (VII) as the substrate.

Figure 17:
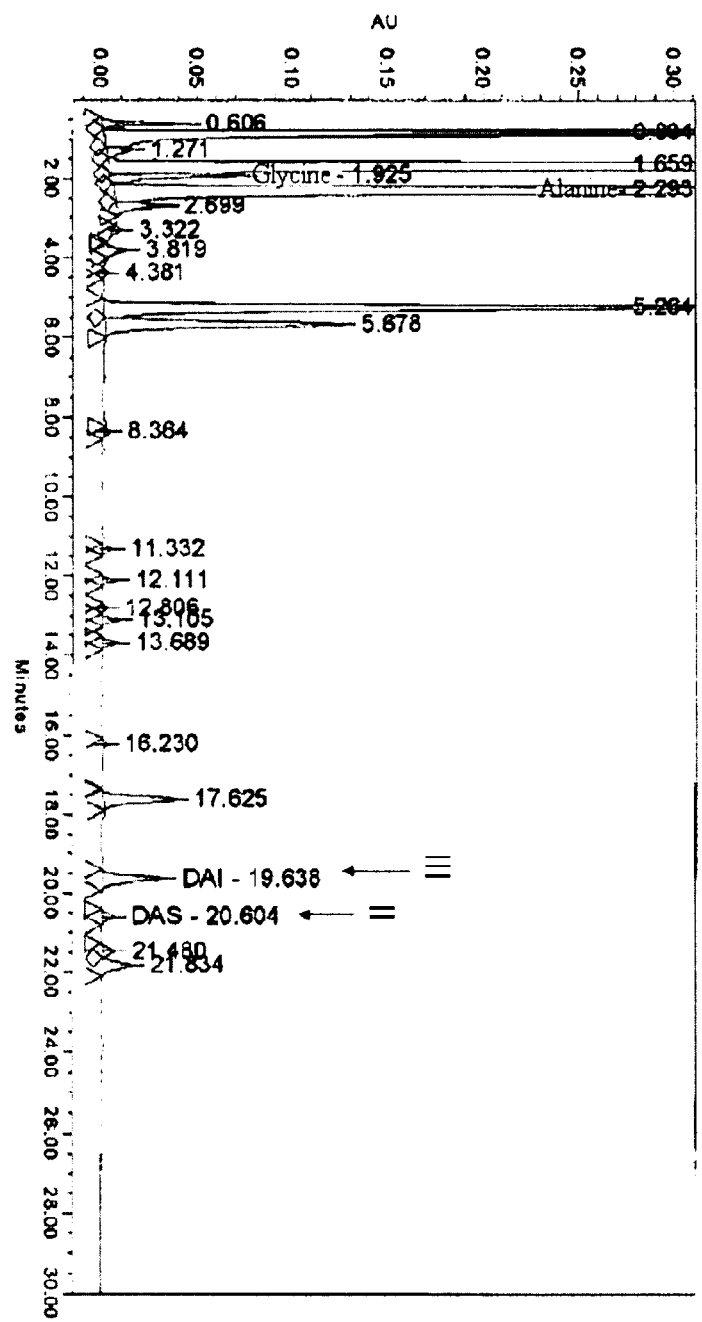
FIG. 17 shows the HPLC chromatogram of the separation of the reaction mixture of an aminotransferase from *Paracoccus denitrificans* and diulose (VII) as the substrate.

FIG. 17 shows the HPLC chromatogram of the separation of the reaction mixture of an aminotransferase from *Paracoccus denitrificans* and diulose (VII) as the substrate.

Figure 18:
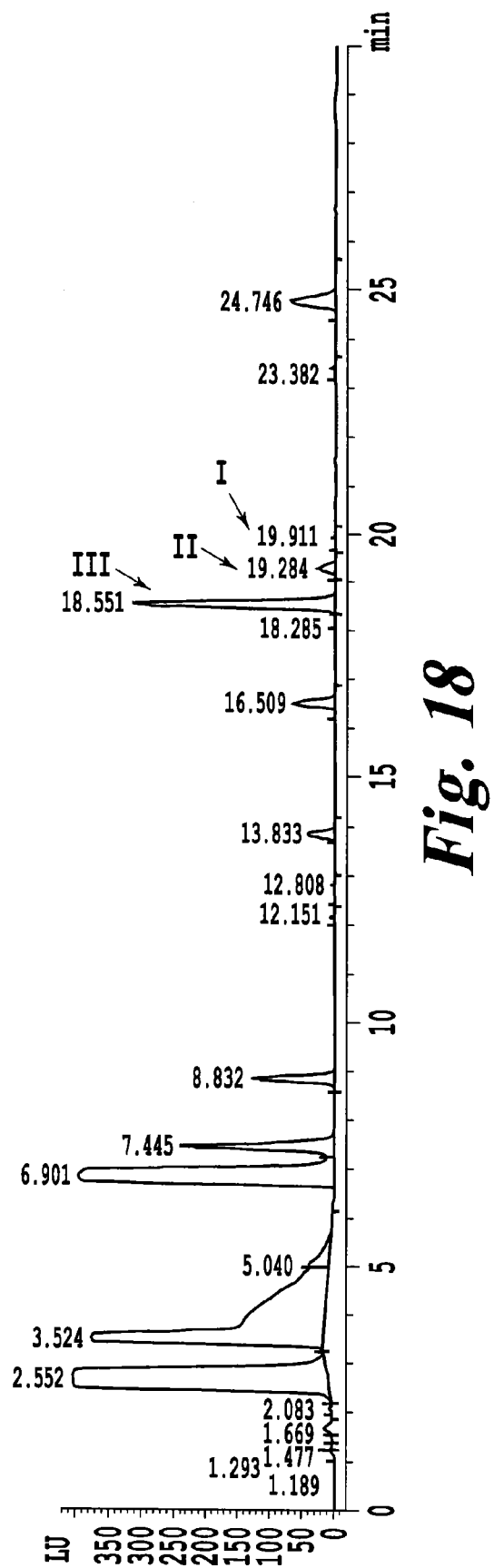
FIG. 18 shows the HPLC chromatogram of the separation of the reaction mixture of an aminotransferase from *Mesorhizobium loti* and diulose (VII) as the substrate.

FIG. 18 shows the HPLC chromatogram of the separation of the reaction mixture of an aminotransferase from *Mesorhizobium loti* and diulose (VII) as the substrate.

Figure 19:
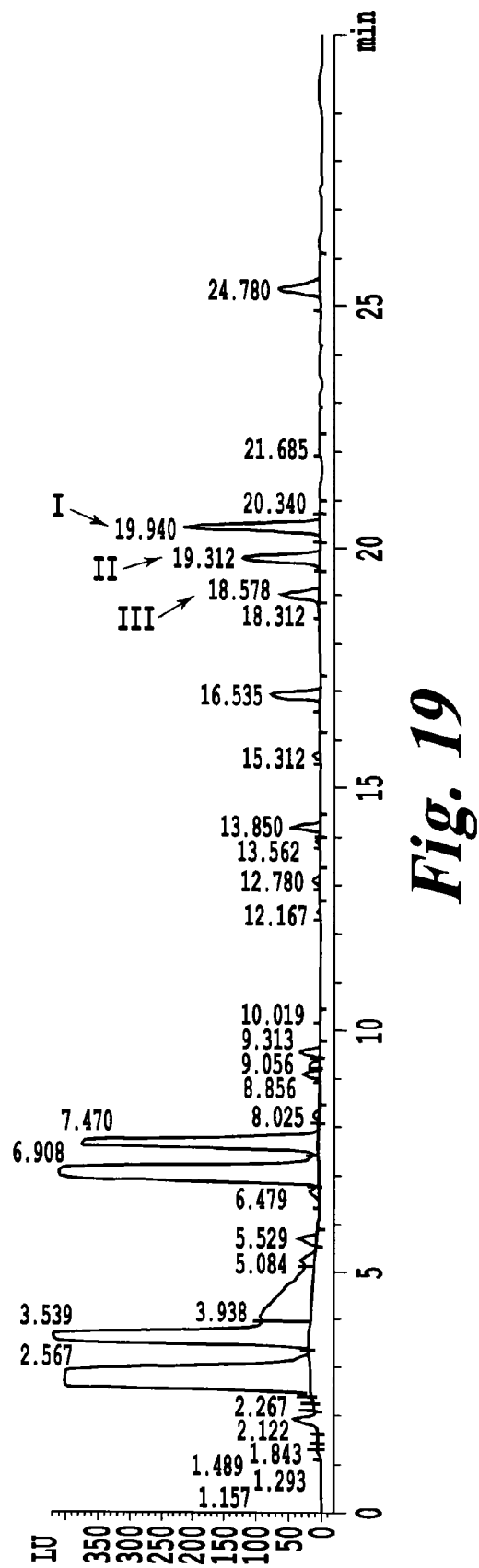
FIG. 19 shows the HPLC chromatogram of the separation of the reaction mixture of an aminotransferase from *Rhodobacter sphaeroides* and diulose (VII) as the substrate.

FIG. 19 shows the HPLC chromatogram of the separation of the reaction mixture of an aminotransferase from *Rhodobacter sphaeroides* and diulose (VII) as the substrate.

Example 1

Synthesis of Diaminoisosorbide (II) and Diaminoisoidide (III) Starting from Diulose (VII) Using the *Bacillus circulans* Aminotransferase BtrR The BtrR aminotransferase gene has been synthesized at Geneart, taking into consideration the codon usage of *Escherichia coli*, cf. SEQ ID NO: 5. In addition, the synthesized sequence received an EcoRI cleavage site at the 5' end and a PstI cleavage site at the 3' end (see appended sequence). The gene was provided integrated into the vector pGA4 (ampR). For cloning btrR into the vector pACYC-Duet-1, btrR was excised from pGA4 using the restriction enzymes EcoRI and PstI.

The ligation mixture of btrR and pACYC-Duet-1 was first cloned into *E. coli* DH5α and, after the sequencing of the gene had been checked, into the target organism *E. coli* BL21 (DE3). The recombinant plasmid is named pACYC-Duet1::btrR.

By cloning btrR into the MCS1 of pACYC-Duet1, a $(His)_6$-tag fusion is introduced at the N terminus of the protein.

To purify the protein BtrR-$(His)_6$, *E. coli* BL21 was cultured in LB medium. The expression of btrR was induced in the exponential growth phase OD 0.4-0.6 by adding IPTG (final concentration 1 mM). After an incubation period of 6 hours, the culture was harvested, and the cell pellet was disrupted with BugBuster reagent. The aminotransferase BtrR-$(His)_6$ was purified via Ni-chelate affinity chromatography (His-bind columns, Novagen), following the column manufacturer's instructions. The purified enzyme was employed directly in the diulose conversion enzyme assay. The products were subsequently detected via HPLC with FMOC derivatization.

The enzyme assay was composed as follows:

Composition of the Enzyme Assay

| Buffer and solutions | Final concentration in the mixture |
| --- | --- |
| 0.1M Tris-HCl buffer pH 9 or pH 7.2 | 50 mM |
| Diulose | 50 mM |
| L-Glutamine | 10 mM |
| Pyridoxal phosphate | 0.3 mM |
| Purified BtrR in 50 mM Tris-HCl | 80 µg |
| Total volume | 100 µl |

After an incubation period of 72 hours, the sample was filtered through a filtration unit with a 10 kDa exclusion size in order to remove the protein. A diaminoisoidide concentration of 8.46 mg/l and a diaminosorbide concentration of 6.3 mg/l were measured in the FMOC-HPLC. Under these conditions, the ratio of diaminoisoidide (III) to diaminoisosorbide (II) was 1.34. It was possible to shift the ratio (III):(II) towards an increased diaminoisoidide synthesis by lowering the pH. At a pH of 7.2, a diaminoisoidide:diaminoisosorbide ratio of 1.8 was obtained (2.28 g/l vs. 1.27 g/l).

FIG. 2 shows the chromatogram of the standards diaminoisoidide (0.5 g/l) and diaminoisosorbide (0.5 g/l).

FIG. 3 shows the separation of the reaction mixture of aminotransferase BtrR and diulose (VII) as substrate at pH 9, FIG. 4 the separation of the reaction mixture of aminotransferase BtrR and diulose (VII) as the substrate at pH 7.2.

The amination of diulose (VII) affords mostly the diamines (II) and (III) and only a very small amount of the diamine (I).

By varying the pH during the enzymatic amination, therefore, it was possible to modify the ratio between stereoisomer (II) and stereoisomer (III).

Example 2

Amination of the Monoketone (VIII) with the *B. circulans* Aminotransferase BtrR The enzyme assay is composed as described in example 1. Monoketone (VIII) at a final concentration of 50 mM is employed instead of diulose.

Composition of the Enzyme Assay

| Buffer and solutions | Final concentration in the mixture |
| --- | --- |
| 0.1M Tris-HCl buffer pH 9 | 50 mM |
| Monoketone (VIII) | 50 mM |
| L-Glutamine | 10 mM |
| Pyridoxal phosphate | 0.3 mM |
| Purified BtrR in 50 mM Tris-HCl | 400 µg |
| Total volume | 500 µl |

FIG. 5 shows the HPLC diagram of the separation of the reaction mixture of aminotransferase BtrR and monoketone (VIII) as substrate at pH 9. The amination of the monoketone (VIII) affords more (X) than (IX), analogously to example 1.

Example 3

Starting from Isosorbide, Conversion into the Diamine in a Coupled Reaction

To successfully convert isosorbide into the diamine, a reaction with cell extract from *Pichia guillermondii* and purified BtrR-His protein is set up. Besides the direct synthesis of isosorbide via diulose to give the diamine, the synthesis also proceeds via the intermediates monoketone-monoalcohol, monoamine-monoalcohol, monoamine-monoketone to give the diamine. The cell extract of *P. guillermondii* is prepared as follows: 0.43 g of moist cell biomass was resuspended in 1 ml 0.1 mol/l Tris/HCl buffer pH 7.2 in a reaction vessel (fill level 1.5 ml). To this cell suspension there were added 1 g of glass beads (diameter 0.25-0.3 mm), whereupon the cells were disrupted in a ball mill (Retsch) for 2×5 min at a frequency of 1/30 s. Before the second 5-min run, the reaction vessel was briefly placed on ice in order to dissipate frictional heat. The mixture was centrifuged for 10 min at 13200×g and the supernatant was removed carefully. After an incubation period of 72 hours, the samples are centrifuged in a table-top centrifuge using filter units with an exclusion size of 30 kDa. Pyruvate and L-lactate dehydrogenase are employed to avoid a back-reaction of the "isosorbide" dehydrogenase and to regenerate $NAD^+$.

The enzyme assay is composed as follows:

| Buffer and solutions | Final concentration in the mixture |
| --- | --- |
| 0.1M Tris-HCl buffer pH 8.2 | 50 mM |
| Pyruvate | 20 mM |
| $NAD^+$ | 1 mM |
| L-Lactate dehydrogenase | 50 U |
| Isosorbide | 10 mM |
| *P. guilliermondii* enzyme extract | 10% of the final volume (100 µl) |
| Pyridoxal phosphate | 0.3 mM |
| Purified BtrR in 50 mM Tris-HCl | 800 µg |
| Protease inhibitor (Sigma) | 10 µl |
| Total volume | 1 ml |

Using HPLC analysis, it is possible to identify the monoamine intermediates (IX) and (X) and the diamines (II) and (III). It was possible to oxidize isosorbide (V) and isomannide (IV) up to the diulose (VII) level. Using the recombinantly expressed transaminase, the oxidation product (diulose (VII)) was aminated to give the diamine (II) and (III), and the oxidation intermediates (for example the monoketone (VIII)) were aminated to give the monoamines (IX) and (X).

Thus, it was possible not only successfully to enzymatically oxidize the secondary hydroxyl groups of dianhydrohexitols both at the exo-position and at the endo-position, but the products of these reactions were also successfully enzymatically aminated. Here, it was possible to obtain amino groups both in exo and in endo position.

Example 4

Production of a *Vibrio fluvialis* Aminotransferase, and Amination of Diulose (VII) Using the Latter The *Vibrio fluvialis* aminotransferase gene (SEQ ID NO: 6) was synthesized at Geneart; here, the codon usage of *Escherichia coli* was taken into consideration. In addition, the synthesized sequence was provided with an NdeI cleavage site at the 5' end and with an XhoI cleavage site at the 3' end. The gene was delivered integrated into the vector pET21a.

The vector with the target gene was subsequently cloned into the target organism *E. coli* BL21 (DE3).

The expression of the aminotransferase gene was induced during the exponential growth phase at $OD_{600}$ 0.7 by adding IPTG (final concentration 1 mM). After an incubation period of 3 hours, the culture was harvested, and the cell pellet was lyophilized. Lyophilisate of 20 mg cells was first rehydrated in 100 mM sodium phosphate buffer (pH 7) and then employed directly in the diulose conversion enzyme assay. The products were subsequently detected via HPLC with FMOC derivatization.

The enzyme assay was composed as follows:

Composition of the Enzyme Assay

| Buffer and solutions | Final concentration in the mixture |
| --- | --- |
| 0.1M Na phosphate buffer pH 7 | 100 mM |
| Diulose | 50 mM |
| L-Alanine | 250 mM |
| Pyridoxal phosphate | 1 mM |
| Cell lyophilisate with aminotransferase | 20 mg |
| Total volume | 100 µl |

After an incubation period of 24 hours, the sample was filtered through a filter unit with an exclusion size of 10 kDa in order to remove the protein and the cell lysate. Thereafter, the mixture is measured by HPLC after first having been subjected to FMOC derivatization. FIG. 6 shows the HPLC chromatogram of the separation of the reaction mixture of a *Vibrio fluvialis* aminotransferase and diulose (VII) as the substrate.

Example 5

Production of a *Bacillus megaterium* Aminotransferase, and Amination of Diulose (VII) Using the Latter The gene of the *Bacillus megaterium* aminotransferase (SEQ ID NO: 8) was synthesized at Geneart; here, the codon usage of *Escherichia coli* was taken into consideration. In addition, the synthesized sequence was provided with an NdeI cleavage site at the 5' end and with an XhoI cleavage site at the 3' end. The gene was delivered integrated into the vector pET21a.

The vector with the target gene was subsequently cloned into the target organism *E. coli* BL21 (DE3).

The expression of the aminotransferase gene was induced during the exponential growth phase at $OD_{600}$ 0.7 by adding IPTG (final concentration 1 mM). After an incubation period of 3 hours, the culture was harvested, and the cell pellet was lyophilized. Lyophilisate of 20 mg cells was first rehydrated in 100 mM sodium phosphate buffer (pH 7) and then employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 50 mM |
| L-Alanine | 250 mM |
| Pyridoxal phosphate | 1 mM |
| Cell lyophilisate with aminotransferase | 20 mg |
| Total volume | 100 μl |

After an incubation period of 24 hours, the sample was filtered through a filter unit with an exclusion size of 10 kDa in order to remove the protein and the cell lysate. Thereafter, the mixture is measured by HPLC after first having been subjected to FMOC derivatization. FIG. 7 shows the HPLC chromatogram of the separation of the reaction mixture of a *Bacillus megaterium* aminotransferase and diulose (VII) as the substrate.

Example 6

Production of an *Alcaligenes* Denitrificans Aminotransferase, and Amination of Diulose (VII) Using the Latter The gene of the *Alcaligenes denitrificans* aminotransferase (SEQ ID NO: 10) was synthesized at Geneart; here, the codon usage of *Escherichia coli* was taken into consideration. In addition, the synthesized sequence was provided with an NdeI cleavage site at the 5' end and with an XhoI cleavage site at the 3' end. The gene was delivered integrated into the vector pET21a.

The vector with the target gene was subsequently cloned into the target organism *E. coli* BL21 (DE3).

The expression of the aminotransferase gene was induced during the exponential growth phase at $OD_{600}$ 0.7 by adding IPTG (final concentration 1 mM). After an incubation period of 3 hours, the culture was harvested, and the cell pellet was lyophilized. Lyophilisate of 20 mg cells was first rehydrogenated in 100 mM sodium phosphate buffer (pH 7) and then employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 50 mM |
| L-Alanine | 250 mM |
| Pyridoxal phosphate | 1 mM |
| Cell lyophilisate with aminotransferase | 20 mg |
| Total volume | 100 μl |

After an incubation period of 24 hours, the sample was filtered through a filter unit with an exclusion size of 10 kDa in order to remove the protein and the cell lysate. Thereafter, the mixture is measured by HPLC after first having been subjected to FMOC derivatization. FIG. 8 shows the HPLC chromatogram of the separation of the reaction mixture of an *Alcaligenes denitrificans* aminotransferase and diulose (VII) as the substrate.

Example 7

Production of a *Chromobacter Violaceum* Aminotransferase, and Amination of Diulose (VII) Using the Latter The gene of the *Chromobacter violaceum* aminotransferase (SEQ ID NO: 12) was synthesized at Geneart; here, the codon usage of *Escherichia coli* was taken into consideration. In addition, the synthesized sequence was provided with an NdeI cleavage site at the 5' end and with an XhoI cleavage site at the 3' end. The gene was delivered integrated into the vector pET21a.

The vector with the target gene was subsequently cloned into the target organism *E. coli* BL21 (DE3).

The expression of the aminotransferase gene was induced during the exponential growth phase at $OD_{600}$ 0.7 by adding IPTG (final concentration 1 mM). After an incubation period of 3 hours, the culture was harvested, and the cell pellet was lyophilized. Lyophilisate of 20 mg cells was first rehydrated in 100 mM sodium phosphate buffer (pH 7) and then employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 50 mM |
| L-Alanine | 250 mM |
| Pyridoxal phosphate | 1 mM |
| Cell lyophilisate with aminotransferase | 20 mg |
| Total volume | 100 μl |

After an incubation period of 24 hours, the sample was filtered through a filter unit with an exclusion size of 10 kDa in order to remove the protein and the cell lysate. Thereafter, the mixture is measured by HPLC after first having been subjected to FMOC derivatization. FIG. 9 shows the HPLC chromatogram of the separation of the reaction mixture of a *Chromobacterium violaceum* aminotransferase and diulose (VII) as the substrate.

Example 8

Production of an *Arthrobacter* sp. Aminotransferase, and Amination of Diulose (VII) Using the Latter The gene of the *Arthrobacter* sp. aminotransferase (SEQ ID NO: 14) was synthesized at Geneart; here, the codon usage of *Escherichia coli* was taken into consideration. In addition, the synthesized sequence was provided with an NdeI cleavage site at the 5' end and with an XhoI cleavage site at the 3' end. The gene was delivered integrated into the vector pET21a.

The vector with the target gene was subsequently cloned into the target organism *E. coli* BL21 (DE3).

The expression of the aminotransferase gene was induced during the exponential growth phase at $OD_{600}$ 0.7 by adding IPTG (final concentration 1 mM). After an incubation period of 3 hours, the culture was harvested, and the cell pellet was lyophilized. Lyophilisate of 20 mg cells was first rehydrated in 100 mM sodium phosphate buffer (pH 7) and then employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 50 mM |
| L-Alanine | 250 mM |
| Pyridoxal phosphate | 1 mM |
| Cell lyophilisate with aminotransferase | 20 mg |
| Total volume | 100 µl |

After an incubation period of 24 hours, the sample was filtered through a filter unit with an exclusion size of 10 kDa in order to remove the protein and the cell lysate. Thereafter, the mixture is measured by HPLC after first having been subjected to FMOC derivatization. FIG. 10 shows the HPLC chromatogram of the separation of the reaction mixture of an *Arthrobacter* sp. aminotransferase and diulose (VII) as the substrate.

Example 9

Production of a *Vibrio fluvialis* Aminotransferase, and Amination of Diulose (VII) Using the Latter The *Vibrio fluvialis* aminotransferase gene (SEQ ID NO: 16) was synthesized at Geneart. In addition, the synthesized sequence was provided with an NdeI cleavage site at the 5' end and with an HindIII cleavage site at the 3' end. The gene was integrated into the vector pOM17c.

The vector with the target gene was subsequently cloned into the target organism *E. coli* BL21 (DE3).

The expression of the aminotransferase gene was induced during the exponential growth phase at $OD_{500}$ 0.5 by adding IPTG (final concentration 1 mM). After an incubation period of 5 hours, the culture was harvested and centrifuged. After the cell pellet had been taken up in 100 mM sodium phosphate buffer (pH 7.0), the cells were disrupted by means of a ball mill, and the crude extract was obtained by a subsequent centrifugation. Thereafter, the crude extract was employed directly in the diulose conversion enzyme assay. The products were subsequently detected via HPLC with FMOC derivatization.

The enzyme assay had the following composition:
Composition of the Enzyme Assays

| Buffer and solutions | Final concentration in the mixture |
|---|---|
| 0.1M Na phosphate buffer pH 7 | 100 mM |
| Diulose | 5 mM |
| L-Alanine | 45 mM |
| Pyridoxal phosphate | 0.9 mM |
| Crude extract | 500 µl |
| Total volume | 1500 µl |

After an incubation period of 24 hours, the reaction was stopped, and the mixture was first subjected to FMOC derivatization and then measured by HPLC. FIG. 11 shows the HPLC chromatogram of the separation of the reaction mixture of a *Vibrio fluvialis* aminotransferase and with diulose (VII) as the substrate.

Example 10

Production of a *Pseudomonas putida* Aminotransferase, and Amination of Diulose (VII) Using the Latter The gene (SEQ ID NO: 18) of the aminotransferase was amplified from genomic *Pseudomonas putida* DNA and subsequently cloned into a pASK-IBA5+ vector with N-terminal Strep tag II with removal of the start ATG of the aminotransferase gene. The cleavage sites EheI and HindIII were used for this purpose.

The vector with the target gene was subsequently employed for transforming the target organism *E. coli* BL21.

The expression of the aminotransferase was induced during the exponential growth phase at $OD_{550}$ 0.5 by adding 0.2 µg/ml AHT. After an induction period of 3 hours, the culture was harvested, taken up in 25 mM Hepes/NaOH, pH 8.3, and the cells were disrupted by means of French press. Thereafter, the Strep-tag-II-fused aminotransferase was purified by means of streptavidin-sepharose and dialyzed overnight against 25 mM Hepes/NaOH, pH 8.3. The purified enzyme was then employed directly in the diulose transamination enzyme assay.

The enzyme assay was composed as follows:
Composition of the Enzyme Assay

| Buffer and solutions | Final concentration in the mixture |
|---|---|
| Hepes/NaOH buffer pH 8.3 | 25 mM |
| Diulose | 25 mM |
| L-Alanine | 8 mM |
| Pyridoxal phosphate | 0.3 mM |
| Purified enzyme | 10 µM |
| Total volume | 250 µl |

Thereafter, the mixture was first subjected to FMOC derivatization and then measured by HPLC. FIG. 12 shows the HPLC chromatogram of the separation of the reaction mixture of the enzymatic conversion of diulose (VII) by a *Pseudomonas putida* aminotransferase.

Example 11

Production of a *Pseudomonas putida* Aminotransferase, and Amination of Diulose (VII) Using the Latter The *Pseudomonas putida* aminotransferase gene (SEQ ID NO: 20) was cloned from genomic DNA. In addition, the cloned sequence was provided with an NdeI cleavage site at the 5' end and with an XhoI cleavage site at the 3' end. The gene was integrated into the vector pET21a(+).

The vector with the target gene was subsequently cloned into the target organism *E. coli* BL21 (DE3).

The expression of the aminotransferase gene was induced during the exponential growth phase at $OD_{600}$ 0.5 by adding IPTG (final concentration 1 mM). After an incubation period of 5 hours, the culture was harvested and centrifuged. After the cell pellet had been taken up in 100 mM sodium phosphate buffer (pH 7.0), the cells were disrupted by means of a ball mill, and the crude extract was obtained by subsequent centrifugation. The crude extract was subsequently employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 5 mM |
| L-Alanine | 45 mM |
| Pyridoxal phosphate | 0.9 mM |
| Crude extract | 500 µl |
| Total volume | 1500 µl |

After an incubation period of 24 hours, the reaction was stopped and the mixture was first subjected to FMOC derivatization and then measured by means of HPLC. FIG. 13 shows the HPLC chromatogram of the separation of the reaction mixture of a *Pseudomonas putida* aminotransferase and with diulose (VII) as the substrate.

Example 12

Production of a *Pseudomonas putida* Aminotransferase, and Amination of Diulose (VII) Using the Latter The *Pseudomonas putida* aminotransferase gene (SEQ ID NO: 22) was cloned from genomic DNA. In addition, the cloned sequence was provided with an NdeI cleavage site at the 5' end and with an XhoI cleavage site at the 3' end. The gene was integrated into the vector pET21a(+).

The vector with the target gene was subsequently cloned into the target organism *E. coli* BL21 (DE3).

The expression of the aminotransferase gene was induced during the exponential growth phase at $OD_{600}$ 0.5 by adding IPTG (final concentration 1 mM). After an incubation period of 5 hours, the culture was harvested and centrifuged. After the cell pellet had been taken up in 100 mM sodium phosphate buffer (pH 7.0), the cells were disrupted by means of a ball mill, and the crude extract was obtained by subsequent centrifugation. The crude extract was subsequently employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 5 mM |
| L-Alanine | 45 mM |
| Pyridoxal phosphate | 0.9 mM |
| Crude extract | 500 µl |
| Total volume | 1500 µl |

After an incubation period of 24 hours, the reaction was stopped and the mixture was first subjected to FMOC derivatization and then measured by means of HPLC. FIG. 14 shows the HPLC chromatogram of the separation of the reaction mixture of a *Pseudomonas putida* aminotransferase and with diulose (VII) as the substrate.

Example 13

Production of a *Chromobacterium violaceum* Aminotransferase, and Amination of Diulose (VII) Using the Latter The *Chromobacterium violaceum* aminotransferase gene (SEQ ID NO: 24) was cloned from genomic DNA. In addition, the cloned sequence was provided with an NdeI cleavage site at the 5' end and with an XhoI cleavage site at the 3' end. The gene was integrated into the vector pET29a.

The vector with the target gene was subsequently cloned into the target organism *E. coli* BL21 (DE3).

The expression of the aminotransferase gene was induced during the exponential growth phase at $OD_{600}$ 0.5 by adding IPTG (final concentration 1 mM). After an incubation period of 5 hours, the culture was harvested and centrifuged. After the cell pellet had been taken up in 100 mM sodium phosphate buffer (pH 7.0), the cells were disrupted by means of a ball mill, and the crude extract was obtained by subsequent centrifugation. The crude extract was subsequently employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 5 mM |
| L-Alanine | 45 mM |
| Pyridoxal phosphate | 0.9 mM |
| Crude extract | 500 µl |
| Total volume | 1500 µl |

After an incubation period of 24 hours, the reaction was stopped and the mixture was first subjected to FMOC derivatization and then measured by means of HPLC. FIG. 15 shows the HPLC chromatogram of the separation of the reaction mixture of a *Chromobacterium violaceum* aminotransferase and with diulose (VII) as the substrate.

Example 14

Production of a *Rhodobacter sphaeroides* Aminotransferase, and Amination of Diulose (VII) Using the Latter The gene (SEQ ID NO: 26) of the aminotransferase was amplified from genomic *Rhodobacter sphaeroides* DNA and subsequently cloned into a pASK-IBA5+ vector with N-terminal Strep tag II with removal of the start ATG of the aminotransferase gene. The cleavage sites EheI and HindIII were used for this purpose. The vector with the target gene was subsequently employed for transforming the target organism *E. coli* BL21.

The expression of the aminotransferase was induced during the exponential growth phase at $OD_{550}$ 0.5 by adding 0.2 µg/ml AHT. After an induction period of 3 hours, the culture was harvested, taken up in 25 mM Hepes/NaOH, pH 8.3, and the cells were disrupted by means of French press. Thereafter, the Strep-tag-II-fused aminotransferase was purified by means of streptavidin-sepharose and dialyzed overnight against 25 mM Hepes/NaOH, pH 8.3. The purified enzyme was then employed directly in the diulose transamination assay.

The enzyme assay was composed as follows:
Composition of the Enzyme Assay

| Buffer and solutions | Final concentration in the mixture |
|---|---|
| Hepes/NaOH buffer pH 8.3 | 25 mM |
| Diulose | 25 mM |
| L-Alanine | 8 mM |
| Pyridoxal phosphate | 0.3 mM |
| Purified enzyme | 10 μM |
| Total volume | 250 μl |

Thereafter, the mixture was first subjected to FMOC derivatization and then measured by HPLC. FIG. 16 shows the HPLC chromatogram of the separation of the reaction mixture of the enzymatic conversion of diulose (VII) by a *Rhodobacter sphaeroides* aminotransferase.

Example 15

Production of a *Paracoccus denitrificans* Aminotransferase, and Amination of Diulose (VII) Using the Latter The *Paracoccus denitrificans* aminotransferase gene (SEQ ID NO: 28) was cloned from genomic DNA. In addition, the cloned sequence was provided with an NdeI cleavage site at the 5' end and with an XhoI cleavage site at the 3' end. The gene was integrated into the vector pET21a(+).

The vector with the target gene was subsequently cloned into the target organism *E. coli* BL21 (DE3).

The expression of the aminotransferase gene was induced during the exponential growth phase at $OD_{600}$ 0.5 by adding IPTG (final concentration 1 mM). After an incubation period of 5 hours, the culture was harvested and centrifuged. After the cell pellet had been taken up in 100 mM sodium phosphate buffer (pH 7.0), the cells were disrupted by means of a ball mill, and the crude extract was obtained by subsequent centrifugation. The crude extract was subsequently employed directly in the diulose conversion enzyme assay. The products were subsequently detected via HPLC with FMOC derivatization.

The enzyme assay was composed as follows:
Composition of the Enzyme Assay

| Buffer and solutions | Final concentration in the mixture |
|---|---|
| 0.1M Na phosphate buffer pH 7 | 100 mM |
| Diulose | 5 mM |
| L-Alanine | 45 mM |
| Pyridoxal phosphate | 0.9 mM |
| Crude extract | 500 μl |
| Total volume | 1500 μl |

After an incubation period of 24 hours, the reaction was stopped and the mixture was first subjected to FMOC derivatization and then measured by means of HPLC. FIG. 17 shows the HPLC chromatogram of the separation of the reaction mixture of a *Paracoccus denitrificans* aminotransferase and with diulose (VII) as the substrate.

Example 16

Production of a *Mesorhizobium loti* Aminotransferase, and Amination of Diulose (VII) Using the Latter The gene (SEQ ID NO: 30) of the aminotransferase was amplified from genomic *Mesorhizobium loti* DSM2626 DNA and subsequently inserted into a pASK-IBA35+ vector with N-terminal $His_6$ tag with removal of the N-terminal ATG of the aminotransferase gene. The cleavage sites EheI and KpnI were used for this purpose.

The vector with the target gene was subsequently employed for transforming the target organism *E. coli* BL21.

The expression of the aminotransferase was induced during the exponential growth phase at $OD_{550}$ 0.5 by adding 0.2 μg/ml AHT. After an induction period of 3 hours, the culture was harvested and the cells were taken up in 40 mM Hepes/NaOH, pH 7.5, and disrupted by means of French press. Thereafter, the $His_6$-tag-fused aminotransferase was purified by means of $Zn^{2+}$-activated iminodiacetic Sepharose and a buffer exchange was performed by gel filtration on Superdex 200 in 25 mM Hepes/NaOH, pH 8.3. The purified enzyme was then employed directly in the diulose transamination enzyme assay.

The enzyme assay was composed as follows:

| Buffer and solutions | Final concentration in the mixture |
|---|---|
| Hepes/NaOH buffer pH 8.3 | 25 mM |
| Diulose | 25 mM |
| L-Alanine | 8 mM |
| Pyridoxal phosphate | 0.3 mM |
| Purified enzyme | 10 μM |
| Total volume | 250 μl |

Thereafter, the mixture was first subjected to FMOC derivatization and then measured by HPLC. FIG. 18 shows the HPLC chromatogram of the separation of the reaction mixture of the enzymatic conversion of diulose (VII) by a *Mesorhizobium loti* aminotransferase.

Example 17

Production of a *Rhodobacter sphaeroides* Aminotransferase, and Amination of Diulose (VII) Using the Latter The gene (SEQ ID NO: 32) of the aminotransferase was amplified from genomic *Rhodobacter* sphaeroides DSM158 DNA and subsequently inserted into a pASK-IBA35+ vector with N-terminal $His_6$ tag with removal of the N-terminal ATG of the aminotransferase gene. The cleavage sites EheI and HindIII were used for this purpose.

The vector with the target gene was subsequently employed for transforming the target organism *E. coli* BL21.

The expression of the aminotransferase was induced during the exponential growth phase at $OD_{550}$ 0.5 by adding 0.2 μg/ml AHT. After an induction period of 3 hours, the culture was harvested and the cells were taken up in 40 mM Hepes/NaOH, pH 7.5, and disrupted by means of French press. Thereafter, the $His_6$-tag-fused aminotransferase was purified by means of $Zn^{2+}$-activated iminodiacetic Sepharose and a buffer exchange was performed by gel filtration on Superdex 200 in 25 mM Hepes/NaOH, pH 8.3. The purified enzyme was then employed directly in the diulose transamination enzyme assay.

The enzyme assay was composed as follows:

| Buffer and solutions | Final concentration in the mixture |
|---|---|
| Hepes/NaOH buffer pH 8.3 | 25 mM |
| Diulose | 25 mM |
| L-Alanine | 8 mM |
| Pyridoxal phosphate | 0.3 mM |

-continued

| Buffer and solutions | Final concentration in the mixture |
|---|---|
| Purified enzyme | 10 µM |
| Total volume | 250 µl |

Thereafter, the mixture was first subjected to FMOC derivatization and then measured by HPLC. FIG. 19 shows the HPLC chromatogram of the separation of the reaction mixture of the enzymatic conversion of diulose (VII) by a *Rhodobacter sphaeroides* aminotransferase.

We claim:

1. A process for aminating at least one keto group in a multicyclic ring system comprising at least one keto group to give an amino group, the method comprising:
   contacting the multicyclic ring system with at least one enzyme E with transaminase activity,
   wherein the enzyme E with transaminase activity comprises the polypeptide sequence selected from the group consisting of SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31, or
   a functional equivalent of the enzyme comprising SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31, wherein up to 5% of the amino acid residues have been modified over the corresponding sequence of SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29 and SEQ ID NO: 31 respectively, by deletion, insertion, substitution, insertion or a combination of deletion, substitution and insertion and which retains at least 50% of the enzymatic activity of the corresponding enzyme of SEQ ID NO: 2, SEQ ID NO: 4, SEQ ID NO: 7, SEQ ID NO: 13, SEQ ID NO: 15, SEQ ID NO: 17, SEQ ID NO: 19, SEQ ID NO: 21, SEQ ID NO: 27, SEQ ID NO: 29, and SEQ ID NO: 31, respectively.

2. The process of claim 1, wherein the multicyclic ring system employed comprises cis-linked rings.

3. The process of claim 1, wherein the multicyclic ring system employed comprises at least one selected from the group consisting of

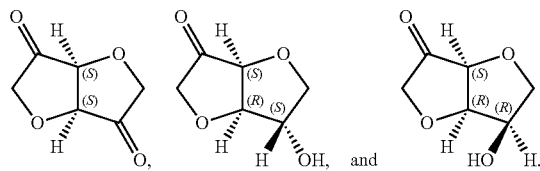

4. The process of claim 1, wherein the multicyclic ring system is obtained by oxidizing at least one secondary hydroxyl group of a multicyclic starting ring system to give a ketone.

5. The process of claim 4, wherein the multicyclic starting ring system comprises at least one secondary hydroxyl group, and at least one of the secondary hydroxyl groups is in the endo-position relative to the multicyclic starting ring system.

6. The process of claim 4, wherein the multicyclic starting ring system comprises at least one secondary hydroxyl group, and at least one of the secondary hydroxyl groups is in the exo-position relative to the multicyclic starting ring system.

7. The process of claim 4, wherein the multicyclic starting ring system is at least one compound selected from the group consisting of:
   isomannide;
   isosorbide;
   isoidide;

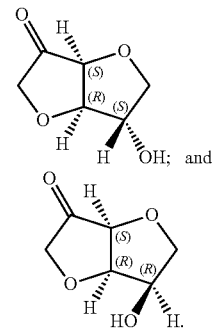

8. The process of claim 4, wherein the oxidizing is catalyzed by an enzyme F with alcohol dehydrogenase activity.

9. The process of claim 8, wherein at least one byproduct generated by enzymatic reactions of the enzymes E and F are regenerated by at least one enzyme G with amino acid dehydrogenase activity.

10. The process of claim 1, wherein a ratio of enantiomers formed, of at least one ring system comprising at least one amino group, is influenced by varying at least one reaction condition.

11. The process of claim 1, wherein the enzyme E with transaminase activity comprises the polypeptide sequence selected from the group consisting of SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31.

12. The process of claim 1, wherein the enzyme E with transaminase activity comprises a polypeptide sequence that is a functional equivalent of the enzyme comprising SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31, wherein up to 5% of the amino acid residues have been modified over the corresponding SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31, respectively, by deletion, insertion, substitution, insertion or a combination of deletion, substitution and insertion and which retains at least 50% of the enzymatic activity of the corresponding enzyme of SEQ ID NO: 2, SEQ ID NO: 4, SEQ ID NO: 7, SEQ ID NO: 13, SEQ ID NO: 15, SEQ ID NO: 19, SEQ ID NO: 21, SEQ ID NO: 27, SEQ ID NO: 29, and SEQ ID NO: 31, respectively.

13. The process of claim 12, wherein the enzyme E retains at least 80% of the enzymatic activity of the corresponding enzyme.

14. The process of claim 12, wherein the enzyme E retains at least 90% of the enzymatic activity of the corresponding enzyme.

15. The process of claim 11, wherein the enzyme E with transaminase activity comprises the polypeptide sequence selected from the group consisting of SEQ ID NO: 2, and SEQ ID NO: 4.

16. The process of claim 12, wherein the enzyme E with transaminase activity comprises a polypeptide sequence that is a functional equivalent of the enzyme comprising SEQ ID NO: 7, SEQ ID NO: 13, SEQ ID NO: 15, SEQ ID NO: 19, SEQ ID NO: 21, SEQ ID NO: 27, SEQ ID NO: 29, or SEQ ID NO: 31, wherein up to 5% of the amino acid residues have been modified over the corresponding SEQ ID NO: 7, SEQ ID NO: 13, SEQ ID NO: 15, SEQ ID NO: 19, SEQ ID NO: 21, SEQ ID NO: 27, SEQ ID NO: 29, or SEQ ID NO: 31, respectively, by deletion, insertion, substitution, insertion or a combination of deletion, substitution and insertion and which retains at least 50% of the enzymatic activity of the corresponding enzyme of SEQ ID NO: 7, SEQ ID NO: 13, SEQ ID NO: 15, SEQ ID NO: 19, SEQ ID NO: 21, SEQ ID NO: 27, SEQ ID NO: 29, or SEQ ID NO: 31, respectively.

* * * * *